(12) United States Patent
Laine et al.

(10) Patent No.: US 8,110,366 B2
(45) Date of Patent: Feb. 7, 2012

(54) METHOD FOR EVALUATING CELL POPULATIONS

(75) Inventors: Jarmo Laine, Helsinki (FI); Taina Jaatinen, Helsinki (FI); Heidi Anderson, Helsinki (FI); Johanna Nystedt, Helsinki (FI); Sarl Tiitinen, Vantaa (FI); Anita Laitinen, Helsinki (FI); Ulla Impola, Helsinki (FI); Tero Satomaa, Helsinki (FI); Jari Natunen, Vantaa (FI); Annamari Heiskanen, Helsinki (FI); Maria Blomqvist, Itasalmi (FI); Anne Olonen, Lahti (FI)

(73) Assignees: Suomen Punainen Risti, Veripalvelu, Helsinki (FI); Glykos Finland Oy, Helsinki (FI)

( * ) Notice: Subject to any disclaimer, the term of this patent is extended or adjusted under 35 U.S.C. 154(b) by 804 days.

(21) Appl. No.: 11/988,418

(22) PCT Filed: Jul. 7, 2006

(86) PCT No.: PCT/FI2006/050323
§ 371 (c)(1),
(2), (4) Date: Jul. 15, 2008

(87) PCT Pub. No.: WO2007/006864
PCT Pub. Date: Jan. 18, 2007

(65) Prior Publication Data
US 2009/0148839 A1 Jun. 11, 2009

(30) Foreign Application Priority Data
Jul. 8, 2005 (FI) .................................... 20055398

(51) Int. Cl.
*G01N 31/00* (2006.01)
*G01N 33/53* (2006.01)
(52) U.S. Cl. .......... 435/7.1; 435/4; 435/287.9; 436/501; 436/518; 436/525; 436/529; 436/535; 436/809; 427/287; 427/337; 427/338
(58) Field of Classification Search .................. None
See application file for complete search history.

(56) References Cited

U.S. PATENT DOCUMENTS

| 5,965,457 A | 10/1999 | Magnani |
| 2004/0253233 A1 | 12/2004 | Del Rio et al. |

FOREIGN PATENT DOCUMENTS

| WO | WO-2004/019040 A1 | 3/2004 |
| WO | WO-2004/094619 A2 | 11/2004 |

OTHER PUBLICATIONS

Li et al., "Abstracts submitted for the joint meeting of the society for glycobiology and the Japanese society for carbohydrate research," 2004, Abstract (347), pp. 1040 and 1150.
Martin et al., "Human embryonic stem cells express an immunogenic nonhuman sialic acid," Technical Reports, Nature Medicine, vol. 11, No. 2, 2005, pp. 228-232.
Minch et al., "Tissue Plasminogen Activator Coexpressed in Chinese Hamster Ovary Cells with α(2,6)-Sialyltransferase Contains NeuAcα(2,6)Galβ(1,4)Glc-N-AcR Linkages," Biotechnol. Prog., vol. 11, 1995, pp. 348-351.
Kudo et al., "Characterization of the Major Core Structures of the α2→8-linked Polysialic Acid-containing Glycan Chains Present in Neural Cell Adhesion Molecule in Embryonic Chick Brains," The Journal of Biological Chemistry, vol. 271, No. 51, 1996, pp. 32667-32677.
Unverzagt et al., "Structure-Activity Profiles of Complex Biantennary Glycans with Core Fucosylation and with/without Additional α2,3/α2,6 Sialylation: Synthesis of Neoglycoproteins and Their Properties in Lectin Assays, Cell Binding, and Organ Uptake," J. Med. Chem., vol. 45, 2002, pp. 478-491.

*Primary Examiner* — Lisa Cook
(74) *Attorney, Agent, or Firm* — Birch, Stewart, Kolasch & Birch, LLP.

(57) ABSTRACT

The invention describes specific sialylated structures present on human stem cells and cell populations derived thereof. The invention is especially directed to methods to control the status of stem cells by observing changes in sialylation of the cells; and control of potential contaminations of biological materials; and reagents and methods used in connection with the cells in order to avoid alterations of the cell glycosylation by contaminating materials. The invention is further directed to novel stem cells, the glycosylation of which has been specifically altered.

66 Claims, 21 Drawing Sheets

```
   1   C  C  A  Y  H  L  L  K  L  P  V  L  R  K  E  S  I  S  F  A  I  R  A  L  A  K  T  T  S  C
   1 CTGTTGTGCCTATCACCTGTTGAAGTTGCCAGTCTTAAGGAAGAATCAATTTCTTCGCAATAAGAGCACTGGCAAAGACTACGTCTTGT
  31   T  R  I  R  A  D  -  G  H  A  R  I  C  A  S  T  K  E  A  C  S  -  K  I  S  R  I  -  P  E
  92 ACAAGAATAAGAGCCGACTGAGGGCATGCAAGAATATGTGCAAGCACCAGGAGGCCTGTTCATAAAGATATCGAGGATTTAGCCGGAA
  61   V  V  E  M  D  E  N  N  G  L  L  L  L  E  L  N  P  P  N  P  W  D  L  Q  P  R  S  P  E  E
 182 GTTGTTGAAATGGATGAAAACAACGGACTTTGCTTTTAGAACTGAATCCTCCTAACCCTTGGACTTACAGCCCAGATCTCCTGAAGAG
  91   L  A  F  G  E  V  Q  I  T  Y  L  T  H  A  C  M  D  L  K  L  G  D  K  R  M  V  F  D  P  W
 272 TTGGCTTTTGGAGAAGTACAGATAACATATCTCACTCATGCCTGCAGTTAGGACACAAGAAATGGTGTTTGACCCTTGG
 121   L  I  G  P  A  F  A  R  G  W  W  L  L  H  E  P  P  S  D  W  L  E  R  L  C  Q  A  D  L  I
 362 TTAATCGGTCCTGCTTTTGCCCGTGGATGGTGGTTGCTCCATGAGCCTCCATCTGATTGGCTGGAGAGGCTGTGCCAGGCAGACCTATT
 151   V  I  S  H  L  H  S  D  D  H  L  S  Y  P  T  L  K  K  L  A  G  R  R  P  D  I  P  I  Y  V  G
 452 TACATCAGTCATCTGCACTCAGACCACCTGAGTTACCCCACACTGAAAAAGCTTGCTGGGAGAAGACCAGATATTCCCATTATGTTGGA
 181   N  T  E  R  P  V  F  W  N  L  N  Q  S  G  V  Q  L  T  N  I  N  V  V  P  F  G  I  W  Q  Q
 542 AACACAGAAAGGCCTGTATTTTGGAATCTGAATCAGAGCGGTGTCCAGTTGACTAATATCAATGTCGTGCCATTTGGAATATGGCAGCAG
 211   V  D  K  N  L  R  F  M  I  L  M  D  G  V  H  P  E  M  D  T  C  I  I  V  E  Y  K  G  H  K
 632 GTGGACAAAAATCTTCGATTCATGATCTTGATGGACGGTGTTCATCCTGAGATGGACACTTGCATTATTGTGGAGTACAAAGGTCATAAA
 241   I  L  N  I  V  D  C  T  R  P  N  G  G  R  L  P  M  K  V  A  L  M  M  S  D  F  A  G  G  A
 722 ATACTCAATATAGTAGACTGCACCAGACCCAATGGGGGACGTCTGCCTATGAAGGTTGCTTTAATGATGAGTGATTTTGCTGGAGGAGCA
 271   S  G  F  F  P  M  T  F  S  G  G  K  F  T  E  E  W  K  A  Q  F  I  K  T  E  R  K  K  L  L  N
 812 TCAGGCTTTCCAATGACTTTCAGTGGTGGAAAATTTACGGAGGAATGGAAAGCCCAATTCATTAAAACAGAAAGGAAGAAGCTCCTGAAC
 301   Y  K  A  R  L  V  K  N  L  Q  P  R  I  Y  C  P  F  A  G  Y  I  F  V  E  S  H  P  S  D  K  Y
 902 TACAAGGCTCGGCTGGTGAAGAACCTGCAACCCAGAATTTATTGTCCCTTTGCTGGGTATTTCACCCATCAGACAAGTAC
 331   I  K  E  T  N  T  K  N  D  P  N  E  L  N  N  L  I  K  K  N  S  D  V  I  T  W  T  P  R  P
 992 ATCAAGGAAACAAACACAAAATGACCCAAATGAACTGAACAATCTTATCAAGAAAAACTCTGATGTGATAACATGACCCCTCGACCG
 361   G  A  T  L  D  L  G  R  M  L  K  D  R  T  D  S  K  G  I  H  E  P  P  E  G  T  K  I  Y  K
1082 GGAGCCACCCTTGATCTGGGAAGAATGCTGAAGGATCGAACAGCAAGGCATCATAGACCCTCCAGAGGGACAAAAATTTACAAG
 391   D  S  W  D  F  E  P  Y  L  E  I  L  N  A  A  L  G  D  E  I  F  L  H  S  S  W  I  K  E  Y
1172 GATTCCTGGGATTTTGAACCTTATTTGGAAATTCTGAATGCTGCCCTAGGAGATGAAATATTTCTTCACTCATCCTGGATAAAGAATAC
 421   L  T  W  A  G  F  K  D  Y  N  L  V  V  R  M  I  E  T  D  E  D  F  N  P  F  P  G  G  Y  D
1262 CTCACTTGGGCTGGATTTAAAGATTACAACCTTGTGGTCAGGATGATTGAGACAGATGAGGACTTCAATCCTTTTCCTGGAGGATATGAC
 451   V  L  V  D  F  L  D  L  S  F  P  K  E  R  P  Q  R  E  H  P  Y  E  E  I  H  S  R  V  D  V
1352 GTTCTTGTTGACTTTTTAGATTTATCCTTCCCAAAAGAAAGACCACACAGAGAACATCCCTATGAGGAAATCCATAGCCGGGTGGATGTC
 481   I  R  H  V  V  K  N  G  L  L  W  D  E  L  Y  I  G  F  Q  T  R  L  Q  R  D  P  D  I  Y  H
1442 ATCAGACACGTGGTGAAGAATGGTCTACTCTGGGATGAGTTGTATATAGGATTCCAAACACGGCTCCAGCGGGATCCTGACATATACCAT
 511   H  L  F  W  N  H  F  Q  I  H  L  T  P  P  N  W  K  S  F  L  M  C  C  E  Q  N  G  P
1532 CACCTGTTTTGGAATCATTTTCAAATAAATACTCCCCCTCACACCAACTGGAATGGAAATCTGAGATGGCAGAATGGCCT
 541   A  I  L  Q  F  S  T  E  R  T  N  E  P  N  R  N  K  F  S  V  E  N  K  A  -
1622 GCGATTTTGCAATTCTCTACAGAAAGAACCAATGAACCCAATGAACCAAGACAATTCTGTGGAAAACAAGCATAGCTGTAGATACGA
1712 ATCCAATCACAGAGGAAACAGGAAGAGAAAATCCAAGACTACAGTGAAAACTGGAAACTGTCTGTTTTCGTGATATTCGTATGATTA
1802 AGATGCAAATTTTTTCTTAGGAAATGTGATTGTTAACTAGCATTCTGTTTACATGATGTTGACATTTCTAACACACCACTGATTTGA
1892 ACTTCAAAATTTATTTCTGATTATATATGCTAGGTCTGATTCTGAAGATACAAGAATTCAATGGTGAATTTGTCTCCTG
```

```
          1 CTGTTGTGTGCCTATCACCTGTTGAAGTTGCCAGTCTTAAGGAAGGAATCAA  50
F1        1  L  L  C  L  S  P  V  E  V  A  S  L  K  E  G  I  N    17
F2        1  C  C  A  Y  H  L  L  K  L  P  V  L  R  K  E  S  I    17
F3        1  V  V  P  I  T  C  *  S  C  Q  S  *  G  R  N  Q        4

51 TTTCTTTCGCAATAAGAGAGCACTGGCAAAGACTACGTCTTGTACAAGAATA 100
F1       18  F  F  R  N  K  S  T  G  K  D  Y  V  L  Y  K  N  K    34
F2       18  S  F  A  I  R  A  L  A  K  T  T  S  C  T  R  I       33
F3        5  F  L  S  Q  *  E  H  W  Q  R  L  R  L  V  Q  E  *    11

101 AGAGCCGACTGAGGGCATGCAAGAATATGTGCAAGCACCAAGGAGGCCTG  150
F1       35  S  R  L  R  A  C  K  N  M  C  K  H  Q  G  G  L       50
F2       34  R  A  D  *  G  H  A  R  I  C  A  S  T  K  E  A  C    13
F3        1  E  P  T  E  G  M  Q  E  Y  V  Q  A  P  R  R  P  V    17
                                                       ➤
        151 TTCATAAAAGATATCGAGGATTTAGCCGGAAGTTGTTGAAATG        193
F1       51  F  I  K  D  I  E  D  L  A  G  S  C  *  N             1
F2       14  S  *  K  I  S  R  I  *  P  E  V  V  E  M             6
F3       18  H  K  R  Y  R  G  F  S  R  K  L  L  K                30
```

Figure 8 (continued)

```
               510       520       530       540       550       560       570       580       590       600
                |         |         |         |         |         |         |         |         |         |
HUCB       FPKERPQREHPYEEIHSRVDVIRHVVKNGLLWDELYIGFQTRLQRDPDIYHHLFWNHFQIKLPLTPPNWKSFLMCCEQNGPAILQFSTERTNEPNRNKFS
pan        FPKERPQREHPYEEIHSRVDVIRHVVKNGLLWDELYIGFQTRLQRDPDIYHHLFWNHFQIKLPLTPPNWKSFLMCCEQNGPAILQFSTERTNEPNRNKFS
gorilla    FPKERPQREHPYEEIHSRVDVIRHVVKNGLLWDELYIGFQTRLQRDPDIYHHLFWNHFQIKLPLTPPNWKSFLMCCEQNGPGILQFSTERTNEPNRNKFS
Irie       FPKERPQREHPYEEIHSRVDVIRHVVKNGLLWDELYIGFQTRLQRDPDIYHHLFWNHFQIKLPLTPPNWKSFLMCCEQNGPGILQFSTERTNEPNRNKFS
mus        FPKERPSREHPYEEIHSRVDVIRYVVKNGLLWDDLYIGFQTRLLRDPDIYHHLFWNHFQIKLPLTPPNWKSFLMCCEQNGPAILQECKTT-----------
CAI20561   FPKERPQREHPYEEIHSRVDVIRHVVKNGLLWDELYIGFQTRLQRDPDIYHHLFWNHFQIKLPLTPPNWKSFLMHCD----------------------
                                                                                                          FLMCCEQNGPVILQFSTERTNEPNRNKFS HUCB       VENKA
pan        VENKA
gorilla    VENKA
Irie       -----
mus        -----
CAI20561   VENKA
```

Figure 13.
A.
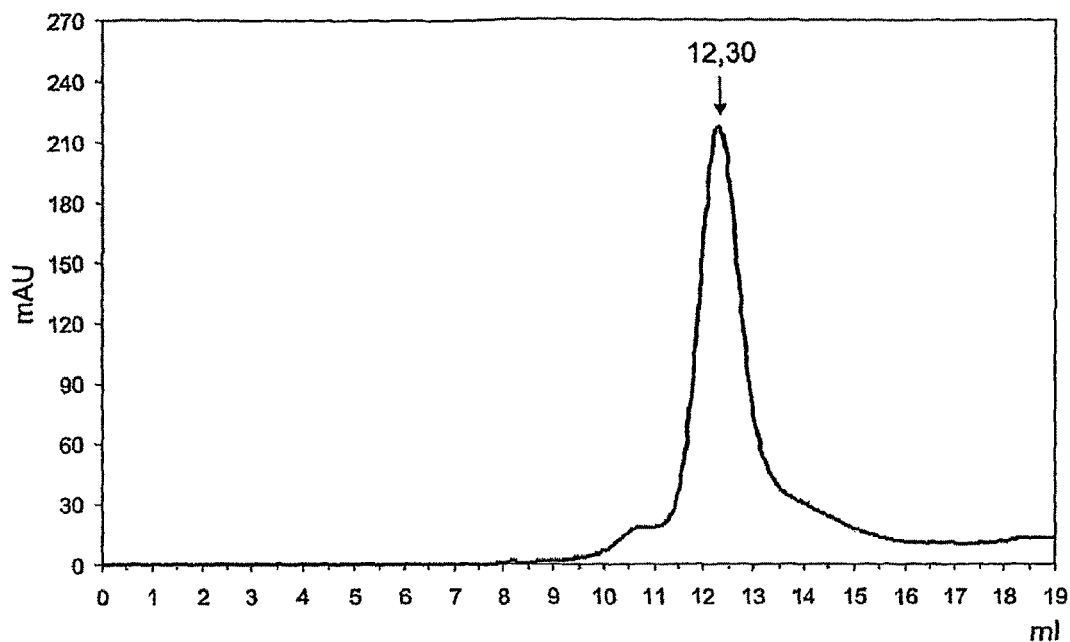
B.
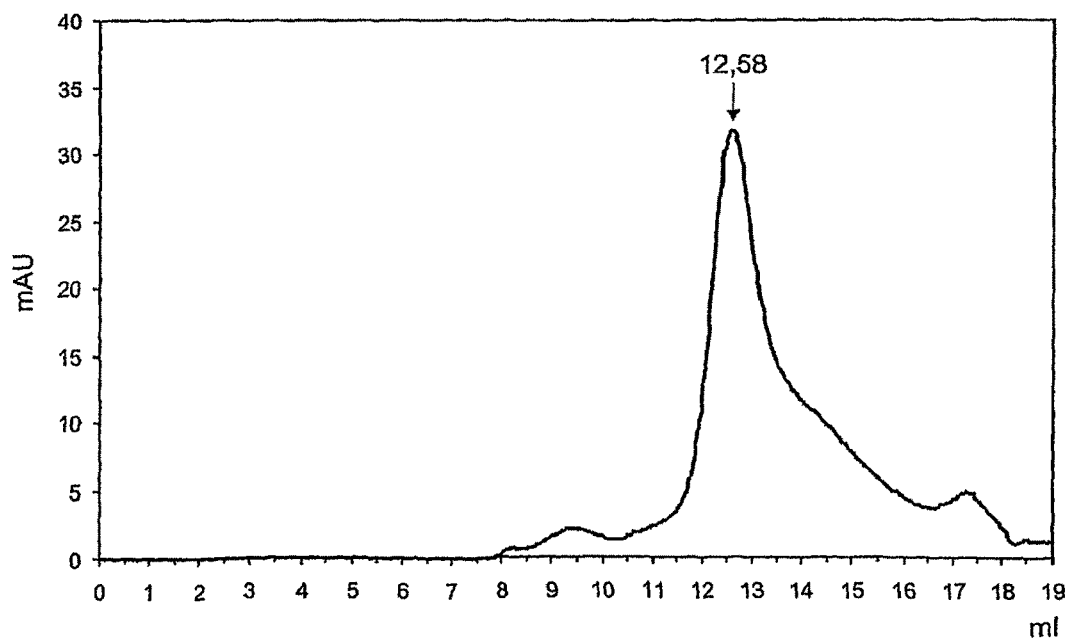

Figure 15.
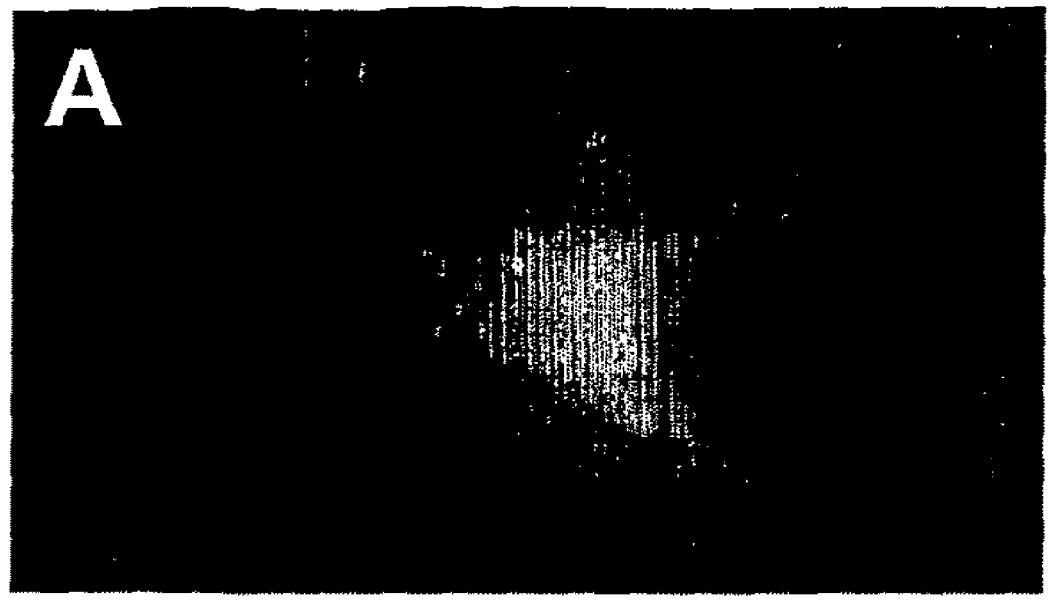
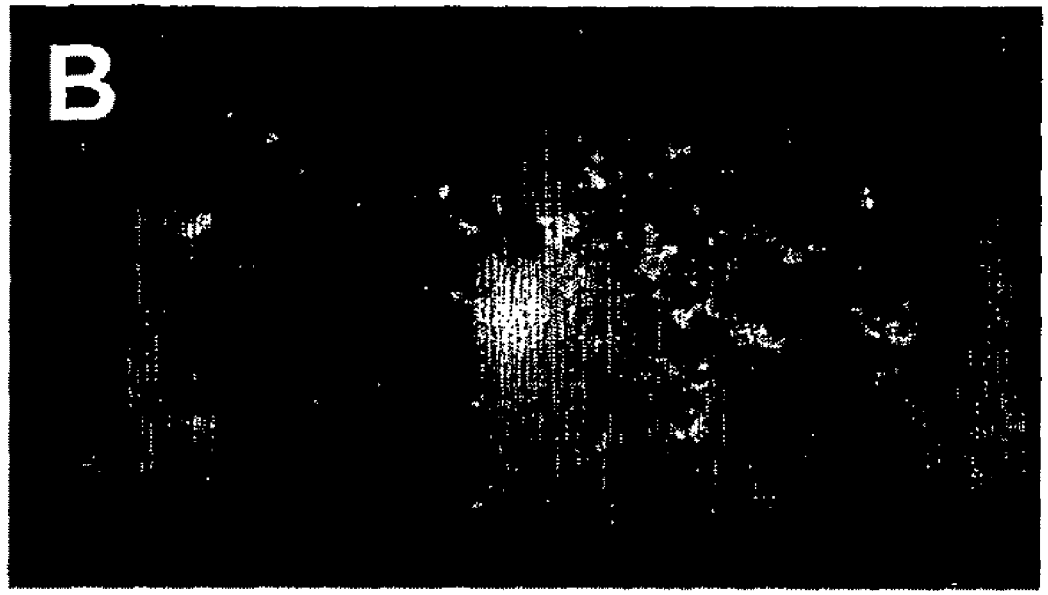

METHOD FOR EVALUATING CELL POPULATIONS

This application is a continuation of PCT/FI2006/050323 filed Jul. 7, 2006 and foreign application number 2055398 filed Jul. 8, 2005 in Finland.

FIELD OF INVENTION

The invention describes specific sialylated structures present on human stem cells and cell populations derived thereof. The invention is especially directed to methods to control the status of stem cells by observing changes in sialylation of the cells; and control of potential contaminations of biological materials; and reagents and methods used in connection with the cells in order to avoid alterations of the cell glycosylation by contaminating materials. The invention is further directed to novel stem cells, the glycosylation of which has been specifically altered. The control methods are preferably mass spectrometric methods.

BACKGROUND OF THE INVENTION

Martin et al. (2005, *Nat. Med.*, publ. online Jan. 30, 2005, doi 10.1038i)

Analysis of sialylated glycans from embryonal stem cells was produced in USA and reported for human embryonal stem cell lines, such cell lines have been reported to be contaminated with N-glycolylneuraminic acid (NeuGc) and amounts of both NeuGc and N-acetylneuraminic acid (NeuAc) have been quantitated. The scientists further discussed cell culture materials containing NeuGc and causing contamination of the cultivated cell lines and for handling the problem by using alternative recombinant protein materials and especially heat inactivated human serum not originally containing NeuGc.

The inventors of the present invention were able to find new sources of potential NeuGc and other sialyl-glycan contaminations. The present invention further describes specific sialyl-glycan structures from early human cells. The inventors were also able to describe specific protein reagents involved in cell production processes, which need to be controlled with regard to glycosylation, especially albumin, gelatine, and antibody reagents.

Varki, U.S. patent document 2005

The patent document describes monosaccharide NeuGc analysis from foods and other materials. There are specific claims for the proportion of NeuGc of the sum of NeuGc and NeuAc, especially in food materials. The document further describes anti-NeuGc antibodies present in patients and production of antibodies involving oxidation of the glycerol tail of NeuGc. The incorporation of NeuGc to a cultured endothelial (cancer) cell line was studied in serum containing culture by adding free NeuGc.

Analysis of CD34+ Hematopoietic Stem Cell Materials with Regard to NeuAcα3Galβ4

NeuAcα3Galβ4 structures have been previously indicated to be present in human cord blood CD34$^+$ hematopoietic cells by the use of a specific monoclonal antibody (Magnani, J., et al., U.S. Pat. No. 5,965,457.). The invention claims all CD34+ cells and especially ones from cord blood and bone marrow The inventors of the present invention were able to analyse, in human stem cell and cord blood cell populations, the presence of both NeuAcα3 and NeuAcα6 structures and even NeuGcα3/6, and larger sialylated structures, including also information about the glycan core structures by which the glycans are linked to the cell. The present invention is in a preferred embodiment directed to analysis of at least two or several sialylated terminal epitopes or at least one whole glycan structure. In a preferred embodiment the sialic acid analysis of cord blood cells is directed to multipotent cell populations, which are not CD34$^+$ hematopoietic progenitor cells. Preferably the analysis includes analysis of the core structures of N-linked glycans since Magnani et al. (U.S. pat.) do not describe the core structures by which the glycans are linked to the cells.

Desialylation and Resialylation of Cells According to the Invention

Change of sialylation by desialylation and resialylation with specific sialyltransferases has been reported for red cells in order to analyze binding specificities of influenza virus (Paulson, J., et al.).

Partial desialylation and alpha-6-resialylation with CMP-NeuAc-fluorescein of human peripheral blood and bone marrow aspirate-derived CD34+ cells has been reported, the peripheral blood cells having been released by GM-CSF and most of the subjects being under cancer therapy (Schwarz-Albiez, Reihard et al., 2004, Glycoconj. J. 21 451-459). The large variations in results may be due to therapy and GM-CSF. The method used does not reveal real quantitation of sialic acid types due to limited specificity of especially the sialyltransferase used, nor are the possible carrier structures of the sialic acids revealed. The modifications of sialic acid would likely further affect the acceptor specificity of the sialyltransferase used and thus the structures labelled. The present invention is especially directed to α3-sialylation of the specific carrier structures.

Removal of NeuGc from pig xenotransplant tissue and resialylation by NeuAc and sialyltransferase has been also suggested (WO02088351)). That work was not directed to stem cells, nor human stem cells directed methods, nor were the methods used specified, although this is essential for applications in these cells. The xenotransplantation idea is not relevant to present invention due to tissue and species specificity of glycosylation. A patent application (WO2003/105908) describes possible sialidase and sialyltransferase reactions for certain NK/lymphocyte cell lines in a patent application also discussing separately stem cells. The results reveal that the possible reactions vary between cell lines of the same type and are not expected/predictable under the conditions used in the work, possibly partially due to nature of the cells and specificities of enzymes, further the reaction conditions of sialyltransferase without CMP-sialic acid are not described by the invention.

Methods of removal of terminal Gal or GalNAc from human red cells have also been described as well as galactosylation of human platelets in the context of cryopreservation induced changes in human platelets (Zymequest; Science 2004).

None of the reports describe the specific expression of the preferred sialylated N-glycan structures of human stem cells and cord blood cells. It is generally known that glycosylation is cell type specific, and this has been further indicated by the present invention. It cannot be known in advance and based on prior art if the cells contain sialic acid residues removable by specific sialidase enzymes or specific acceptor sites for specific sialyltransferases. Specific sialyltransferases according to the invention, especially recombinant human sialyltransferases controlled with regard to glycosylation, are preferred for the process described in the present invention. The present invention is further directed to the synthesis of the specific sialylated glycan structures according to the present invention, which have not been described in the background publications.

NeuGc Recognizing Antibodies

Production and purification of polyclonal antibodies, which recognize NeuGc has been published by Varki and colleagues, Martin et al 2005 (antibody production WO2005010485). The specificity appears to be broad and glycerol side chain of the antigen is removed further restricting the specificity. Several antibodies against NeuGc structures has been published but suitability of these against stem cells is not known.

Removal of NeuGc from Bovine Serum Proteins

Acid Hydrolysis for Desialylation of Aglycoprotein

Acid hydrolysis method has been described for desialylation of a glycoprotein called fetuin (Spiro et al., 1982) using 12.5 mM sulfuric acid at 80 degrees of Celsius. This method was designed to release sialic acid quantitatively from the glycoprotein. However, the amount of degraded protein was not analyzed. The inventors realized that under conditions of Spiro et al. the protein polypeptide chain of fetuin and other proteins are heavily degraded to smaller molecular weight fragments. The present invention revealed novel methods, which allow preserving the protein intact and production specific sialylation levels and structures on glycoproteins.

The method of Spiro et al has not been described for NeuGc and/or α6-linked sialic acids (the invention was revealed to be effective for α6-sialylated proteins). The present invention is especially directed to controlled reduction and/or increase of NeuGc on glycans of a protein and control of α6-sialylated structures on protein. The preferred protein according to the invention includes bovine serum proteins, though it is realized that the methods are suitable for modification of other proteins, too.

BRIEF DESCRIPTION OF THE DRAWINGS

FIG. 7. A. Nucleotide sequence of 1972 bp and deduced amino acid sequence in open-reading frame of full-length CMAH cDNA from human umbilical cord blood cells. Bold uppercase letters indicates amino acid sequence. B. 5'-end sequence of cloned human umbilical cord blood cell CMAH cDNA. Sequence translated in all forward reading frames (F1-3). Arrow indicates position of 92 bp exon in mouse and monkey CMAH. Bold M indicates start methionine in the open-reading frame.

FIG. 13 shows that the milder HCl method in lower than +80° C. temperatures (FIG. 13a) results in significantly less protein degradation than the method of Spiro (1960; FIG. 13b).

FIG. 15. Selective uptake of polyvalent Neu5Gc conjugate in human mesenchymal stem cells (MSC) grown in human serum, detected by anti-Neu5Gc monoclonal antibody (Neu5Gc mAb). In both figures one representative cell is shown. The shape of the cell is roughly visualized by Neu5Gc mAb staining. The chemically stained nucleus is seen in middle of the cell at the center of the figure.

Figure 1:
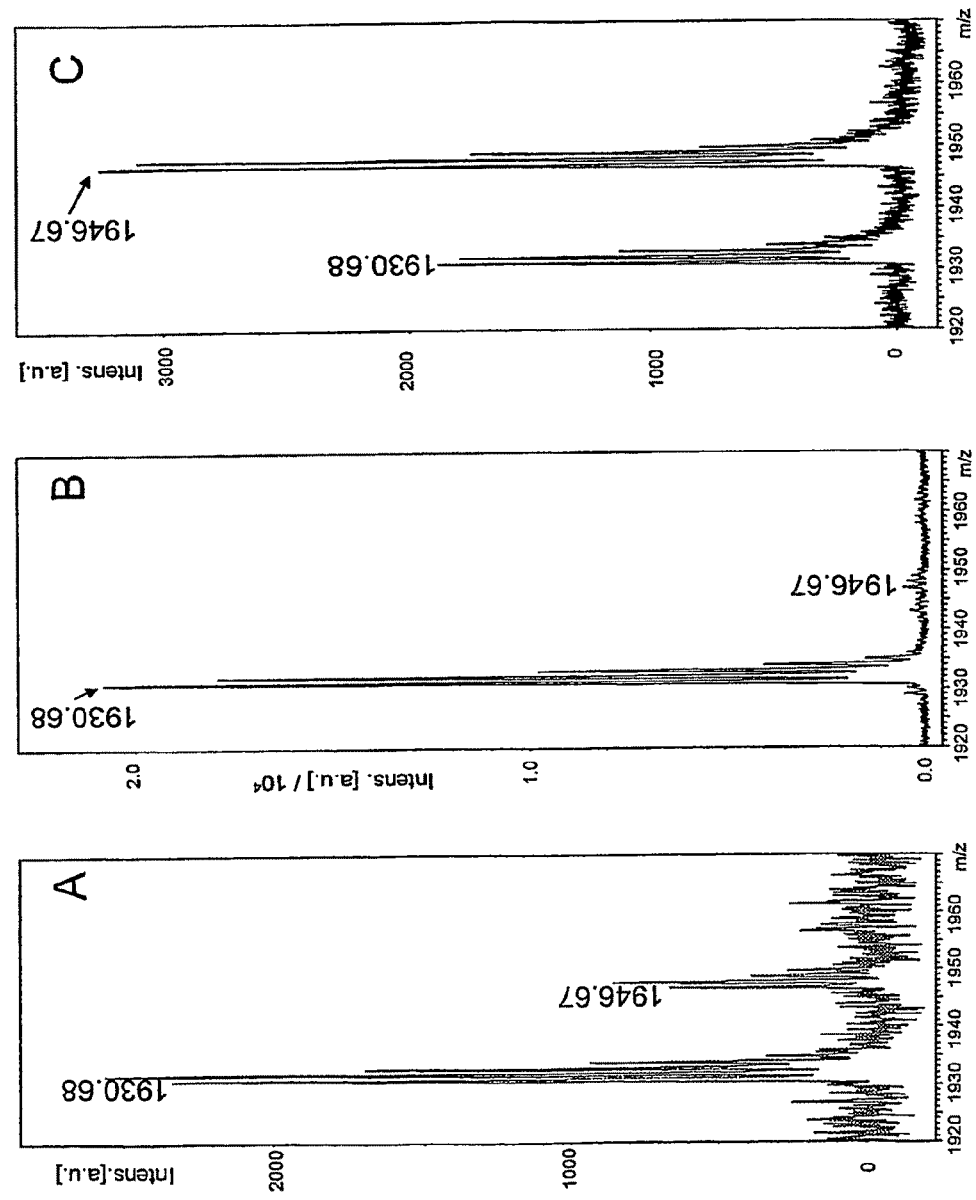
FIG. 1. MALDI-TOF mass spectrometric detection of sialylated N-glycans that are indicative of N-glycolylneuraminic acid (Neu5Gc). A. Human embryonic stem cell line, B. mesenchymal stem cell line from bone marrow, C. commercial cell culture medium with serum replacement, D. bovine serum transferrin, E. cell culture medium with fetal bovine serum (FBS), and F. fetuin from fetal bovine serum.
Figure 1:
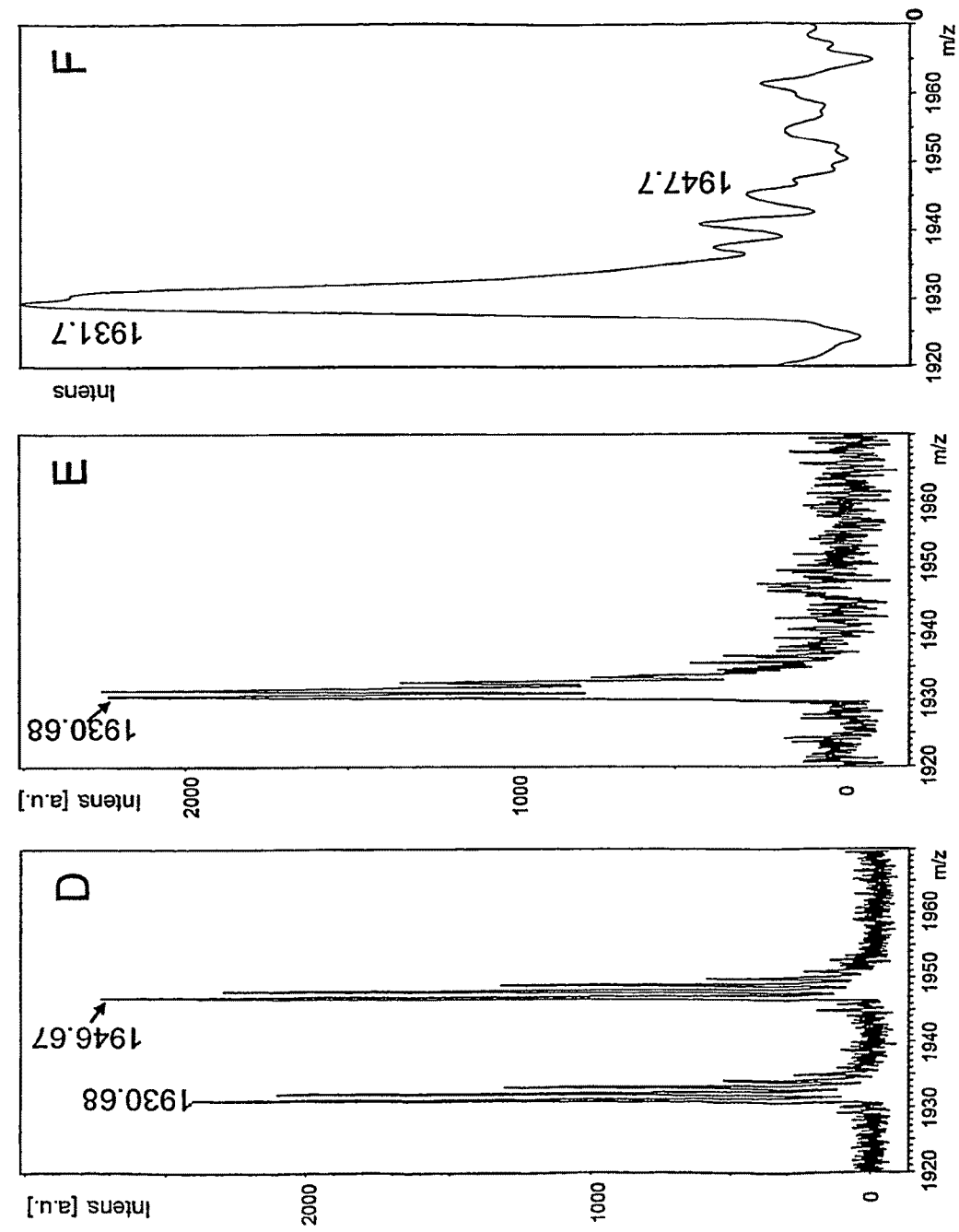
Figure 1:
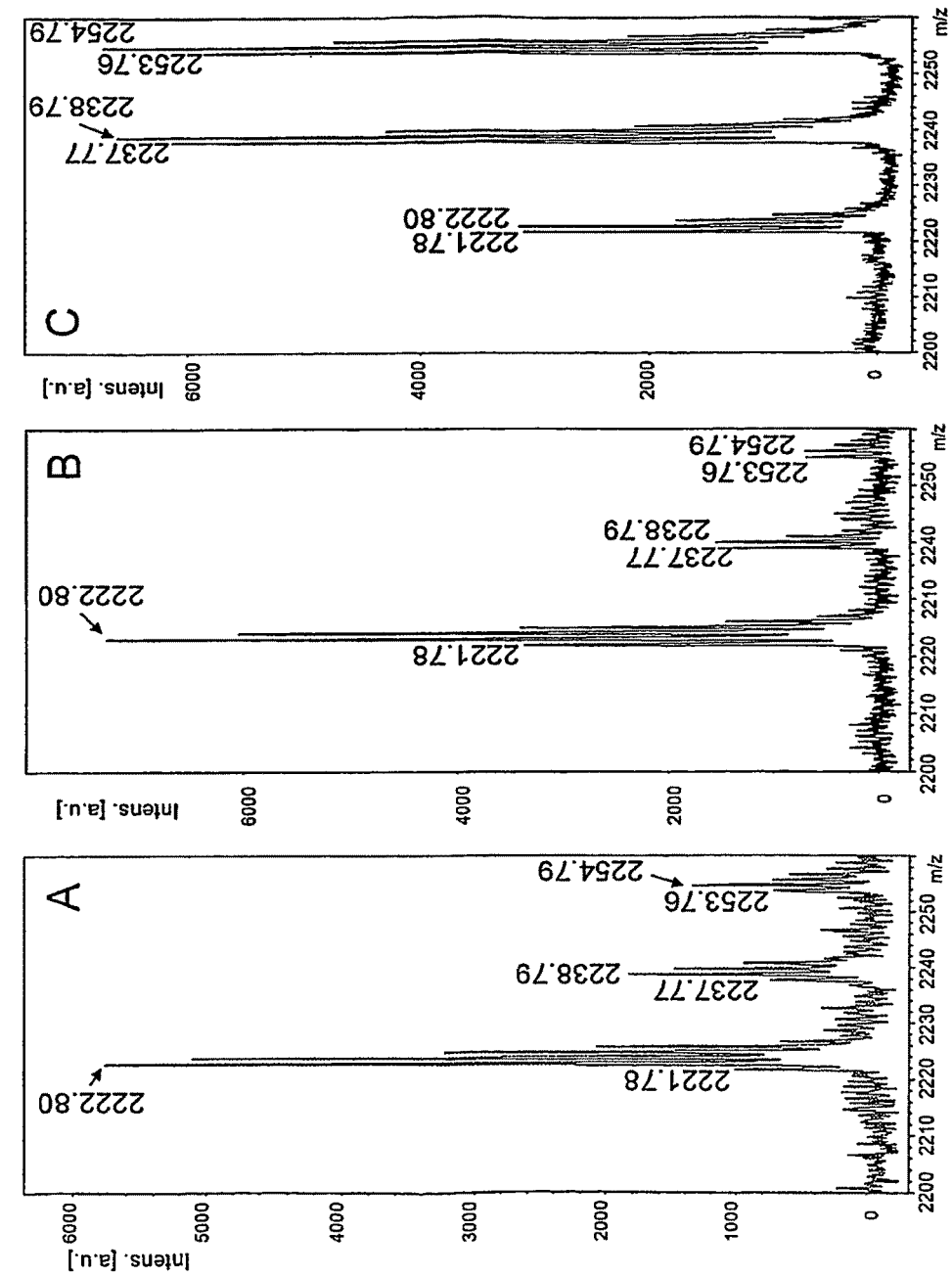
Figure 1:
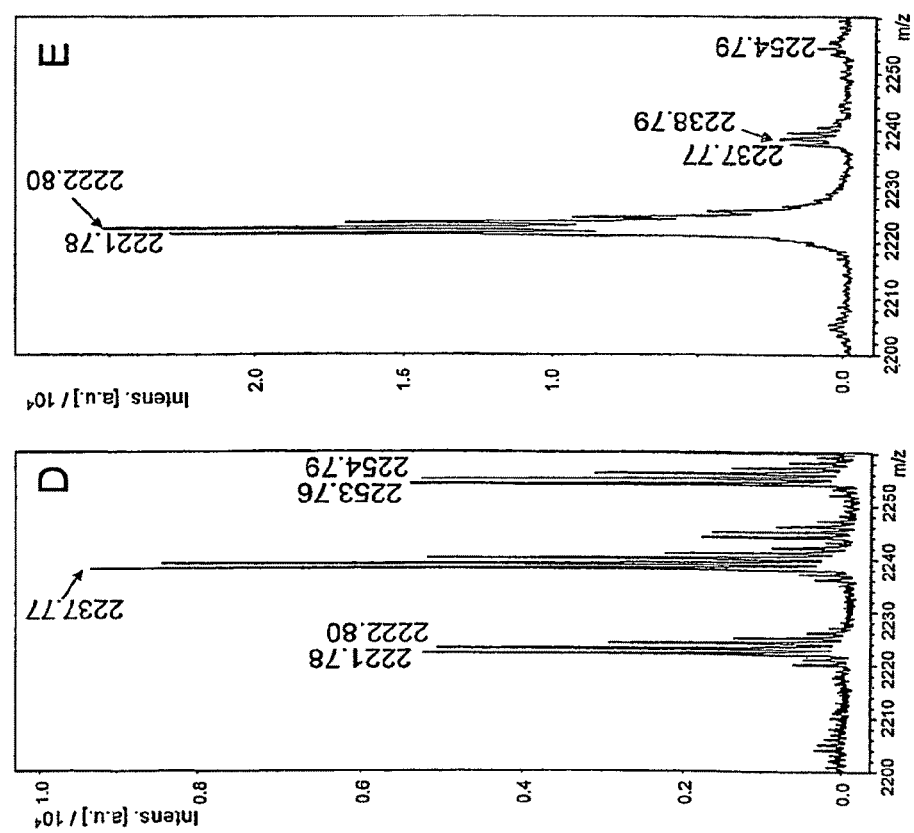

A. When polyvalent Neu5Gc conjugate was added to the culture medium, human bone marrow derived MSC took it inside the cells, specifically increasing the staining of the cells by Neu5Gc mAb.

B. The staining pattern with Neu5Gc mAb was particulate in appearance, indicating that the Neu5Gc conjugate was localized in distinct compartments of the cells.

SUMMARY OF THE INVENTION

The present invention is directed to novel glycan structures found from human stem cell and cord blood cell populations. The invention is specifically directed to specific sialylated structures present on early human cells. More preferably the sialylated structures include structures according to the formula SAα3/6Galβ(3/4GlcNAcβ)$_n$(I), wherein n is either 0 or 1, preferably the structure is linked to a N-glycan structure.

Most preferred cells are early human blood cell populations, more preferably human cord blood cells and subpopulations thereof. The early human blood cells and specific subpopulations thereof have been found useful e.g. in therapeutic cell transplantations. The present invention is specifically directed to multipotent cells capable of differentiating to non-hematopoietic cells and/or to hematopoietic cells. Under a specific embodiment the present invention is directed to embryonal-type cells and specific glycan structures related to these.

The present invention provides information and methods useful for rational control of cell products. The invention is especially directed to methods to control the status of early human cells by observing changes in glycosylation, especially sialylation of the cells; and control of potential contaminations of biological materials; and reagents and methods used in connection with the cells in order to avoid alterations of the cell glycosylation by contaminating materials.

The control methods are preferably mass spectrometric methods. The present invention is further directed to methods of recognizing the preferred glycan structures and specific subpopulations of the human early cells by specific binding agents.

The present invention is further directed to comparison methods using data derived from early human cells, especially from embryonal-type cells in order to control the presence of specific glycan structures related to the invention. The invention further describes methods for removal of the glycan structures according to the invention, preferably specific sialylated structures according to the present invention.

DETAILED DESCRIPTION OF THE INVENTION

The present invention is directed to novel glycan structures found from human stem cell and cord blood cell populations. The invention is specifically directed to specific sialylated structures present on the cells. More preferably the sialylated structures include structures according to the formula I

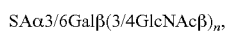

SAα3/6Galβ(3/4GlcNAcβ)$_n$, wherein n is either 0 or 1, preferably when the structure is linked to a N-glycan structure.

Most preferred cells are early human blood cell populations, more preferably human cord blood cells and subpopulations thereof. The early human blood cells and specific subpopulations thereof have been found useful e.g. in therapeutic cell transplantations. The present invention is specifically directed to multipotent cells capable of differentiating to non-hematopoietic cells. Under a specific embodiment the present invention is directed to embryonal-type cells and specific glycan structures related to these.

The present invention provides information and methods useful for rational control of cell products. The invention is especially directed to methods to control the status of human stem cells and cord blood cells by observing changes in glycosylation, especially sialylation of the cells; and control of potential contaminations of biological materials; and reagents and methods used in connection with the cells or alterations of the cell glycosylation by contaminating materials.

The control methods are preferably mass spectrometric methods. The present invention is further directed to methods of recognizing the preferred glycan structures and specific subpopulations of the early human cells by specific binding agents.

The present invention is further directed to comparison methods using data derived from early human cells, especially from embryonal-type cells in order to control the presence of specific glycan structures related to the invention. The invention further describes methods for removal of the glycan structures according to the invention, preferably specific sialylated structures according to the present invention.

Early Human Cell Populations
Human Stem Cells and Multipotent Cells

Under broadest embodiment the present invention is directed to all types of human stem cells, meaning fresh and cultured human stem cells. The stem cells according to the invention do not include traditional cancer cell lines, which may differentiate to resemble natural cells, but represent non-natural development, which is typically due to chromosomal alteration or viral transfection. Stem cells include all types of non-malignant multipotent cells capable of differentiating to other cell types. The stem cells have special capacity stay as stem cells after cell division, the self-renewal capacity.

Under the broadest embodiment for the human stem cells, the present invention describes novel special sialylated glycan structures and novel analytics, reagents and other methods directed to the glycan structures. The invention shows special differences in cell populations with regard to the novel glycan structures of human stem cells.

The present invention is further directed to the novel structures and related inventions with regard to the preferred cell populations according to the invention. The present invention is further directed to specific glycan structures, especially terminal epitopes, with regard to specific preferred cell population for which the structures are new.

Preferred Types of Early Human Cells

The invention is directed to specific types of early human cells based on the tissue origin of the cells and/or their differentiation status.

The present invention is specifically directed to early human cell populations meaning multipotent cells and cell populations derived thereof based on origins of the cells including the age of donor individual and tissue type from which the cells are derived, including preferred cord blood as well as bone marrow from older individuals or adults. Preferred differentiation status based classification includes preferably "solid tissue progenitor" cells, more preferably "mesenchymal-stem cells".

The invention is further directed to classification of the early human cells based on the status with regard to cell culture and to two major types of cell material. The present invention is preferably directed to two major cell material types of early human cells including fresh, frozen and cultured cells.

Cord Blood Cells, Embryonal-Type Cells and Bone Marrow Cells

The present invention is specifically directed to early human cell populations meaning multipotent cells and cell populations derived thereof based on the origin of the cells including the age of donor individual and tissue type from which the cells are derived.

a) from early age-cells such 1) as neonatal human, directed preferably to cord blood and related material, and 2) embryonal cell-type material b) from stem and progenitor cells from older individuals (non-neonatal, preferably adult), preferably derived from human "blood related tissues" comprising, preferably bone marrow cells.

Cells Differentiating to Solid Tissues, Preferably Mesenchymal Stem Cells

The invention is specifically under a preferred embodiment directed to cells, which are capable of differentiating to non-hematopoietic tissues, referred as "solid tissue progenitors", meaning to cells differentiating to cells other than blood cells. More preferably the cell populations produced for differentiation to solid tissue are "mesenchymal-type cells", which are multipotent cells capable of effectively differentiating to cells of mesodermal origin, more preferably mesenchymal stem cells.

Most of the prior art is directed to hematopoietic cells with characteristics quite different from the mesenchymal-type cells and mesenchymal stem cells according to the invention.

Preferred solid tissue progenitors according to the invention includes selected multipotent cell populations of cord blood, mesenchymal stem cells cultured from cord blood, mesenchymal stem cells cultured/obtained from bone marrow and embryonal-type cells. In a more specific embodiment the preferred solid tissue progenitor cells are mesenchymal stem cells, more preferably "blood related mesenchymal cells", even more preferably mesenchymal stem cells derived from bone marrow or cord blood.

Under a specific embodiment CD34+ cells as a more hematopoietic stem cell type of cord blood or CD34+ cells in general are excluded from the solid tissue progenitor cells.

Fresh and Cultivated Cells

Fresh Cells

The invention is especially directed to fresh cells from healthy individuals, preferably non-modulated cells, and non-manipulated cells.

The invention is in a preferred embodiment directed to "fresh cells" meaning cells isolated from donor and not cultivated in cell culture. It is realized by the invention that the current cell culture procedures change the status of the cells. The invention is specifically directed to analysis of fresh cell population because the fresh cells corresponding closely to the actual status of the individual donor with regard to the cell material and potential fresh cell population are useful for direct transplantation therapy or are potential raw material for production of further cell materials.

The inventors were able to show differences in the glycosylation of the preferred fresh cell populations derived from early human cells, most preferably from cord blood cells. The inventors were able to produce especially "homogenous cell populations" from human cord blood, which are especially preferred with various aspects of present invention. The invention is further directed to specific aspects of present invention with regard to cell purification processes for fresh cells, especially analysis of potential contaminations and analysis thereof during the purification of cells.

In a more preferred embodiment the fresh cells are materials related to/derived from healthy individuals. The healthy individual means that the person is not under treatment of cancer, because such treatment would effectively change the status of the cells, in another preferred embodiment the healthy person is receiving treatment of any other major disease including other conditions which would change the status of the cells.

It is realized that in some cases fresh cells may be needed to be produced for example for cell transplantation to a cancer patient using cells previously harvested from such a patient, under a separate embodiment the present invention is further directed to analysis of and other aspects of invention with regard to such cell material.

Non-Modulated Cells

Even more preferably the fresh cells are "non-modulated cells" meaning that the cells have not been modulated in vivo by treatments affecting growth factor or cytokine release. For example stem cells may be released to peripheral blood by growth factors such as CSF (colony stimulating growth factor). Such treatment is considered to alter the status of cells from preferred fresh cells. The modulation may cause permanent changes in all or part of the cells, especially by causing differentiation.

Non-Manipulated Cells

Even more preferably the fresh cells are "non-manipulated cells" meaning that the cells have not been manipulated by treatments permanently altering the status of the cells, the permanent manipulation including alterations of the genetic structure of the cells. The manipulations include gene transfection, viral transduction and induction of mutations for example by radiation or by chemicals affecting the genetic structures of the cells.

Limited Fresh Cells Excluding Certain Specifically Selected Hematopoietic Stem Cell Populations A more preferred limited group of fresh cells is directed to especially to effectively solid tissue forming cells and their precursors. Under specific embodiment this group does not include specifically selected more hematopoietic stem cell like cell populations such as a) cell population selected as CD34+ cells from peripheral blood or bone marrow and b) in another limited embodiment also total bone marrow and peripheral blood mononuclear cells are excluded.

It is realized that the fresh cell populations may comprise in part same cells as CD34+ when the cells are not selected with regard to that marker. It is realized that exact cell population selected with regard to the marker are not preferred according to the invention as solid tissue forming cells.

Another limited embodiment excludes specifically selected CD34+ cell populations from cord blood and/or total mononuclear cells from cord blood. The invention is further directed to limited fresh cell populations when all CD34+ cell populations and/or all total cell populations of peripheral blood, bone marrow and cord blood are excluded. The invention is further directed to the limited fresh cell populations when CD34+ cell population were excluded, and when both CD34+ cell populations and all the three total cell populations mentioned above are excluded.

Cultured Cells

The inventors found specific glycan structures in early human cells, and preferred subpopulations thereof according to the invention when the cells are cultured. Certain specific structures according to the invention were revealed especially for cultured cells, and special alterations of the specific glycans according to the invention were revealed in cultured cell populations.

The invention revealed special cell culture related reagents, methods and analytics that can be used when there is risk for by potentially harmful carbohydrate contaminations during the cell culture process.

Cultured Modulated Cells

It is further realized that the cultured cells may be modulated in order to enhance cell proliferation. Under specific embodiment the present invention is directed to the analysis and other aspects of the invention for cultured "modulated cells", meaning cells that are modulated by the action of cytokines and/or growth factors. The inventors note that part of the early changes in cultured cells are related to certain extent to the modulation.

The present invention is preferably directed to cultured cells, when these are non-manipulated. The invention is further directed to observation of changes induced by manipulation in cell populations especially when these are non-intentionally induced by environmental factors, such as environmental radiation and potential harmful metabolites accumulating to cell preparations.

Preferred Types of Cultured Cells

The present invention is specifically directed to cultured solid tissue progenitors as preferred cultured cells. More preferably the present invention is directed to mesenchymal-type cells and embryonal-type cells as preferred cell types for cultivation. Even more preferred mesenchymal-type cells are mesenchymal stem cells, more preferably mesenchymal stem cells derived from cord blood or bone marrow.

Under separate embodiment the invention is further directed to cultured hematopoietic stem cells as a preferred group of cultured cells.

Subgroup of Multipotent Cultured Cells

The present invention is especially directed to cultured multipotent cells and cell populations. The preferred multipotent cultured cell means various multipotent cell populations enriched in cell cultures. The inventors were able to reveal special characteristics of the stem cell type cell populations grown artificially. The multipotent cells according to the invention are preferably human stem cells.

Cultured Mesenchymal Stem Cells

The present invention is especially directed to mesenchymal stem cells. The most preferred types of mesenchymal stem cells are derived from blood related tissues, referred as "blood-related mesenchymal cells", most preferably human blood or blood forming tissue, most preferably from human cord blood or human bone marrow or in a separate embodiment are derived from embryonal type cells. Mesenchymal stem cells derived from cord blood and from bone marrow are preferred separately.

Cultured Embryonal-Type Cells and Cell Populations

The inventors were able to reveal specific glycosylation nature of cultured embryonal-type cells according to the invention. The present invention is specifically directed to various embryonal type cells as preferred cultivated cells with regard to the present invention.

Early Blood Cell Populations and Corresponding Mesenchymal Stem Cells

Cord Blood

The early blood cell populations include blood cell materials enriched with multipotent cells. The preferred early blood cell populations include peripheral blood cells enriched with regard to multipotent cells, bone marrow blood cells, and cord blood cells. In a preferred embodiment the present invention is directed to mesenchymal stem cells derived from early blood or early blood derived cell populations, preferably to the analysis of the cell populations.

Bone Marrow

Another separately preferred group of early blood cells is bone marrow blood cells. These cells do also comprise multipotent cells. In a preferred embodiment the present invention is directed to mesenchymal stem cells derived from bone marrow cell populations, preferably to the analysis of the cell populations.

Preferred Subpopulations of Early Human Blood Cells

The present invention is specifically directed to subpopulations of early human cells. In a preferred embodiment the subpopulations are produced by selection by an antibody and in another embodiment by cell culture favouring a specific cell type. In a preferred embodiment the cells are produced by an antibody selection method preferably from early blood cells. Preferably the early human blood cells are cord blood cells.

The CD34 positive cell population is relatively large and heterogenous. It is not optimal for several applications aiming to produce specific cell products. The present invention is preferably directed to specifically selected non-CD34 populations meaning cells not selected for binding to the CD34-marker, called homogenous cell populations. The homogenous cell populations may be of smaller size mononuclear cell populations for example with size corresponding to CD133+ cell populations and being smaller than specifically selected CD34+ cell populations. It is further realized that preferred homogenous subpopulations of early human cells may be larger than CD34+ cell populations.

The homogenous cell population may a subpopulation of CD34+ cell population, in preferred embodiment it is specifically a CD133+ cell population or CD133-type cell population. The "CD133-type cell populations" according to the invention are similar to the CD133+ cell populations, but preferably selected with regard to another marker than CD133. The marker is preferably a CD133-coexpressed marker. In a preferred embodiment the invention is directed to CD133+ cell population or CD133+ subpopulation as CD133-type cell populations. It is realized that the preferred homogeneous cell populations further includes other cell populations than which can be defined as special CD133-type cells.

Preferably the homogenous cell populations are selected by binding a specific binder to a cell surface marker of the cell population. In a preferred embodiment the homogenous cells are selected by a cell surface marker having lower correlation with CD34-marker and higher correlation with CD133 on cell surfaces. Preferred cell surface markers include α3-sialylated structures according to the present invention enriched in CD133-type cells. Pure, preferably complete, CD133+ cell populations are preferred for the analysis according to the present invention.

The present invention is directed to essential mRNA-expression markers, which would allow analysis or recognition of the cell populations from pure cord blood derived material. The present invention is specifically directed to markers specifically expressed on early human cord blood cells.

The present invention is in a preferred embodiment directed to native cells, meaning non-genetically modified cells. Genetic modifications are known to alter cells and background from modified cells. The present invention is further directed in a preferred embodiment to fresh non-cultivated cells.

The invention is directed to use of the markers for analysis of cells of special differentiation capacity, the cells being preferably human blood cells or more preferably human cord blood cells.

Preferred Purities of the Cell Populations

The preferred purity depends of the affinity of the antibody used. For purification using commercial CD34-antibody preferred purity of complete cell population is at least 90%, more preferably at least 93%, and most preferably at least 95%. In a purification process according to invention by anti-CD133 antibody preferred purity of complete cell population is at least 90%, more preferably at least 93%, and most preferably at least 95%.

The present invention is directed to complete cell populations from human early blood with purity of at least at least 85%, more preferably at least 90%, even more preferably with increasing preference 91%, 92%, 93%, 94%, 95% respectively and most preferably with increasing preference at least 95%, 96%, 97% or 98%. In a specific embodiment the present invention is directed to ultrapure complete cell population in which the level of impurities is less than 10%, more preferably less than 5% and most preferably less than 3%. The innovation is specifically directed to complete cell populations purified by anti CD34 and anti-CD133 antibodies.

In a specific embodiment the present invention is directed to highly purified human complete CD133+ and CD 34+ cell populations derived from cord blood.

Preferred Cord Blood Cell Populations and Characteristics
Cord Blood Cell Populations Preferred cord blood cell populations according to the invention include total mononuclear cells and subpopulations thereof from cord blood. The present invention is further directed to enriched multipotent cells from cord blood. In a preferred embodiment the enriched cells are CD133+ cells, Lin– (lineage negative) cells, or CD34+ cells from cord blood, even more preferably the enriched cells are CD133+ cells, or Lin– (lineage negative) cells.

In a preferred embodiment the present invention is directed to mesenchymal stem cells derived from cord blood or cord blood derived cell populations and analysis thereof according to the invention. A preferred group of mesenchymal stem cells derived from cord blood is mesenchymal stem cells differentiating into cells forming soft tissues such as adipose tissue.

Preferred Purity of Reproducibly Highly Purified Mononuclear Complete Cell Populations from Human Cord Blood The present invention is specifically directed to production of purified cell populations from human cord blood. As described above, production of highly purified complete cell preparations from human cord blood has been a problem in the field. In the broadest embodiment the invention is directed to biological equivalents of human cord blood according to the invention, when these would comprise similar markers and which would yield similar cell populations when separated similarly as the CD133+ cell population and equivalents according to the invention or when cells equivalent to the cord blood is contained in a sample further comprising other cell types. It is realized that characteristics similar to the cord blood can be at least partially present before the birth of a human. The inventors found out that it is possible to produce highly purified cell populations from early human cells with purity useful for exact analysis of sialylated glycans and related markers.

Preferred Bone Marrow Cells

The present invention is directed to multipotent cell populations or early human blood cells from human bone marrow. Most preferred are bone marrow derived mesenchymal stem cells. In a preferred embodiment the invention is directed to mesenchymal stem cells differentiating to cells of structural support function such as bone and/or cartilage.

Embryonal-Type Cell Populations

The present invention is specifically directed to methods directed to embryonal-type cell populations, preferably when the use does not involve commercial or industrial use of human embryos nor involve destruction of human embryos. The invention is under a specific embodiment directed to use of embryonal cells and embryo derived materials such as embryonal stem cells, whenever or wherever it is legally acceptable. It is realized that the legislation varies between countries and regions.

The present invention is further directed to use of embryonal-related, discarded or spontaneously damaged material, which would not be viable as human embryo and cannot be considered as a human embryo. In yet another embodiment the present invention is directed to use of accidentally damaged embryonal material, which would not be viable as human embryo and cannot be considered as human embryo.

It is further realized that early human blood derived from human cord or placenta after birth and removal of the cord during normal delivery process is ethically uncontroversial discarded material, forming no part of human being.

The invention is further directed to cell materials equivalent to the cell materials according to the invention. It is further realized that functionally and even biologically similar cells may be obtained by artificial methods including cloning technologies.

Mesenchymal Multipotent Cells

The present invention is further directed to mesenchymal stem cells or multipotent cells as preferred cell population according to the invention. The preferred mesenchymal stem cells include cells derived from early human cells, preferably human cord blood or from human bone marrow. In a preferred embodiment the invention is directed to mesenchymal stem cells differentiating to cells of structural support function such as bone and/or cartilage, or to cells forming soft tissues such as adipose tissue.

Most Preferred Cell Populations to be Analysed with Regard to Specific Sialylated Structures
NeuGc-Structures Human has been considered to lack NeuGc. Minor amounts of the monosaccharide have been considered to be incorporated to human tissues, when the individual consumes high amounts of NeuGc from food. Certain cultured cell lines may also incorporate the monosaccharide from culture media.

For the first time the inventors were able to define novel structural components representing the NeuGc on the cells according to the invention. The novel structures with NeuGc include especially N-linked glycans and glycolipids.

Preferred NeuGc Comprising Cell Populations

NeuGc-Structures in Early Human Blood Preparations

The present invention is further preferably directed to the analysis of cell populations from early human blood with regard to unusual sialylated structures, preferably NeuGc. The structure has been reported from certain cultured cell lines, but unexpectedly the structure was revealed from fresh cell preparations which had not been cultured in the presence of NeuGc.

More preferably the present invention is directed to the analysis of cord blood cells. The inventors found surprisingly that preparations of cell populations from this material may contain unusual sialylated structures, especially NeuGc. For the first time the inventors were able to define novel structural components representing the NeuGc on the early human blood cells. The novel structures with NeuGc include especially N-linked glycans and glycolipids.

The presence of NeuGc on the specific N-glycans or certain glycolipids was controlled from normal peripheral leukocytes and total population of mononuclear cells from cord blood and was not observed to be present. This indicates specific enrichment of the structures in early human blood cell populations, especially cord blood cell preparations.

NeuGc-Structures in Embryonal Type Cell Populations

Under a separate embodiment the present invention is directed to the analysis of sialylated glycans of embryonal-type cell populations. Similar cells produced in USA and reported as human embryonal stem cell lines have been reported to be contaminated with N-glycolylneuraminic acid (NeuGc) and amounts of both NeuGc and N-acetylneuraminic acid (NeuAc) in these cells have been quantitated. The scientists further discussed cell culture materials containing NeuGc and causing contamination of the cultivated cell lines. The studies did not identify the specific structures to which NeuGc was linked. It is not clear what kind of NeuGc conjugates were detected by monoclonal antibodies.

The present invention was able to describe specific sialylation status of the embryonal-type cells on structural level. The structural level knowledge of the novel NeuGc structures allow specific methods for the control of the presence of the structures and reduction or removal of the structures from cell materials. The inventors observed specific changes and similarities between different populations of embryonal type cells based on analysis of glycan structures. Preferred glycan structures include protein or lipid linked glycans and protein linked glycans. More preferably protein linked glycans are analysed, and most preferably N-glycans.

NeuGc-Structures in Mesenchymal Stem Cell Populations

The inventors were able to reveal NeuGc-structures in mesenchymal stem cell populations according to the invention. Though NeuGc has been implied from certain cultivated cells, the presence of the non-human structure in the human mesenchymal stem cells and the high amount of NeuGc in mesenchymal stem cells was surprising. The inventors were further able for the first time to define novel structural components representing the NeuGc on the mesenchymal stem cells. The novel structures with NeuGc include especially N-linked glycans and glycolipids.

Specific Methods and Other Embodiments Directed to NeuGc

Determination of the Antigenicity

The knowledge of the presence of NeuGc-structures in early human cell populations allow further studies of human immune responses against the specific structures defined by the invention.

Removal of the NeuGc Structures from the Preferred Cells According to the Invention A. Cell Culture Methods In contrast to what was previously reported for embryonal stem cells, the inventors were able to demonstrate removal of the NeuGc from the cells according to the invention during culture of the cells. The inventors demonstrate that change of media for the cell culture reduced or removed NeuGc structures from the specific cells according to the invention. This demonstrates that the cells are metabolically active in changing sialic acid structures.

The inventors were especially able to demonstrate the removal of the sialic acid from cultured stem cells such as embryonal-type stem cells and mesenchymal stem cells according to the invention by culture in specific low-NeuGc or non-NeuGc cell culture media. The invention is especially directed to the NeuGc removal from the specifically preferred structures according to the invention by the preferred cell culture methods.

Novel Non-NeuGc Culture Media

Culturing cells in human serum containing media instead of media containing serum of animal origin has been implied as a potential method for removal of NeuGc from unspecified structures of embryonal stem cells (Varki et al). It is realized that use of serum from a patient as suggested by Varki and colleagues may not be possible due to condition of the patient. It is further realized that use of human serum involves risks of infections, for example. The present invention is especially directed to animal derived non-NeuGc media, with strongly reduced amount of NeuGc or which is practically depleted from NeuGc. Preferred animal derived non-NeuGc media includes media produced from animal sera such as bovine or horse sera. The preferred production methods are described within the glycan depleted reagents section below.

Novel Low-NeuGc Cell Culture Media

The present invention is especially directed to animal derived low-NeuGc media, with reduced controlled amount of NeuGc. The invention revealed that when the composition of the animal cell culture media is selected to contain low amounts of NeuGc, very low or practically no NeuGc is incorporated to the cultured cells.

The inventors noted that of the glycoproteins used in the culture media, especially bovine transferrin, contained very high amounts of NeuGc. The present invention is especially directed to low-NeuGc media containing low amounts of transferrin and more preferably no added transferrin or no transferrin at all. The inventors were able to identify bovine glycoproteins containing much lower amounts of NeuGc. Preferably bovine glycoproteins to be used in low-NeuGc media include bovine fetuin. The low-NeuGc cell culture media may comprise animal serum, even bovine serum, containing relatively low amounts of NeuGc. The amount of serum is adjusted so that it will not yield undesirably high NeuGc content to cells. It is further realized that in part or totally sialic acid depleted serum or serum proteins as described for glycan depleted reagents (serums and proteins) according to the invention may be used in low-NeuGc culture media.

In a specific embodiment glycoproteins or serum from non-human animals lacking NeuGc are used for preparation of non-NeuGc or low-NeuGc cell culture media, a preferred NeuGc-lacking animal is chicken. Preferably potential antibodies binding to the cells such as anti-NeuGc antibodies in case of low-NeuGc media or media aimed for NeuGc containing cells in a NeuGc removal process are removed from the animal sera aimed for production of the media.

It is realized that that production of non-NeuGc media is a laborious and costly process. Processing steps with serum and especially with various separate glycoproteins increases the risk for contamination of the materials. Furthermore it involves changes in compositions, which affect the viability, differentiation and proliferative and other properties of the cultured cells.

Preferred animal derived low-NeuGc media includes media produced from animal sera or protein components thereof such as bovine or horse sera. The more preferred low-NeuGc media are produced from bovine serum and/or selected bovine low-NeuGc serum proteins.

Combination Process

The present invention is further directed to preferred combination process wherein
1. the cells are cultivated and propagated in low-NeuGc serum,
2. the cells are optionally washed to remove cell associated material
3. before the use biological/other use of the cells the residual NeuGc is removed by culturing the cells in non-NeuGc medium for long enough to remove the residual NeuGc.

The combination process yields cost effectively cells devoid of NeuGc or practically devoid of NeuGc. It is realized that very low concentrations/densities of NeuGc on cell surfaces are not antigenic, because anti-NeuGc antibodies cannot find at least two epitopes which would be required for simultaneous effective binding on cell surface.

Specific Cell Culture Methods to Remove NeuGc from Human Mesenchymal Stem Cells

The present invention is especially directed to cell culture methods for removal of the NeuGc from human cultivated mesenchymal stem cell populations. It was revealed that it is possible to culture human mesenchymal stem cells according to the invention in media reduced or depleted with regard to NeuGc cost effectively.

The invention is specifically directed to culture of human mesenchymal stem cells in media reduced or depleted with regard to NeuGc, preferably in order to avoid incorporation of NeuGc or remove/reduce the amount NeuGc in the cells. The invention is directed to the removal of NeuGc from mesenchymal stem cells according to the invention by culture in animal derived non-NeuGc media or production of mesenchymal stem cells containing low amounts of NeuGc by growing the cells in low-NeuGc media.

Application of NeuGc-Removal and Reduction to all Types of Cells

It is realized that the cell culture methods involving the non-NeuGc media and the low-NeuGc media are applicable to all types of cultured stem cells. In a preferred embodiment the NeuGc-removal method by the media according to the invention are used for any type of cultured cells aimed for therapeutic use or research use in context with molecules unwantedly reacting with NeuGc such as antibodies from human serum.

Controlled Removal of NeuGc During Cell Culture

The present invention is further directed to controlling the reagents aimed for removal of the NeuGc during cell culture, such as non-NeuGc or low-NeuGc media or individual protein components thereof, in order to reveal if the materials or the media mixture are suitable for the uses according to the invention. It is noted that there is individual variations in NeuGc content in animal sera such as bovine sera. This is illustrated by an example showing that the bovine transferrin analysed by the inventors by mass spectrometry and by HPLC-methods has different ratio of NeuAc and NeuGc in comparison to the prior published analysis. The invention is specifically directed to selection of protein/serum batches containing low amount of NeuGc for production of low-NeuGc and/or non-NeuGc media, preferably low-NeuGc media. The inventors further realized that the processes of glycan depletion from proteins or from sera may involve technical or other errors so that these would need to be controlled. The invention is especially directed to mass spectrometric and/or HPLC-analysis for the NeuGc content of the reagents.

B. Enzymatic Removal, Reduction or Replacement of NeuGc

The inventors were able to demonstrate effective enzymatic methods to alter, preferably to remove or to reduce, NeuGc from cells according to the invention. The inventor especially demonstrated for the first time alteration of NeuGc from the preferred novel structures.

The invention is especially directed to alteration of NeuGc enzymatically from fresh preparations from early human blood, most preferably from cord blood preparations and from human mesenchymal stem cells, especially from cord blood and bone marrow derived mesenchymal stem cells. The invention further revealed novel preferred method for removal and/or replacement of NeuGc enzymatically from embryonic stem cells.

The invention is especially directed to the NeuGc alteration from the specifically preferred structures according to the invention by the enzymatic methods.

Neu-O-Ac-Structures

Neu-O-Ac is a novel structure in the cell types according to the invention. The inventors noticed that it can be obtained by the cells as contaminations from cell culture media. The invention is especially directed to early human cells and cell populations comprising Neu-O-Ac and methods directed to reduce Neu-O-Ac in the context of early human cells.

The inventors were able to for the first time define novel structural components representing the Neu-O-Ac on the cells according to the invention. The novel structures with Neu-O-Ac include especially N-linked glycans and glycolipids.

Preferred Cell Types with Neu-O-Ac

Neu-O-Ac-Structures in Early Human Blood Preparations

The present invention is further preferably directed to the analysis of cell populations from early human blood with regard to unusual sialylated structures, preferably Neu-O-Ac.

The inventors were further able for the first time to define novel structural components representing the Neu-O-Ac on the early human blood cell populations. The novel structures with Neu-O-Ac include especially N-linked glycans and glycolipids.

The presence of Neu-O-Ac on the specific N-glycans or certain glycolipids was controlled from normal peripheral leukocytes and total population of mononuclear cells from cord blood and not observed to be present. This indicates specific enrichment of the structures in early human blood cell populations, especially cord blood cell preparations.

Embryonal Type Cells

The inventors realized potential enrichment of Neu-O-Ac on early human cells. It was realized that such enrichment is possible with all types of cells according to the invention including embryonal type cells. Preferred glycan structures include protein or lipid linked glycans and protein linked glycans. More preferably protein linked glycans are analysed, and most preferably N-glycans.

Neu-O-Ac-Structures in Mesenchymal Stem Cell Populations

The inventors were able to reveal Neu-O-Ac-structures in mesenchymal stem cell populations according to the invention. Though Neu-O-Ac has been implied from certain cultured cells, the presence of the non-human structure in the human mesenchymal cells and the high amount of Neu-O-Ac in mesenchymal stem cells was surprising. The inventors were able to further for the first time define novel structural components representing the Neu-O-Ac on the mesenchymal cells. The novel structures with Neu-O-Ac include especially N-linked glycans representing the structures.

Specific Methods and Other Embodiments Directed to Neu-O-Ac

Determination of the Antigenicity

The knowledge of the presence of Neu-O-Ac-structures in early human cell populations allow further studies of human immune responses against the specific structures defined by the invention.

Removal of the Neu-O-Ac Structures from the Preferred Cells According to the Invention A. Cell Culture Methods In contrast to what was previously considered with embryonal stem cells, the inventors were able to demonstrate removal of the Neu-O-Ac from the cells according to the invention during culture of the cells. The inventors demonstrate that change of media for the cell cultivation reduced or removed Neu-O-Ac structures from the specific cells according to the invention. This demonstrates that the cells are metabolically active in changing sialic acid structures.

The inventors were especially able to demonstrate the removal of the sialic acid from embryonal-type stem cells and from mesenchymal stem cells by cell culture according to the invention. The invention is especially directed to the Neu-O-Ac removal from the specifically preferred structures according to the invention by the preferred cell culture methods.

Novel Non-Neu-O-Ac Culture Media

The present invention is especially directed to cell culture media, which does not contain Neu-O-Ac. In preferred embodiment the invention is directed to animal derived non-Neu-O-Ac media, with reduced amount of Neu-O-Ac or, which is practically depleted from Neu-O-Ac.

Preferred animal derived non-Neu-O-Ac media includes media produces from animal sera such as bovine or horse sera. The present invention is especially directed to modified horse serum for cell culture containing altered sialylation, especially reduced or depleted Neu-O-Ac. The preferred production methods are described with glycan depleted reagents section.

The invention is further directed to chemical ester hydrolysis methods to reduce Neu-O-Ac.

Specific Cell Culture Methods to Remove Neu-O-Ac from Human Mesenchymal Stem Cells The present invention is especially directed to cell culture methods for removal of the Neu-O-Ac from human cultured mesenchymal stem cell populations. It was revealed that it is possible to culture human mesenchymal cells according to the invention in media reduced or depleted of Neu-O-Ac.

The invention is specifically directed to cultivations of human mesenchymal stem cells in media reduced or depleted with regard to Neu-O-Ac, preferably in order to avoid incorporation of Neu-O-Ac or remove/reduce the amount Neu-O-Ac in the cells. The inventors were able to demonstrate the removal or reduction of Neu-O-Ac from mesenchymal stem cells according to the invention by animal derived non-Neu-O-Ac media B. Enzymatic Removal, Reduction or Replacement of Neu-O-Ac The inventors were able to demonstrate effective enzymatic methods to alter, preferably to remove or to reduce, Neu-O-Ac from cells according to the invention. The invention especially demonstrated for the first time alteration of Neu-O-Ac levels from the preferred novel structures carrier according to the invention.

The invention is especially directed to alteration of Neu-O-Ac enzymatically in cord blood cell preparations, in embryonal-type cells and in human mesenchymal stem cells.

The invention is especially directed to the Neu-O-Ac alteration from the specifically preferred structures according to the invention by the enzymatic methods.

Preferred NeuAc-Structures with Regard to Specific Cell Populations

Preferred NeuAc Comprising Structures in Early Human Blood Cell Populations

NeuAcα3Galβ4 structures have been previously indicated to be present in human CD34⁺ hematopoietic cells by a specific monoclonal antibody. The present invention is specifically directed to the NeuAcα3Galβ-structures when the structures are not represented by CD34+ cells. The prior art associated specific forms of the structure with hematopoietic CD34+ cell population. The antibody used in generating the prior art has been indicated to bind specifically an unusual glycolipid structure NeuAcα3Galβ4GlcNAcβ3 (NeuAcα3Galβ4GlcNAcβ6)Galβ4GlcβCer. The present invention revealed other types of structures linked to different N-glycan carriers with terminal NeuAcα3Galβ4GlcNAcβ2Man-structures, it is realized that the structures on different carriers are biologically and biosynthetically different molecules. More effective biosynthesis of NeuAcα3Galβ4GlcNAc was implicated in CD133+ cell line, indicating higher specificity than the CD34+ cell line.

The inventors were able to analyse presence of both NeuAcα3 and NeuAcα6-structures and even NeuGcα3/6, and larger sialylated structures including also information about the glycan core structure by which the glycan is linked to the cell from early human cell populations. The present invention is in a preferred embodiment directed to analysis of at least two or several sialylated terminal epitopes or at least one whole glycan structure. In a preferred embodiment sialic acid analysis of early human blood cells is directed to multipotent cell populations, which are not CD34⁺ hematopoietic progenitor cells. Preferably the analysis includes analysis of N-linked glycans.

The inventors were able to find differences between cell populations with regard to expression of the sialylated structures. The analysis of glycan structures showed to be an effective method to analyze different early human cell populations. The present invention is specifically directed to novel mass spectrometric analysis methods.

Preferred Glycan Oligosaccharide Structures

Novel Sialylated Glycans Present in or Enriched in Target Material

The sialylated structures include structures according to the formula I:

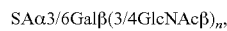

wherein n is either 0 or 1, preferably when the structure is linked to a N-glycan structure or to a glycolipid structure.

Wherein SA is a sialic acid, more preferably NeuAc, NeuGc or O-acetylated form thereof. In a preferred embodiment the SA is in at least part of the structures NeuAc and in another preferred embodiment SA corresponds to in at least part of the structures at least one O-acetylated sialic acid.

Novel Sialylated N-Glycans Present in or Enriched in Target Material

Enriched Sialylated N-Glycan Structures:

The present invention is directed to at least one of natural oligosaccharide sequence structures and structures truncated from the reducing end of the N-glycan according to the Formula:

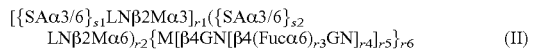

with optionally one or two additional branches according to

wherein r1, r2, r3, r4, r5, r6, and r7 are either 0 or 1,
wherein s1, s2 and s3 are either 0 or 1,
with the proviso that at least r1 is 1 or r2 is 1, and at least one of s1, s2 or s3 is 1.

LN is N-acetylalactosaminyl also marked as GalβGN, GN is GlcNAc, M is mannosyl-, with the proviso LNβ2M or GNβ2M can be further elongated with one or several other monosaccharide residues such as by galactose or LN which may be further substituted by SAα-structures, and/or one LNβ2M can be truncated to Man or GNβ2M
and/or one GNβ2M can be truncated to M,
and/or Mα6 residue and/or Mα3 residues can be further substituted one or two β6-, and/or β4-linked additional branches according to the formula,
and/or Manβ4 can be further substituted by GNβ4,
and/or SA may include natural substituents of sialic acid and/or it may be substituted by other SA-residues preferably by α8- or α9-linkages.

{ }, [ ] and [ ] indicate groups either present or absent in a linear sequence. ( ) indicates branching which may be also present or absent.

The SAα-groups are linked to either 3- or 6-position of neighbouring Gal residue or on 6-position of GlcNAc, preferably 3- or 6-position of neighbouring Gal residue. In separately preferred embodiments the invention is directed structures comprising solely 3-linked SA or 6-linked SA, or mixtures thereof. In a preferred embodiment the invention is directed to glycans wherein r6 is 1 and r5 is 0, corresponding to N-glycans lacking the reducing end GlcNAc structure.

The forms of truncated reducing end are specifically directed for testing and production of reagents for the detection of the cells for the uses according to the invention. The forms truncated at the reducing end are further preferred as degradatively cleaved and released oligosaccharides from the preferred cells especially for analysis of released oligosaccharides from the cells according to the invention, most preferably for mass spectrometric analysis.

Preferred Non-Truncated Forms

The present invention is directed to at least one of natural oligosaccharide sequence structures and structures truncated from the reducing end of the N-glycan according to the Formula:

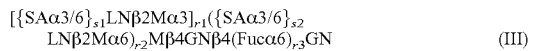

with optionally one or two additional branches according to

wherein the variables and variations are as described for II och IIb
except for the variables of reducing end truncation r4, r5 and r6 which are not present.

The non-truncated forms represent the actual N-glycan markers on cell surfaces of the target materials according to the invention. The N-glycan markers are linked on proteins on cell surface and these are linked to proteins by N-glycosidic linkage to Asn-residue of N-glycosylation sites of the proteins.

The non-truncated forms further represent released oligosaccharide or oligosaccharides produced by chemical and/or enzymatic methods releasing such oligosaccharides, most preferably chemical N-glycan release methods or by enzymatic methods such as protein/peptide N-glycosidase methods.

Novel Sialylated Glycolipids Present in or Enriched in Target Material

The present invention is further directed to novel sialylated glycolipid structures in the target cell populations the preferred glycolipid structures comprise oligosaccharide sequences according to the Formula:

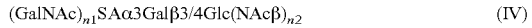

wherein n1 and n2 are either 0 or 1.
The preferred structures further includes

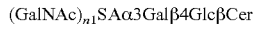

wherein n1 is either 0 or 1.

Glycomes-Oligosaccharide Mixtures Comprising Preferred Structures

Derivatized Glycomes

It is further realized that the glycans may be derivatized chemically during the process of release and isolation. Preferred modifications include modifications of the reducing end and or modifications directed especially to the hydroxyls- and/or N-atoms of the molecules. The reducing end modifications include modification involving known derivatizations reactions of the reducing of reducing glycans, preferably reduction, glycosylamine, glycosylamide, oxime (aminooxy-) and reductive amination modifications. Most preferred modifications include modification of the reducing end. The derivatization of hydroxyl- and/or amine groups, such as produced by methylation or acetylation methods including permethylation and peracetylation has been found especially detrimental to the quantitative relation between natural glycome and the released glycome.

Non-Derivatized Released Glycomes

In a preferred embodiment the invention is directed to non-derivatized released glycomes. The benefit of the non-derivatized glycomes is that less processing needed for the production. The non-derivatized released glycomes correspond more exactly to the natural glycomes from which these are released. The present invention is further directed to quantitative purification according to the invention for the non-derivatized released glycomes and analysis thereof.

The present invention is especially directed to released glycomes when the released glycome is not a permodified glycome such as permethylated glycome or peracetylated glycome. The released glycome is more preferably reducing end derivatized glycome or a non derivatized glycome, most preferably non-derivatized glycome.

Novel Glycomes and Released Glycomes of the Target Material

The present invention is further directed to novel total compositions of glycans or oligosaccharides referred as glycomes and in a more specific embodiment as released glycomes observed from or produced from the target material according to the invention. The released glycome indicates the total released glycans or total specific glycan subfractions released from the target material according to the invention. The present invention is specifically directed to released glycomes meaning oligosaccharides released from the target material according to the invention and to the methods according to the invention directed to the glycomes.

The present invention preferably directed to the glycomes released as truncated and/or non-truncated glycans and/or derivatized according to the invention.

The invention is especially directed to N-linked released glycomes from the target material according to the invention. The invention is more preferably directed to N-linked released glycomes comprising glycan structures according to the invention, preferably glycan structures as defined in formula I, II or III.

Preferred Special Sialic Acid Types
Preferred Enriched Sialic Acid Tape: N-glycolylneuraminic Acid The inventors observed NeuGc on specific glycan structures on the target materials according to the invention. The invention is especially directed to NeuGcα3/6Gal-structures on target material, especially preferred target material comprising NeuGc.

The present invention is further directed to the N-glycan structures according to the invention comprising at least one NeuGc-residue.

The present invention is further directed to the glycolipid structures according to the invention comprising at least one NeuGc-residue.

The present invention is especially directed to preferred N-glycans and N-glycomes comprising NeuGc on the preferred target materials according to the present invention.

Preferred Enriched Sialic Acid Type: O-Acetylated Sialic Acid Neu-O-Ac

The inventors observed Neu-O-Ac on specific glycan structures on the target materials according to the invention. The invention is especially directed to Neu-O-AcαGal-structures on target material, especially preferred target material comprising Neu-O-Ac.

The present invention is further directed to the N-glycan structures according to the invention comprising at least one Neu-O-Ac-residue.

The present invention is especially directed to preferred N-glycans and N-glycomes comprising Neu-O-Ac on the preferred target materials according to the present invention Preferred Mass Spectrometric Methods The present invention is specifically directed to control methods based on the mass spectrometric methods according to the invention. The invention is specifically directed to the control of preferred cell materials by the mass spectrometric glycan analysis methods as described by the invention. These are novel methods and invention reveals the usefulness of the methods for the specific materials. The usefulness of the mass spectrometric analysis for the analysis of the specific reagents to be controlled was also revealed and present invention is preferably directed to the mass spectrometric analysis of the reagents. The invention is specifically directed to the control of preferred cell materials by the mass spectrometric analysis of the preferred sialylated glycan structures as described by the invention.

The invention is specifically directed to mass spectrometric analysis of for presence of the structures according to the invention by method including release of glycans, purification of the glycan fraction, measuring molecular masses; optionally modifying part of glycans by specific sialidase enzymes and analysing the modified glycans; and assigning/fitting the molecular masses of glycans to specific structures according to the invention.

Analysis of Specific Sialic Acid Types and Structures

The invention is further directed to mass spectrometric analysis of presence or absence of NeuGc by analysis of indicative glycan signals, when using rounded exact mass numbers as glycan names, at m/z 1946, m/z 2237, and m/z 2253 or corresponding and additional signal assigned to NeuGc-structures listed in Table 1 and/or Table 6, with optional the provision that when the mass number corresponds also to alternative structures the presence of NeuGc is further verified by other data, preferably mass spectrometric or labelling data.

The invention is further directed to mass spectrometric analysis of presence or absence of Neu-O-Ac is analysed by indicative glycan signals, differentiated from unmodified sialic acids by mass of $C_2H_2O$ functional group residue or corresponding signal(s) assigned to Neu-O-Ac-structures listed in Table 6, with optional the provision that when the mass number corresponds also to alternative structures the presence of Neu-O-Ac is further verified by other data, preferably mass spectrometric fragmentation data or labelling data.

The invention is further directed to mass spectrometric analysis of α3- and/or α6-linked sialic acid by using an enzymatic or chemical reaction revealing the linkage type of the sialic acid. The preferred modification includes cleavage by a sialidase enzyme specifically cleaving α3-linked sialic acid, and optionally a control cleavage by general sialidase enzyme.

The invention is further directed to analysis of specific carrier structures for the preferred silaic acid structures by analysing molecular masses of released glycans as described above.

mRNA Corresponding to Glycosylation Enzymes

The present invention is further directed to correlation of specific messenger mRNA molecules with the preferred glycan structures according to the present invention. It is realized that glycosylation can be controlled in multiple levels and one of them is transcription. The presence of glycosylated structures may in some case correlate with mRNAs involved in the synthesis of the structures.

The present invention is especially directed to analysis of mRNA-species having correlation with expressed sialylated glycan structures preferred according to the present invention. The preferred mRNA-species includes mRNA corresponding to the enzyme cytidine monophospho-N-acetylneuraminic acid hydroxylase (CMAH), which is indicated to be a key enzyme in biosynthesis of NeuGc. The present invention is specifically directed to a novel human form of the mRNA of the CMAH enzyme. The present invention is further directed to mRNA corresponding to sialyltransferase ST3GalVI, which is known to synthesize the structure SAα3Galβ4GlcNAc.

mRNA-Directed Methods
Novel Human mRNA Homologous to Mammalian CMAH-Enzymes

The present invention describes novel variant of human mRNA of the enzyme CMAH. The CMAH enzyme has known to synthesize CMP-NeuGc in non-human animals. In human the enzyme has been considered to be inactive. Interestingly the human enzyme appears to be highly conserved indicating potential function. The invention describes in examples 7 and 8 the expression and cloning of the novel human mRNA. Similar protein sequence has been suggested from a genomics work but its actual expression or the expression according to the invention has not been known, previously the human sequence has been considered as the shorter variant described by Irie and colleagues.

The results from qRT-PCR analysis reveal that the mRNA is expressed in stem cell populations and cell populations containing stem cells, while control cells were not expressing it. The cell populations with expression include cord blood cells and corresponding mesenchymal stem cells, bone marrow cells and corresponding mesenchymal stem cells and embryonal stem cell lines. Especially specific expression was observed with Lin− cells in contrast to Lin+ cells with no observable expression. The highest expression was observed in CD133+ cells.

The invention is preferably directed to human CMAH mRNA and especially to the novel CMAH mRNA as a marker for human stem cells, more preferably early human blood cells and corresponding mesenchymal cells.

The invention is further directed to the CMAH mRNAs as a marker of human cord blood mononuclear cells and as a human mesenchymal stem cell marker due to high expression levels.

The present invention is specifically directed to the novel human mRNA as a substance as described in the experimental section. The invention is further directed to hogenous mRNAs with very similar sequences such as 99% similar mRNA. It is further realized that different mRNAs can be produced for production of the same or very highly similar protein such as a protein with about 99.5% or 99.8% similarity, and the present invention is specifically directed to the mRNAs, especially when these are produced from mRNAs at least 90% similar, more preferably at least 98% similar to the novel mRNA according to the invention.

The expression of CMAH expression was observed in context of cell types observed to able to contain NeuGc-monosaccharide. The ability contain NeuGc seem to be specific for limited cell types.

The present invention is specifically directed to the analysis the human CMAH mRNA expression, especially novel human CMAH mRNA expression, from cells with ability for CMAH expression.

Methods Directed Specifically to Novel Human CMAH-Enzyme

The invention revealed that the novel form of human CMAH enzyme widely expressed in the preferred cells is substantially longer that the alternative mRNA previously described from human HeLA cells. It is realized that the difference can be used for studies of expression of different forms of the mRNA and presence of potential predicted protein.

The present invention is especially directed to the C-terminal 25 amino acid sequence by which the novel predicted protein especially differs from the earlier human predicted protein, and more preferably to the 20 amino acid comprising C-terminal sequence by which the novel predicted protein is longer than the previous human protein, and the mRNA sequences of 60 and 75 base pairs of the novel mRNA corresponding to the preferred protein sequences. The invention is further directed to all sequences of consecutive amino acids of preferably of at least 3 or 4 amino acids derived from the preferred amino acid sequences of 25 and 20 amino acids, and further more corresponding shorter mRNA sequences. The invention is further directed to the preferred amino acid and mRNA sequences in combination with other parts of Human CMAH mRNA sequence.

The amino acid sequences are preferred for the production of peptide directed antibodies as known in the art, and the mRNA sequences are preferred for producing nucleotide probes capable of hydridizing with the novel mRNA. The antibodies and mRNA probes are further preferred for the analysis of the expression of the novel human mRNA and analysis of potential expression or non-expression of the predicted protein sequence.

The invention is further directed to the PCR-methods and qRT-PCR-methods for recognition of the novel part of CMAH mRNA sequence according to the invention.

Control of Cell Status and Potential Contaminations by Glycosylation Analysis

Contaminations with Harmful Glycans Such as Antigenic Animal Type Glycans

Several glycans structures contaminating cell products may weaken the biological activity of the product.

The harmful glycans can affect the viability during handling of cells, or viability and/or desired bioactivity and/or safety in therapeutic use of cells.

The harmful glycan structures may reduce the in vitro or in vivo viability of the cells by causing or increasing binding of destructive lectins or antibodies to the cells. Such protein material may be included e.g. in protein preparations used in cell handling materials. Carbohydrate targeting lectins are also present on human tissues and cells, especially in blood and endothelial surfaces. Carbohydrate binding antibodies in human blood can activate complement and cause other immune responses in vivo. Furthermore immune defence lectins in blood or leukocytes may direct immune defence against unusual glycan structures.

Additionally harmful glycans may cause harmful aggregation of cells in vivo or in vitro. The glycans may cause unwanted changes in developmental status of cells by aggregation and/or changes in cell surface lectin mediated biological regulation.

Additional problems include allergenic nature of harmful glycans and misdirected targeting of cells by endothelia/cellular carbohydrate receptors in vivo.

Contamination/Harmful Effect Due to Nature of Raw Material for Producing a Cell Population Species specific, tissue specific, and individual specific differences in glycan structures are known. The difference between the origin of the cell material and the potential recipient of transplanted material may cause for example immunologic or allergic problems due to glycosylation differences. It is further noticed that culture of cells may cause changes in glycosylation. When considering human derived cell materials according to the present invention, individual specific differences in glycosylation are a potential source of harmful effects.

Control of Raw Material Cell Population

The present invention is directed to control of glycosylation of cell populations to be used in therapy.

The present invention is specifically directed to control of glycosylation of cell materials, preferably when 1) There is difference between the origin of the cell material and the potential recipient of transplanted material. In a preferred embodiment there are potential inter-individual specific differences between the donor of cell material and the recipient of the cell material. In a preferred embodiment the invention is directed to animal or human, more preferably human specific, individual person specific glycosylation differences. The individual specific differences are preferably present in mononuclear cell populations of early human cells, early human blood cells and embryonal type cells. The invention is preferably not directed to observation of known individual specific differences such as blood group antigens changes on erythrocytes.

2) There is possibility in variation due to disease specific variation in the materials. The present invention is specifically directed to search of glycosylation differences in the early cell populations according to the present invention associated with infectious disease, inflammatory disease, or malignant disease. Part of the inventors have analysed numerous cancers and tumors and observed similar types of glycosylations as certain glycosylation types in the early cells.

3) There is for a possibility of specific inter-individual biological differences in the animals, preferably humans, from which the cells are derived for example in relation to species, strain, population, isolated population, or race specific differences in the cell materials.

Contaminations from Reagents

The present invention is specifically directed to control of the reagents used to prevent contamination by harmful glycan structures. The harmful glycan structures may originate from reagents used during cell handling processes such as cell preservation, cell preparation, and cell culture.

Preferred reagents to be controlled according to the present invention include cell blocking reagents, such as antibody receptor blocking reagents, washing solutions during cell processing, material blocking reagents, such as blocking reagents for materials like for example magnetic beads. Preferably the materials are controlled:

1. so that these would not contain a contaminating structure, preferably a NeuGc-structure according to the invention, or more specifically preferred glycan structure according to the invention
2. so that the materials contain very low amounts or do not contain any potentially harmful structures according to the invention.

Contaminations Due to Process Conditions—
Conditions and Reagents Inducing Harmful Glycosylation or Harmful Glycosylation Related Effects to Cells During Cell Handling The inventors further revealed conditions and reagents inducing harmful glycans to be expressed by cells with same associated problems as the contaminating glycans. The inventors found out that several reagents used in a regular cell purification process caused changes in early human cell materials.

It is realized that the materials during cell handling may affect the glycosylation of cell materials. This may be based on the adhesion, adsorption, or metabolic accumulation of the structure in cells under processing.

In a preferred embodiment the cell handling reagents are tested with regard to the presence of NeuGc or a preferred NeuGc structure according to the invention. The testing is especially preferred for human early cell populations and preferred subpopulations thereof.

The inventors note effects of various effector molecules in cell culture on the glycans expressed by the cells if absorption or metabolic transfer of the carbohydrate structures have not been performed. The effectors typically mediate a signal to cell for example through binding a cell surface receptor.

The effector molecules include various cytokines, growth factors, and their signalling molecules and co-receptors. The effector molecules may be also carbohydrates or carbohydrate binding proteins such as lectins.

Controlled Cell Isolation/Purification and Culture Conditions to Avoid Contaminations with Harmful Glycans
Controlled Cell Preparation (Isolation or Purification)

The inventors analysed process steps of common cell preparation methods. Multiple sources of potential contamination by animal materials were discovered.

The present invention is specifically directed to carbohydrate analysis methods to control of cell preparation processes. The present invention is specifically directed to the process of controlling the potential contaminations with animal type glycans, preferably N-glycolylneuraminic acid at various steps of the process.

The invention is further directed to specific glycan controlled reagents to be used in cell isolation The glycan-controlled reagents may be controlled on three levels:

1. Reagents controlled not to contain observable levels of harmful glycan structure, preferably N-glycolylneuraminic acid or structures related to it
2. Reagents controlled not to contain observable levels of glycan structures similar to the ones in the cell preparation
3. Reagent controlled not to contain observable levels of any glycan structures.

The control levels 2 and 3 are useful especially when cell status is controlled by glycan analysis and/or profiling methods. In case reagents in cell preparation would contain the indicated glycan structures this would make the control more difficult or prevent it. It is further noticed that glycan structures may represent biological activity modifying the cell status.

Preferred Glycan Controlled Reagents and Processes for Preparation Thereof

Preferred reagents to be controlled include preferably all reagents derived from or produced in connection with biological material; preferably these include all glycoprotein, protein mixture, serum, and albumin preparations present in the process. The inventors found out that albumins known to be non-glycosylated proteins may still contain sufficient glycoproteins for contamination of cell material.

In a preferred embodiment the present invention is directed to the control of animal albumins, preferably bovine serum albumin, and human serum albumin preparations for potential contamination by glycan structures.

Other preferred controlled reagents includes controlled transferrin and other serum proteins, even more preferably controlled serum proteins are controlled antibody preparations, preferably Fc blocking antibody preparations.

In yet another embodiment the invention is directed to the production of glycan depleted and/or remodeled protein mixtures preferably glycan remodeled human or animal serum, more preferably a serum from an animal used for production of serum products, preferably cell culture serum or antibodies. Preferred serums to be modified includes serum of cow, horse, sheep, goat, rabbit, rat or mouse, more preferably serum of cow, horse, or sheep, even more preferably fetal bovine serum.

In a preferred embodiment the glycosylation of the serum is altered by a method based on animals with genetically altered glycan production preferably obtained by a) genetic manipulation of the animal or b) breeding a natural or selecting a natural variant of the production animal to used for serum production, preferably the genetic alteration is directed to tissues producing serum proteins.

Controlled Enzyme Preparations for Products Aimed for Use with Transplantable Cells The present invention is directed under specific embodiment to methods for removal of non-desired carbohydrate structures from living cells. The enzyme proteins are usually antigenic, especially when these are from non-mammalian origin, such as bacteria and/or plants. If the material is not of human origin its glycosylation likely increases the antigenicity of the material. This is particularity the case when the glycosylation has large differences with human glycosylation, preferred examples of largely different glycosylations include: procaryotic glycosylation, plant type glycosylation, yeast or fungal glycosylation, mammalian/animal glycosylation with Galα3Galβ4GlcNAc-structures, animal glycosylation with NeuGc structures. The glycosylation of a recombinant enzyme depends on the glycosylation of the production cell line, these produce partially non-physiological glycan structures in most cases.

Preferred Classes of Controlled Reagents

1. Glycan Depleted Biological Materials, Preferably Glycoprotein Materials

Present invention is specifically directed to use biological materials, preferably glycoprotein material, from which harmful structure is removed or reduced in amount. Glycoproteins are major source of bioactive glycans, in some material presence of glycolipids may be also possible and could be handled similarly. In case the lipid part of glycolipid binds it to the material, released glycan or part of it is water soluble and can be separated. The invention is further directed to glycan depletion methods. In a preferred embodiment the invention is directed to methods including steps of releasing glycan structure and removing released glycan structure.

Preferred methods for removal of the released glycan structure include filtration methods. The filtration methods are based on size difference of the released glycan structure and the glycan depleted protein. A preferred method for removal of the released glycans includes precipitation methods, in a preferred embodiment the invention is directed to precipitation of the protein under conditions where the released glycan structure is soluble.

The glycan depletion may be combined with a step of inactivation of potential harmful proteins such as lectins or antibodies possibly involved in the process. Some reagents such serum in certain cell culture processes may be heat inactivated. The inactivation may be partial. The partial inactivation is in a preferred embodiment performed by releasing glycans inhibiting the harmful binding proteins to the reagent and further to cell involving process. In a preferred embodiment the depleted glycan and the binding protein inhibiting glycan is the same structure. Preferably the released glycans are used when these can not be incorporated to cells to cause further problems in the cell related process. The method of released glycans is not preferred for NeuGc under conditions where it can be incorporated to cells.

Terminally depleted glycans. In a preferred embodiment one or several terminal structures are depleted from a biological material, preferably glycoprotein material. The preferred methods to deplete terminal structures include enzymatic and chemical methods. Preferred enzymatic method is hydrolysis by a glycosidase enzyme or by a trans-glycosylating enzyme capable of removing the terminal structure. Terminal depletion may further include release of several terminal monosaccharide units for example by glycosidase enzymes. Preferred chemical hydrolysis is an acid hydrolysis, preferably a mild acid hydrolysis under conditions not destroying protein structure or from which the protein structure can be restored or renatured. The structure to be depleted is in a preferred embodiment a sialic acid. The sialic acid is preferably released by a sialidase enzyme or by mild acid hydrolysis.

Internally depleted glycans. The present invention is further directed to internal depletion of glycan material by release of glycans from subterminal linkages by chemical and/or enzymatic methods. Methods to release glycans chemically include base hydrolysis methods such as beta elimination for release of O-linked glycans, hydrazinolysis methods to release O-glycans and N-glycans, oxidative methods such as Smith degradation and ozonolysis (preferred for glycolipids). Preferred enzymatic methods includes use of endo-glycosidases such as endoglycosylceramidase for glycolipids, N-glycosidases for N-glycans, and O-glycosidases for O-glycans.

2. Glycosylated Reagents from Non-Animal Sources

In a preferred embodiment the present invention is directed to the use of reagents from non-animal sources devoid of potentially harmful reagents. Preferred non-animal glycosylated proteins are proteins from yeasts and fungi and from plants. It is notable that even these materials contain glycans, which may have harmful allergenic activities or which may cause problems in analysis of human type glycans. Preferably the invention is further directed to control of the glycosylated reagents from non-animal structures, too. Preferred plant derived proteins include recombinant albumins produced by plant cell culture, more preferably non-glycosylated human serum albumins and bovine serum albumins and recombinant gelatin materials such as collagens produced by plant cell systems. The present invention is specifically directed to the processes according to present invention, when a material containing glycans or harmful glycans according to the present invention is replaced by a reagent, preferably a controlled reagent from non-animal sources.

3. Non Glycosylated Reagents from Procaryotes

Many bacterial recombinant proteins are known for lacking expression of glycans. Present invention is directed to control of glycosylation of bacterial protein, as this happens on certain proteins. The present invention is specifically directed to the processes, when a material containing glycans or harmful glycans according to the present invention is replaced by a reagent, preferably a controlled reagent from procaryotes.

Under specific embodiment the present invention is directed to use of glycan controlled forms of glycosidase enzymes for modification of transplantable cells according to the invention and removal of the enzymes from reactions as described by the present invention The present invention is also specifically directed to the glycan controlled enzyme preparations, especially when produced in a mammalian cell line/cultivation process and controlled with regard to Galα3Galβ4GlcNAc-structures, animal glycosylations with NeuGc structures. The preferred enzymes are of human origin, more preferably recombinant enzymes. Most preferably a human serum form of the enzyme is selected and the glycosylation is controlled to be a non-antigenic human-type glycosylation, preferably similar to the glycosylation human natural soluble enzyme.

Glycans Remodeled by Glycosyltransferases/Glycosyltransfer

The present invention is further directed to special glycan controlled reagent produced by process including steps
1) Optionally partially depleting glycan structure as described by the invention, the partially depleted glycan structure may be also a non-animal structure as described for group 2 of glycan depleted reagents or a glycosylated protein from a prokaryote.
2) Transferring an acceptable or non-harmful glycan to glycan of reagent. Such process is known as glycoprotein remodelling for certain therapeutic proteins. The inventors revealed that there is a need for a remodelling process for specific reagents present in cell culture processes.
   Furthermore the inventors were able to show glycan depletion and/or remodelling of large protein mixtures even for total serum involving numerous factors potentially inhibiting transfer reactions.

Cell Preparation Methods Including Glycan-Controlled Reagents

The present invention is further directed to specific cell purification methods including glycan-controlled reagents.

Preferred Controlled Cell Purification Process

The present invention is especially directed to controlled production of human early cells containing one or several following steps. It was realized that on each step using regular reagents in following process there is risk of contamination by extraneous glycan material. The process is directed to the use of controlled reagents and materials according to the invention in the steps of the process.

Preferred purification of cells includes at least one of the steps including the use of controlled reagent, more preferably at least two steps are included, more preferably at least 3 steps and most preferably at least steps 1, 2, 3, 4, and 6.

1. Washing cell material with controlled reagent.
2. When antibody based process is used cell material is in a preferred embodiment blocked with controlled Fc-receptor blocking reagent. It is further realized that part of glycosylation may be needed in a antibody preparation, in a preferred embodiment a terminally depleted glycan is used.
3. Contacting cells with immobilized cell binder material including controlled blocking material and controlled cell binder material. In a more preferred the cell binder material comprises magnetic beads and controlled gelatin material according the invention. In a preferred embodiment the cell binder material is controlled, preferably a cell binder antibody material is controlled. Otherwise the cell binder antibodies may contain even N-glycolylneuraminic acid, especially when the antibody is produced by a cell line producing N-glycolylneuraminic acid and contaminate the product.
4. Washing immobilized cells with controlled protein preparation or non-protein preparation.
   In a preferred process magnetic beads are washed with controlled protein preparation, more preferably with controlled albumin preparation.
5. Optional release of cells from immobilization.
6. Washing purified cells with controlled protein preparation or non-protein preparation.

In a preferred embodiment the preferred process is a method using immunomagnetic beads for purification of early human cells, preferably purification of cord blood cells.

The present invention is further directed to cell purification kit, preferably an immunomagnetic cell purification kit comprising at least one controlled reagent, more preferably at least two controlled reagents, even more preferably three controlled reagents, even preferably four reagents and most preferably the preferred controlled reagents are selected from the group: albumin, gelatin, antibody for cell purification and Fc-receptor blocking reagent, which may be an antibody.

Control of Cell Status

Time Dependent Changes During Cultivation of Cells

Furthermore during long term cultivation of cells spontaneous mutations may be caused in cultivated cell materials. It is noted that mutations in cultivated cell lines often cause harmful defects on glycosylation level.

It is further noticed that cultivation of cells may cause changes in glycosylation. It is realized that minor changes in any parameter of cell cultivation including quality and concentrations of various biological, organic and inorganic molecules, any physical condition such as temperature, cell density, or level of mixing may cause difference in cell materials and glycosylation. The present invention is directed to monitoring glycosylation changes according to the present invention in order to observe change of cell status caused by any cell culture parameter affecting the cells.

The present invention is in a preferred embodiment directed to analysis of glycosylation changes when the density of cells is altered. The inventors noticed that this has a major impact of the glycosylation during cell culture.

It is further realized that if there is limitations in genetic or differentiation stability of cells, these would in crease probability for changes in glycan structures. Cell populations in early stage of differentiation have potential to produce different cell populations. The present inventors were able to discover glycosylation changes in early human cell populations.

Differentiation of Cell Lines

The present invention is specifically directed to observe glycosylation changes according to the present invention when differentiation of a cell line is observed. In a preferred embodiment the invention is directed methods for observation of differentiation from early human cell or another preferred cell type according to the present invention to non-hematopoietic cell types, preferably in mesodermal type of stem cells.

In case there is heterogeneity in cell material this may cause observable changes or harmful effects in glycosylation.

Furthermore, the changes in carbohydrate structures, even non-harmful or functionally unknown, can be used to obtain information about the exact genetic status of the cells.

The present invention is specifically directed to the analysis of changes of glycosylation, preferably changes of sialylation according to the present invention in order to observe changes of cell status during cell cultivation.

Storage Induced Changes Causing Harmful Glycosylations or Change in the Status of Cells It was realized that storage of the cell materials may cause harmful changes in glycosylation or changes in cell status observable by glycosylation analysis according to the present invention.

Changes Observable in Context of Low Temperature Storage or Handling of Cells

The inventors discovered that keeping the cells in lower temperatures alters the status of cells and this observable analysing the chemical structures of cells, preferably the glycosylation of the cells. The lower temperatures usually vary between 0-36 degrees of Celsius including for example incubator temperature below about 36 degrees of Celsius more preferably below 35 degrees of Celsius, various room temperatures, cold room and fridge temperatures typically between 2-10 degrees of Celsius, and temperatures from incubation on ice close to 0 degrees of Celsius typically between 0-4 degrees of Celsius. The lowered temperatures are typically needed for processing of cells or temporary storage of the preferred cells.

The present invention is specifically directed to analysis of the status of cells kept in low temperatures in comparison to natural body temperatures. In a preferred embodiment the control is performed after certain time has passed from process in lower temperature in order to confirm the recovery of the cells from the lower temperature. In another preferred embodiment the present invention is directed to development of lower temperature methods by controlling the chemical structures of cells, preferably by controlling glycosylation according to the present invention.

Changes Observable in Context of Cryopreservation

The inventors discovered that cryopreservation alters the status of cells and this observable analysing the chemical structures of cells, preferably the glycosylation of the cells. The present invention is specifically directed to analysis of the status of cryopreserved cells. In a preferred embodiment the control is performed after certain time has passed from preservation in order to confirm the recovery of the cells from the cryopreservation. In another preferred embodiment the present invention is directed to development of cryopreservation methods by controlling the chemical structures of cells, preferably by controlling glycosylation according to the present invention.

Use of Glycosylation Information

It was realized that any changes or differences in cell status, handling or origin potentially affect carbohydrate structures, can be used to obtain information about exact status of the cells. The information about glycosylation is in many ways useful with regard to cells, for example in relation potential therapeutic uses/usefulness of the cells.

The present invention is specifically directed to the storage of glycosylation information, preferably in a database in a computer system. The present invention is further directed to comparison of old glycosylation data with new data from similar samples.

Ethical Methods Related to Human Embryonal Stem Cells

It is known that current ethical regulation forbid patenting and possibly science or funding thereof with regard to embryonal stem cells in certain countries or regions. The present invention is further directed to all ethically acceptable means for use the technology to support the legally, politically or ethically correct science and/or development and/or law and/or regulation enforcement based on the timely situation in this context in different regions where patenting is active with regard to the present invention.

Use of Data Derived from Embryonal Type Cells
In Comparison with Human Non-Embryonal Stem Cells In a specific embodiment the present invention is directed to the comparison of the glycosylation data, preferably sialylation data according to the present invention, from embryonal type cells with glycosylation data from cell population presenting cell populations similar to human embryonal stem cells, but not being human embryonal stem cells. In a specific embodiment the embryonal type cells are human embryonal stem cells. In more general embodiment the present invention is directed to similar analysis of proteomics and/or mRNA array and/or genomics derived data from embryonal type cells, optionally with glycosylation data analysis according to the invention, and comparison of the data with corresponding data from cell population presenting cell populations similar to human embryonal stem cells, but not being human embryonal stem cells. Preferred combination of the data type used in combination includes any two data types selected from the group mRNA-data, proteomics data and glycosylation data, more preferably glycosylation data is used together with proteomics data or mRNA data, most preferably glycosylation data is used together with proteomics data. The objective of these methods is to verify that a cell line does not represent a human embryonal stem cell line. When the comparison data has been previously derived from embryonal stem cells the method does not involve use of embryo derived material. The method does not harm any embryo, but provides benefit in control of unacceptable use of embryonal material.

In another embodiment the present invention is directed to the comparison of the data preferably glycosylation data from embryonal type cells with data, preferably glycosylation data, from cell population presenting cultivated human embryonal stem cells, when the cell line lacks capability of becoming human embryo, preferably with the provision that only minor part of the cell population is used and the cell line is not able to differentiate to human embryo. As only a minor part of the cell material is used the method does not produce any real damage to the material which no longer represent human embryo. Preferably the analysis is not performed in order to obtain commercial benefit, but to promote ethical, legal, bureaucratic or religious standard with regard to human embryo derived material.

The present invention is directed to commercial technology and products aimed for analysis of cells according to the present invention. It is notable that selling technology, which can be used unethically is not equivalent of performing such a method. The present invention is further directed to methods for analysis of embryonal stem cells and even human embryos in the regions this is considered ethically acceptable. The choice of using the technology for analysis of embryonal stem cells or even human embryos is the choice of the operator doing this.

The inventors were able to discover glycosylation changes in different cell populations. The differences are especially dramatic in human early cells. In preferred embodiment the differences are observed in preferred cell populations according to the invention, preferably in human early cells, and in another preferred embodiment human early blood cells.

Methods to Alter (Remove or Reduce or Change) Glycosylation of Cells

Analysis and Degradative Removal of the Harmful Glycan Structure

The present invention is further directed to degradative removal of specific harmful glycan structures from cell, preferably from desired cell populations according to the invention.

The removal of the glycans or parts thereof occurs preferably by enzymes such as glycosidase enzymes.

In some cases the removal of carbohydrate structure may reveal another harmful structure. In another preferred embodiment the present invention is directed to replacement of the removed structure by less harmful or better tolerated structure more optimal for the desired use.

Desialylation Methods
Preferred Special Target Cell Type

Effective and specific desialylation methods for the specific cell populations were developed. The invention is specifically directed to desialylation methods for modification of human cord blood cells. The cord blood cells are clearly different of other cell types and no desialylation methods have previously been developed for these cells. Due to cell specific differences any quantitative desialylation methods cannot be generalized from one cell population to another. Thus, any results and data demonstrated by other investigators using other cell types are not applicable to cord blood. The present invention is further directed to desialylation modifications of any human stem cell or cord blood cell subpopulation.

The present invention is specifically directed to methods for desialylation of the preferred structures according to the present invention from the surfaces of preferred cells. The present invention is further directed to preferred methods for the quantitative verification of the desialylation by the preferred analysis methods according to the present invention. The present invention is further directed to linkage specific desialylation and analysis of the linkage specific sialylation on the preferred carbohydrate structures using analytical methods according to the present invention.

The invention is preferably directed to linkage specific α3-desialylation of the preferred structures according to the invention without interfering with the other sialylated structures according to the present invention. The invention is further directed to simultaneous desialylation α3- and α6-sialylated structures according to the present invention.

Furthermore the present invention is directed to desialylation when both NeuAc and NeuGc are quantitatively removed from cell surface, preferably from the preferred structures according to the present invention. The present invention is specifically directed to the removal of NeuGc from preferred cell populations, most preferably cord blood and stem cell populations and from the preferred structures according to the present invention. The invention is further directed to preferred methods according to the present invention for verification of removal of NeuGc, preferably quantitative verification and more preferably verification performed by mass spectrometry.

Modification of Cell Surfaces of the Preferred Cells by Glycosyltransferases

The inventors revealed that it is possible to produce controlled cell surface glycosylation modifications on the preferred cells according to the invention. The present invention is specifically directed to glycosyltransferase catalysed modifications of N-linked glycans on the surfaces of cells, preferably blood cells, more preferably leukocytes or stem cells or more preferably the preferred cells according to the present invention.

The present invention is directed to cell modifications by sialyltransferases and fucosyltransferases. Two most preferred transfer reactions according to the invention are α3-modification reactions such as α3-sialylation and α3-fucosylations. When combined these reactions can be used to produce important cell adhesion structures which are sialylated and fucosylated N-acetyllactosamines such as sialyl-Lewis x (sLex).

Sialylation

Possible α6-sialylation has been implied in bone marrow cells and in peripheral blood CD34+ cells released from bone marrow to circulation by growth factor administration, cord blood cells or other stem cell types have not been investigated. Furthermore, the previous study utilized an artificial sialic acid modification method, which may affect the specificity of the sialyltransferase enzyme and, in addition, the actual result of the enzyme reaction is not known as the reaction products were not analysed by the investigators. The reactions are likely to have been very much limited by the specificity of the α6-sialyltransferase used and cannot be considered prior art in respect to the present invention.

The inventors of the present invention further revealed effective modification of the preferred cells according to the present inventions by sialylation, in a preferred embodiment by α3-sialylation.

The prior art data cited above does not indicate the specific modifications according to the present invention to cells from early human blood, preferably cord blood, to cultured mesenchymal stem cells, or to cultured embryonal type cells. The present invention is specifically directed to sialyltransferase reactions towards these cell types. The invention is directed to sialyltransferase catalyzed transfer of a natural sialic acid, preferably NeuAc, NeuGc or Neu-O-Ac, from CMP-sialic acid to target cells.

Sialyltransferase catalyzed reaction according to Formula:

CMP-SA+target cell→SA-target cell+CMP,

Wherein SA is a sialic acid, preferably a natural sialic acid, preferably NeuAc, NeuGc or Neu-O-Ac and
the reaction is catalysed by a sialyltransferase enzyme preferably by an α3-sialyltransferase
and
the target cell is a cultured stem cell or early human blood cell (cord blood cell).

Preferably the sialic acid is transferred to at least one N-glycan structure on the cell surface, preferably to form a preferred sialylated structure according to the invention Fucosyltransferase Reactions In the prior art fucosyltransferase reactions towards unspecified cell surface structures has been studied The prior art indicates that human cord blood cell populations may be α3-fucosylated by human fucosyltransferase VI and such modified cell populations may be directed to bone marrow due to interactions with selectins.

Directing Cells and Selectin Ligands

The present invention describes reactions effectively modifying cord blood cells by fucosyltransferases, especially in order to produce sialylated and fucosylated N-acetyllactosamines on cell surfaces, preferably sLex and related structures. The present invention is further directed to the use of the increased sialylated and/or fucosylated structures on the cell surfaces for targeting the cells, in a preferred embodiment for selectin directed targeting of the cells.

The invention is further directed to α3- and/or α4-fucosylation of cultured stem cells, preferably embryonal stem cells and mesenchymal stem cells derived either from cord blood or bone marrow.

Fucosylation of Human Peripheral Blood Mononuclear Cell Populations

In a specific embodiment the present invention is directed to α3-fucosylation of the total mononuclear cell populations from human peripheral blood. Preferably the modification is directed to at least to one protein linked glycan, more preferably to an N-linked glycan. The prior art reactions reported about cord blood did not describe reactions in such cell populations and the effect of possible reaction cannot be known. The invention is further directed to combined increased α3-sialylation and fucosylation, preferably α3-sialylation of human peripheral blood leukocytes. It is realized that the structures on the peripheral blood leukocytes can be used for targeting the peripheral blood leukocytes, preferably to selecting expressing sites such as selectin expressing malignant tissues.

Methods for Combined Increased α3-Sialylation and α3-Fucosylation

The invention is specifically directed to selection of a cell population from the preferred cell population according to the present invention, when the cell population demonstrate increased amount of α3-sialylation when compared with the baseline cell populations.

The inventors revealed that human cord blood in general is highly α6-sialylated and thus not a good target for α3/4-fucosylation reactions, especially for reactions directed to production of selectin ligand structures.

Use of Selected Cultured α3-Sialic Acid Expressing Cell Populations

The inventors revealed that specific subpopulations of native cord blood cells express increased amounts of α3-linked sialic acid. Preferred selected cell populations from cord blood for α3/4-fucosylation include CD133+ cells.

Furthermore it was found that cultured cells according to the invention have a high tendency to express α3-sialic acid instead to α6-linked sialic acids. The present invention is preferably directed to cultured mesenchymal stem cell lines, more preferably mesenchymal stem cells from bone marrow or from cord blood expressing increased amounts of α3-linked sialic acid Fucosylation of α3-Sialylated Cells The present invention is preferably directed to fucosylation after α3-sialylation of cells, preferably the preferred cells according to the invention. The invention describes for the first time combined reaction by two glycosyltransferases for the production of specific terminal epitopes comprising two different monosaccharide types on cell surfaces.

Fucosylation of Desialylated and α3-Sialylated Cells

The present invention is preferably directed to fucosylation after desialylation and α3-sialylation of cells, preferably the preferred cells according to the invention. The invention describes for the first time combined reaction by two glycosyltransferases and a glycosidase for the production of specific terminal epitopes comprised of two different monosaccharide types on cell surfaces.

Sialylation Methods

Preferred Special Target Cell Type

Early Human Blood

Effective specific sialylation methods for the specific cell populations were developed. The invention is specifically directed to sialylation methods for modification of human cord blood cells and subpopulations thereof and multipotent stem cell lines. The cord blood cells are clearly different from other cell types and no sialylation methods have been developed for the cell population. Due to cell specific differences any quantitative sialylation methods cannot be generalized from one cell population to another. The present invention is further directed to sialylation modifications of any human cord blood cell subpopulation.

Embryonal-Type Cells and Mesenchymal Stem Cells

The methods of present invention are further directed to the methods according to the invention for altering human embryonal-type and mesenchymal stem cells. In a preferred embodiment the modification technologies is directed to cultured cells according to the invention.

Production of Preferred Sialylated Structures

Present invention is specifically directed to methods for sialylation to produce preferred structures according to the present invention from the surfaces of preferred cells. The present invention is specifically directed to production preferred NeuGc- and NeuAc-structures. The invention is directed to production of potentially in vivo harmful structures on cells surfaces, e.g. for control materials with regard to cell labelling. The invention is further directed to production of specific preferred terminal structure types, preferably α3- and α6-sialylated structures, and specifically NeuAc- and NeuGc-structures for studies of biological activities of the cells.

The present invention is further directed to preferred methods for the quantitative verification of the sialylation by the preferred analysis methods according to the present invention. The present invention is further directed to linkage specific sialylation and analysis of the linkage specific sialylation on the preferred carbohydrate structures using analytical methods according to the present invention.

The invention is preferably directed to linkage specific α3-sialylation of the preferred structures according to the invention without interfering with the other sialylated structures according to the present invention. The invention is preferably directed to linkage specific α6-sialylation of the preferred structures according to the invention without interfering with the other sialylated structures according to the present invention.

The invention is further directed to simultaneous sialylation α3- and α6-sialylated structures according to the present invention. The present invention is further directed for the production of preferred relation of α3- and α6-sialylated structures, preferably in single reaction with two sialyl-transferases.

Furthermore the present invention is directed to sialylation when either NeuAc or NeuGc are quantitatively synthesized to the cell surface, preferably on the preferred structures according to the present invention. Furthermore the invention is directed to sialylation when both NeuAc and NeuGc are, preferably quantitatively, transferred to acceptor sites on the cell surface.

The present invention is specifically directed to the removal of NeuGc from preferred cell populations, most preferably cord blood cell populations and from the preferred structures according to the present invention, and resialylation with NeuAc.

The invention is further directed to preferred methods according to the present invention for verification of removal of NeuGc, and resialylation with NeuAc, preferably quantitative verification and more preferably verification performed by mass spectrometry with regard to the preferred structures.

Controlled Cell Modification

The present invention is further directed to cell modification according to the invention, preferably desialylation or sialylation of the cells according to the invention, when the sialidase reagent is a controlled reagent with regard of presence of carbohydrate material.

Purification of Cells with Regard to Modification Enzyme

The preferred processes according to the invention comprise of the step of removal of the enzymes from the cell preparations, preferably the sialyl modification enzymes according to the invention. Most preferably the enzymes are removed from a cell population aimed for therapeutic use. The enzyme proteins are usually antigenic, especially when these are from non-mammalian origin. If the material is not of human origin its glycosylation likely increases the antigenicity of the material. This is particularly the case when the glycosylation has major differences with human glycosylation, preferred examples of largely different glycosylations includes: procaryotic glycosylation, plant type glycosylation, yeast or fungal glycosylation, mammalian/animal glycosylation with Galα3Galβ4GlcNAc-structures, animal glycosylations with NeuGc structures. The glycosylation of a recombinant enzyme depends on the glycosylation in the production cell line, these produce partially non-physiological glycan structures. The enzymes are preferably removed from any cell populations aimed for culture or storage or therapeutic use. The presence of enzymes which have affinity with regard to cell surface may otherwise alter the cells as detectable by carbohydrate binding reagents or mass spectrometric or other analysis according to the invention and cause adverse immunological responses.

Under separate embodiment the cell population is cultured or stored in the presence of the modification enzyme to maintain the change in the cell surface structure, when the cell surface structures are recovering from storage especially at temperatures closer physiological or culture temperatures of the cells. Preferably the cells are then purified from trace amounts of the modification enzyme before use.

The invention is furthermore directed to methods of removal of the modification reagents from cell preparations, preferably the modification reagents are desialylation or resialylation reagents. It is realized that soluble enzymes can be washed from the modified cell populations. Preferably the cell material to be washed is immobilized on a matrix or centrifuged to remove the enzyme, more preferably immobilized on a magnetic bead matrix.

However, extraneous washing causes at least partial destruction of cells and their decreased viability. Furthermore, the enzymes have affinity with regard to the cell surface. Therefore the invention is specifically directed to methods for affinity removal of the enzymes. The preferred method includes a step of contacting the modified cells with an affinity matrix binding the enzyme after modification of the cells.

Under specific embodiment the invention is directed to methods of tagging the enzyme to be removed from the cell population. The tagging step is performed before contacting the enzyme with the cells. The tagging group is designed to bind preferably covalently to the enzyme surface, without reduction or without major reduction of the enzyme activity. The invention is further directed to the removal of the tagged enzyme by binding the tag to a matrix, which can be separated from the cells. Preferably the matrix comprises at least one matrix material selected from the group: polymers, beads, magnetic beads, or solid phase surface Enzymes Acceptable for Humans for Modification of Reagents or Cells Under specific embodiment the invention is directed to the use for modification of the cells according to the invention, or in a separate embodiment reagents for processes according to the invention, of a human acceptable enzyme, preferably sialidase or sialyltransferase, which is acceptable at least in certain amounts to human beings without causing harmful allergic or immune reactions. It is realized that the human acceptable enzymes may not be needed to be removed from reaction mixtures or less washing steps are needed for desirable level of the removal. The human acceptable enzyme is in preferred embodiment a human glycosyltransferase or glycosidase. The present invention is separately directed to human acceptable enzyme which is a sialyltransferase. The present invention is separately directed to human acceptable enzyme which is a sialidase, the invention is more preferably directed to human sialidase which can remove specific type of sialic acid from cells.

In a preferred embodiment the human acceptable enzyme is purified from human material, preferably from human serum, urine or milk. In another preferred embodiment the enzyme is recombinant enzyme corresponding to natural human enzyme. More preferably the enzyme corresponds to human natural enzyme corresponds to natural cell surface or a secreted from of the enzyme, more preferably serum or urine or human milk form of the enzyme. Even more preferably the present invention is directed to human acceptable enzyme which corresponds to a secreted form of a human sialyltransferase or sialidase, more preferably secreted serum/blood form of the human enzyme. In a preferred embodiment the human acceptable enzyme, more preferably recombinant human acceptable enzyme, is a controlled reagent with regard to potential harmful glycan structures, preferably NeuGc-structures according to the invention. The recombinant proteins may contain harmful glycosylation structures and inventors revealed that these kinds of structures are also present on recombinant glycosyltransferases, even on secreted (truncated) recombinant glycosyltransferases.

Quantitative and Qualitative Mass Spectrometric Analysis of Modified Cells and or Reagents The present invention is further directed to the quantitative and qualitative mass spectrometric analysis of modified cells and/or reagents according to the invention.

The invention is directed to production of qualitative glycome analysis of the cell and/or the reagents including determining the monosaccharide composition obtained for the materials.

The present invention is further directed to quantitative mass spectrometric analysis of the materials according to the invention involving determining the intensities of all or part of the mass spectrometric signals verified to be (reasonably) quantitative with regard to the amount of molecules corresponding to the signals, preferably MALDI-TOF mass spectrometric signals.

The invention is further directed to methods, especially research an development methods, such as product development methods, according to the invention for production of reagents or cells as described by the invention involving step of quantitative and/or qualitative glycome analysis, more preferably both quantitative and qualitative analysis.

Methods for Labelling Cells According to the Invention

The present invention is further directed to methods involving binding to the preferred structures on early human cells. The method is based on the use of a specific binding molecule, referred as "binder", which binds a marker structure on surface of a cell population. In a preferred embodiment the present invention is directed to use of a protein binding molecule, more preferably an antibody and most preferably a monoclonal antibody.

Preferred antibodies includes antibodies recognizes a structure NeuGc$\alpha$3Gal$\beta$4Glc(NAc)$_{0\ or\ 1}$ and/or GalNAc$\beta$4 [NeuGc$\alpha$3]Gal$\beta$4Glc(NAc)$_{0\ or\ 1}$, wherein [ ] indicates branch in the structure and ( )$_{0\ or\ 1}$ a structure being either present or absent. In a preferred embodiment the use according to claim 66, wherein the antibody is a monoclonal antibody or human monoclonal antibody.

The present invention is further directed to glycan binding molecules, which recognize glycan marker structures on a cell surface. In a preferred embodiment the binding molecule is a protein, more preferably an enzyme, a lectin or a glycan binding antibody.

Preferred lectins includes the lectin is specific for SA$\alpha$3Gal-structures, preferably being *Maackia amurensis* lectin or the lectin is specific for SA$\alpha$6Gal-structures, preferably being *Sambucus nigra* agglutinin.

The preferred lectins and binding proteins such as antibodies further includes reagents specifically binding to non-human sialic acid (NeuGc and O-acetylated sialic acids), preferably when expressed on N-glycans as described by the invention. In a specifically preferred reagents includes reagents such as proteins (preferably antibodies, lectins, enzymes) binding and recognizing specifically and/or selectively (allowing separation from contaminant present in the cell culture or other cell environment) non-human sialic acid (NeuGc and O-acetylated sialic acids), more preferably O-acetylated sialic acids.

The invention is further directed to search of binding reagents for NeuGc, when the stem cell material according to the invention is not embryonal stem cells and it is preferably differentiated cell derived from embryonal and/or embryonal type stem cells or adult stem cells such as early human cells, or early human blood cells or more preferably blood related stem cells, or cord blood cells or mesenchymal stem cells.

The invention is further directed to development methods, especially research and development methods, such as product development methods, according to the invention for production of reagents or cells as described by the invention involving i) step of testing a binding reagent against a glycan structure according to the invention and ii) a step of testing the binding reagent for binding to the cell material, including non-modified and modified cell material, according to the invention.

The invention is further directed to testing methods for selecting optimal and/or most effective and/or -optimal for a specific cell material-binding reagents from reagents known to have suitable specificity allowing recognition of preferred structures according to the invention. Most preferred reagents to be tested includes antibodies, preferably monoclonal antibodies and lectin recognizing same or similar terminal monosaccharide residues structures, preferably involving potential binding to preferred oligosaccharide (involving a preferred disaccharide or trisaccharide epitope) or glycan sequences according to the invention. The invention is specifically directed to known reagents recognizing non-human sialic acid according to the invention.

In a preferred embodiment the invention is directed to testing of human autoimmunity and/or cancer associated antibodies and or lectins such as Cancer antennarius (EY Laboratories, CA, USA) lectin known to recognize O-acetylated sialic acids. The invention is directed especially to the use of Cancer antennarius (EY-laboratories, CA, USA) lectin to recognize cells according to the invention, whether is a risk of contamination by O-acetylated sialic acids and in context of mesenchymal stem cells. The lectin tested for binding against mesenchymal stem cells derived from human bone marrow by lectin labelling methods described in examples, the results revealed that the lectin can recognize sialyl structures on carrier glycans present on the human meschymal stem cells.

The Binding Methods for Labelling Cells

The present invention is specifically directed to the binding of the structures according to the present invention, when the binder is conjugated with "a label structure". The label structure means a molecule observable in a assay such as for example a fluorescent molecule, a radioactive molecule, a detectable enzyme such as horse radish peroxidase or biotin/streptavidin/avidin. When the labelled binding molecule is contacted with the cells according to the invention, the cells can be monitored, observed and/or sorted based on the presence of the label on the cell surface. Monitoring and observation may occur by regular methods for observing labels such as fluorescence measuring devices, microscopes, scintillation counters and other devices for measuring radioactivity.

Use of Immobilized Binder Structures

In a preferred embodiment the binder structure is conjugated to a solid phase. The cells are contacted with the solid phase, and part of the material is bound to surface. This method may be used to separation of cells and analysis of cell surface structures, or study cell biological changes of cells due to immobilization. In the analytics involving method the cells are preferably tagged with or labelled with a reagent for the detection of the cells bound to the solid phase through a binder structure on the solid phase. The methods preferably further include one or more steps of washing to remove unbound cells.

Preferred solid phases include cell suitable plastic materials used in contacting cells such as cell cultivation bottles, petri dishes and microtiter wells; fermentor surface materials Preferred Cell Population to be Produced According to the Present Invention The present invention is directed to specific cell populations comprising in vitro enzymatically altered sialylation according to the present invention. The preferred cell population includes cells with decreased amount of sialic acids on the cell surfaces, preferably decreased from the preferred structures according to the present invention. The altered cell population contains in a preferred embodiment decreased amounts of α3-linked sialic acids. The present invention is preferably directed to the cell populations when the cell populations are produced by the processes according to the present invention.

Cell Populations with Altered Sialylated Structures

The invention is further directed to novel cell populations produced from the preferred cell populations according to the invention when the cell population comprises altered sialylation as described by the invention. The invention is specifically directed to cell populations comprising decreased sialylation as described by the invention. The invention is specifically directed to cell populations comprising increased sialylation of specific glycan structures as described by the invention. Furthermore invention is specifically directed to cell populations of specifically altered α3- and or α6-sialylation as described by the invention These cells are useful for studies of biological functions of the cell populations and role of sialylated, linkage specifically sialylated and non-sialylated structures in the biological activity of the cells.

Preferred Cell Populations with Decreased Sialylation

The preferred cell population includes cells with decreased amount of sialic acids on the cell surfaces, preferably decreased from the preferred structures according to the present invention. The altered cell population contains in a preferred embodiment decreased amounts of α3-linked sialic or α6-linked sialic acid. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cell, embryonal-type cells or cord blood cell populations according to the invention.

Preferred Cell Populations with Increased Sialylation

The preferred cell population includes cells with increased amount of sialic acids on the cell surfaces, preferably decreased from the preferred structures according to the present invention. The altered cell population contains in preferred embodiments increased amounts of α3-linked sialic or α6-linked sialic acid. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Preferred Cell Populations with Altered Sialylation

The preferred cell population includes cells with altered linkage structures of sialic acids on the cell surfaces, preferably decreased from the preferred structures according to the present invention. The altered cell population contains in a preferred embodiments altered amount of α3-linked sialic and/or α6-linked sialic acid. The invention is specifically directed to cell populations having a sialylation level similar to the original cells but the linkages of structures are altered to α3-linkages and in another embodiment the linkages of structures are altered to α6-structures. In a preferred embodiment the cell populations comprise practically only α3-sialic acid, and in another embodiment only α6-linked sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Cell Populations Comprising Preferred Cell Populations with Preferred Sialic Acid Types The preferred cell population includes cells with altered types of sialic acids on the cell surfaces, preferably on the preferred structures according to the present invention. The altered cell population contains in a preferred embodiment altered amounts of NeuAc and/or NeuGc sialic acid. The invention is specifically directed to cell populations having sialylation levels similar to original cells but the sialic acid structures altered to NeuAc and in another embodiment the sialic acid type structures altered to NeuGc. In a preferred embodiment the cell populations comprise practically only NeuAc, and in another embodiment only NeuGc sialic acids, preferably on the preferred structures according to the invention, most preferably on the preferred N-glycan structures according to the invention. The present invention is preferably directed to the cell populations when the cell populations are produced by the processes according to the present invention. The cell populations with altered sialylation are preferably mesenchymal stem cells or embryonal-type cells or cord blood cell populations according to the invention.

Novel Monoclonal Antibodies for Recognition of NeuGc Structures from Stem Cells

The present invention is directed to novel monoclonal antibodies for recognition of Neu5Gc structures from human cells. The invention revealed that it is possible to recognize Neu5Gc structures by specific monoclonal antibodies. This has clear benefit with regard to known antibodies which are polyclonal mixtures. The polyclonal antibodies are typically produced in animals and the constitution of the antibody mixture would depend on the individual animal, thus providing lower level of reproducibility The invention especially revealed that stem cells contaminated with Neu5Gc can be recognized by specific monoclonal antibodies. The invention is directed to analysis of and binding of stem cells or stem cell culture materials by monoclonal antibodies recognizing Neu5Gc.

It is realized that not all monoclonal antibodies are useful for recognition of NeuGc from stem cells. A commercial mouse monoclonal antibody (code 370650, lot 02301, anti-N-glycolyl GM2, Seikagaku corp., Tokyo/Chemicon International) was tested against stem cells contaminated with NeuGc, but it did not recognize the cell effectively. This antibody has known to recognize mouse liver, erythrocytes and various human cancer tissues (Seikagaku, data sheet). It is realized that the glycan specificity of the antibody, GalNAcβ4(NeuGcα3)LacCer, is not optimal for recognition of NeuGc structures from stem cells especially from pluripotent stem cells or from adult stem cells such as adult stem cells in bone marrow and blood.

The preferred specificity of the antibodies includes binding to structures comprising Neu5Gcα3Galβ4Glc(NAc)-epitope, preferably non-reducing end terminal epitope. Most preferably the antibody is a P3 antibody (Moreno et al., 1998; Vázquez et al., 1995, US2004253233) or a humanized or chimeric version thereof comprising variable domain sequences homologous to P3 antibody and binding to Neu5Gc. The invention is especially directed recognition of presence or absence or level of NeuGc by the monoclonal antibodies in context of stem cells including i) recognition of stem cells or ii) reagents for culture of stem cells, preferred stem cells for the recognition are pluripotent stem cells or from adult stem cells such as adult stem cells in bone marrow and blood, more preferably cord blood cells or/mesenchymal stem cells such as stem cells derived from cord blood.

The invention is further directed to method of evaluating a new antibody with binding to Neu5Gcα3Galβ4Glc(NAc)-epitope to human stem cells.

In a specifically preferred embodiment the present invention is directed to analysis of mesenchymal stem cells, more preferably bone marrow derived stem cells by NeuGc recognizing reagents such as antibodies more preferably monoclonal antibodies.

The invention is further directed to mass spectrometric analysis as shown by invention and examples from stem cells especially from pluripotent stem cells or from adult stem cells such as adult stem cells in bone marrow and blood, more preferably cord blood cells or/mesenchymal stem cells such as stem cells derived from cord blood. In a specifically preferred embodiment the present invention is directed to mass spectrometric Neu5Gc-analysis of mesenchymal stem cells.

Labelling Stem Cells with NeuGc and Polyvalent NeuGc

The invention revealed that it is possible label or target stem cells by NeuGc or conjugates thereof. The invention is especially directed to intracellular labeling or targeting of stem cells and use of the molecules for studying of intracellular localization by the NeuGc-comprising molecules.

The invention is further directed to method of evaluating binding of NeuGc comprising synthetic reagents to stem cells.

The NeuGc comprising conjugates are preferably monosaccharide conjugates and/or polyvalent conjugates, such as polyacrylamide (e.g. from Syntesome/Lectinity, Russia) or other conjugate of preferably water soluble polymer such as polypeptide, polylysine, polyether with branches for (polyvalent conjugates) such as branched polyethylene glycol, dendrimer, or polysaccharide; conjugates comprising terminal NeuGcα-residues, preferably glycosidically linked to an alkyl-spacer comprising at least one —$CH_2$-group, more preferably at least three one —$CH_2$-groups, linked to the polymer carrier by a stabile bond such as an amide bond. The invention is further directed to monovalent or polyvalent conjugates further comprising a detectable label such as a fluorescent label, radiolabel or an enzyme label or a biological effector molecule aimed for effecting cells such as a nucleotide, hormone, cytokine, pharmaceutical molecule or a toxic molecule. Such molecules may be covalently linked to the Neu5Gc-conjugates The invention is further directed to NeuGc-labelling as shown by invention and examples from stem cells especially from pluripotent stem cells or from adult stem cells such as adult stem cells in bone marrow and blood, more preferably cord blood cells or/mesenchymal stem cells such as stem cells derived from cord blood. In a specifically preferred embodiment the present invention is directed to mass spectrometric Neu5Gc-analysis of mesenchymal stem cells.

Removal of NeuGc and Other Non-Human Type Sialic Acids from Biological Proteins Such as Bovine Serum Proteins The present invention revealed novel gentle methods for releasing NeuGc and other non-human type sialic acids from mammalian proteins such as bovine serum proteins. The invention is especially directed to acid hydrolysis methods carried out for elongated time with dilute acids and preferably at modest temperatures such as ones described in examples.

The preferred acid hydrolysis according to the invention is performed by hydrochloric acid or monoprotonated strong acid with similar pKa.

The acid hydrolysis is preferably performed close to 50 degrees of Celsius, preferably between 40 and 70 degrees, more preferably between 40 and 60 degrees of Celsius with HCl concentration of about 50 mM, preferably between about 20-80 mM.

The reaction time is adjusted so that the desired level of desialylation is obtained, longer reaction time is used with more dilute acid and with lower reaction temperature. Preferred reaction time is about 8 hours (6-10 hours) for about 50 mM HCl (60 mM to 40 mM) at about 50 degrees (60 to 40 degrees) of Celsius to obtain about 75-95% desialylation.

The invention is further directed to desialylation of protein by acid hydrolysis so that the protein structure remains essentially intact. The invention is further directed to such proteins when at least 80%, more preferably at least 85% and most preferably at least about 95% of the sialic acids are removed, preferably also the same amount of NeuGc or other non-human type sialic acid is removed. The invention is further directed to products of such reaction when the protein carries multiply sialylated glycans, preferably, disialylated N-glycans and all the disialylated structures are removed and the residual sialic acid is present as monosialylated structures. It is realized that the monosialylated structures have different biological activities that disialylated structures and thus the monosisalylated structures are useful for studies of biological activities of the proteins.

Specific Resialylation of Proteins

The invention is further directed to enzymatic resialylation of the desialylated protein, preferably by α3- and/or by α6-sialyltransferase(s). The invention is specifically directed to (resialylated) bovine serum derived proteins comprising more than 95%, more preferably more than 98% and most preferably more than 99% of NeuNAc. The invention is also directed to reagents with specific resialylation levels, preferably more than 95%, more preferably more than 98% and most preferably more than 99% of NeuNAc. In a preferred embodiment the NeuNAc residues are specifically α3-linked or α6-linked. It is realized that the proteins specifically (re)sialylated with NeuNAc structures (preferably completely α3-resialylated or completely α6-sialylated) have different biological activities that more heterogenous structures and thus the monosisalylated structures are useful for studies of biological activities of the proteins.

The invention is further directed to the synthesis of Neu5Gc-resialylated protein, preferably with specifically α3-linked or α6-linked Neu5Gc, comprising more than 95%, more preferably more than 98% and most preferably more than 99% of Neu5Gc, this protein is useful for control of antibodies for example It is realized that the desialylated, the residually monosialylated proteins, and α3-resialylated or α6-sialylated proteins according to the invention are useful reagents for studies of specificities of antibodies and biological activities of protein comprising the specific sialylated structure.

The invention is further directed to process involving desialylation and resialylation of a mammalian NeuGc comprising proteins according to the invention.

EXAMPLES

Example 1

Detection of N-Glycolylneuraminic Acid Containing Glycan Structures in Stem Cell and Differentiated Cell Samples, Cell Culture Media, and Biological Reagents Examples of Cell Material Production
Cord Blood Cell Populations Preparation of mononuclear cells. Cord blood was diluted 1:4 with phosphate buffered saline (PBS)-2 mM EDTA and 35 ml of diluted cord blood was carefully layered over 15 ml of Ficoll-Paque® (Amersham Biosciences, Piscataway, USA). Tubes were centrifuged for 40 minutes at 400 g without brake. Mononuclear cell layer at the interphase was collected and washed twice in PBS-2 mM EDTA. Tubes were centrifuged for 10 minutes at 300 g.

Positive selection of CD34+/CD133+ cells. The cord blood mononuclear cell pellet was resuspended in a final volume of 300 μl of PBS-2 mM EDTA-0.5% BSA (Sigma, USA) per $10^8$ total cells. To positively select CD34+ or CD133+ cells, 100 μl of FcR Blocking Reagent and 100 μl CD34 or CD133 Microbeads (Miltenyi Biotec, Bergisch Gladbach, Germany) were added per $10^8$ mononuclear cells. Suspension was incubated for 30 minutes at 6-12° C. Cells were washed with PBS-2 mM EDTA-0.5% BSA and resuspended in 500 μl of PBS-2 mM EDTA-0.5% BSA per $10^8$ cells.

The appropriate MACS affinity column type (Miltenyi Biotec, Bergisch Gladbach, Germany) was chosen according to the number of total cells: MS column for <$2 \times 10^8$ cells and LS column for $2 \times 10^8$-$2 \times 10^9$ cells. The column was placed in the magnetic field and rinsed with PBS-2 mM EDTA-0.5% BSA. Labeled cell suspension was applied to the column and the cells passing through the column were collected as the negative cell fraction (CD34− or CD133−). The column was then washed four times with PBS-2 mM EDTA-0.5% BSA. The column was removed from the magnetic field and the retained positive cells (CD34+ or CD133+) were eluted with PBS-2 mM EDTA-0.5% BSA using a plunger.

The eluted positive cells were centrifuged for 5 minutes at 300 g and resuspended in 300 μl PBS-2 mM EDTA-0.5% BSA. 25 μl of FcR Blocking Reagent and 25 μl CD34 or CD133 Microbeads were added. Suspension was incubated for 15 minutes at 6-12° C. Cells were washed with PBS-2 mM EDTA-0.5% BSA and resuspended in 500 μl of PBS-2 mM EDTA-0.5% BSA.

A MS column was placed in the magnetic field and rinsed with PBS-2 mM EDTA-0.5% BSA. Labeled cell suspension was applied to the column. The column was washed four times with PBS-2 mM EDTA-0.5% BSA. The column was then removed from the magnetic field and the retained positive cells (CD34+ or CD133+) were eluted with PBS-2 mM EDTA-0.5% BSA using a plunger.

Negative selection of Lin− cells. To deplete lineage committed cells, mononuclear cells ($8 \times 10^7$/ml) in PBS-0.5% BSA were labeled with 100 μl/ml cells with StemSep Progenitor Enrichment Cocktail containing antibodies against CD2, CD3, CD14, CD16, CD19, CD24, CD56, CD66b, Glycophorin A (StemCell Technologies, Vancouver, Canada) at room temperature for 15 minutes. Subsequently, 60 μl of colloidal magnetic iron particles were added per 1 ml cell suspension and incubated at room temperature for 15 minutes.

The labeled cell suspension was loaded into MACS LD column (Miltenyi Biotec) and unlabeled cells passing through the column were collected as the negative fraction (Lin−). LD column was washed twice with 1 ml PBS-0.5% BSA and effluents were collected into the same tube with unlabelled cells. The column was then removed from the magnetic field and the retained positive cells (Lin+) were eluted with PBS-0.5% BSA using a plunger.

Cord Blood Mesenchymal Stem Cell Lines

Collection of umbilical cord blood. Human term umbilical cord blood (UCB) units were collected after delivery with informed consent of the mothers and the UCB was processed within 24 hours of the collection. The mononuclear cells (MNCs) were isolated from each UCB unit diluting the UCB 1:1 with phosphate-buffered saline (PBS) followed by Ficoll-Paque Plus (Amersham Biosciences, Uppsala, Sweden) density gradient centrifugation (400 g/40 min). The mononuclear cell fragment was collected from the gradient and washed twice with PBS.

Umbilical cord blood cell isolation and culture. CD45/Glycophorin A (GlyA) negative cell selection was performed using immunolabeled magnetic beads (Miltenyi Biotec). MNCs were incubated simultaneously with both CD45 and GlyA magnetic microbeads for 30 minutes and negatively selected using LD columns following the manufacturer's instructions (Miltenyi Biotec). Both CD45/GlyA negative elution fraction and positive fraction were collected, suspended in culture media and counted. CD45/GlyA positive cells were plated on fibronectin (FN) coated six-well plates at the density of $1 \times 10^6/cm^2$. CD45/GlyA negative cells were plated on FN coated 96-well plates (Nunc) about $1 \times 10^4$ cells/well. Most of the non-adherent cells were removed as the medium was replaced next day. The rest of the non-adherent cells were removed during subsequent twice weekly medium replacements.

The cells were initially cultured in media consisting of 56% DMEM low glucose (DMEM-LG, Gibco, http://www.invitrogen.com) 40% MCDB-201 (Sigma-Aldrich) 2% fetal calf serum (FCS), 1× penicillin-streptomycin (both from Gibco), 1×ITS liquid media supplement (insulin-transferrin-selenium), 1× linoleic acid-BSA, $5 \times 10^{-8}$ M dexamethasone, 0.1 mM L-ascorbic acid-2-phosphate (all three from Sigma-Aldrich), 10 nM PDGF (R&D systems, http://www.RnDSystems.com) and 10 nM EGF (Sigma-Aldrich). In later passages (after passage 7) the cells were also cultured in the same proliferation medium except the FCS concentration was increased to 10%.

Plates were screened for colonies and when the cells in the colonies were 80-90% confluent the cells were subcultured. At the first passages when the cell number was still low the cells were detached with minimal amount of trypsin/EDTA (0.25%/1 mM, Gibco) at room temperature and trypsin was inhibited with FCS. Cells were flushed with serum free culture medium and suspended in normal culture medium adjusting the serum concentration to 2%. The cells were plated about 2000-3000/cm². In later passages the cells were detached with trypsin/EDTA from defined area at defined time points, counted with hematocytometer and replated at density of 2000-3000 cells/cm².

Isolation and culture of bone marrow derived stem cells. Bone marrow (BM)-derived MSCs were obtained as described by Leskelä et al. (2003). Briefly, bone marrow obtained during orthopedic surgery was cultured in Minimum Essential Alpha-Medium (α-MEM), supplemented with 20 mM HEPES, 10% FCS, 1× penicillin-streptomycin and 2 mM L-glutamine (all from Gibco). After a cell attachment period of 2 days the cells were washed with $Ca^{2+}$ and $Mg^{2+}$ free PBS (Gibco), subcultured further by plating the cells at a density of 2000-3000 cells/cm2 in the same media and removing half of the media and replacing it with fresh media twice a week until near confluence.

Flow cytometric analysis of mesenchymal stem cell phenotype. Both UBC and BM derived mesenchymal stem cells were phenotyped by flow cytometry (FACSCalibur, Becton Dickinson). Fluorescein isothicyanate (FITC) or phycoerythrin (PE) conjugated antibodies against CD13, CD14, CD29, CD34, CD44, CD45, CD49e, CD73 and HLA-ABC (all from BD Biosciences, San Jose, Calif., http://www.bdbiosciences.com), CD105 (Abcam Ltd., Cambridge, UK, http://www.abcam.com) and CD133 (Miltenyi Biotec) were used for direct labeling. Appropriate FITC- and PE-conjugated isotypic controls (BD Biosciences) were used. Unconjugated antibodies against CD90 and HLA-DR (both from BD Biosciences) were used for indirect labeling. For indirect labeling FITC-conjugated goat anti-mouse IgG antibody (Sigma-aldrich) was used as a secondary antibody.

The UBC derived cells were negative for the hematopoietic markers CD34, CD45, CD14 and CD133. The cells stained positively for the CD13 (aminopeptidase N), CD29 (β1-integrin), CD44 (hyaluronate receptor), CD73 (SH3), CD90 (Thy1), CD105 (SH2/endoglin) and CD 49e. The cells stained also positively for HLA-ABC but were negative for HLA-DR. BM-derived cells showed to have similar phenotype. They were negative for CD14, CD34, CD45 and HLA-DR and positive for CD13, CD29, CD44, CD90, CD105 and HLA-ABC.

Adipogenic differentiation. To assess the adipogenic potential of the UCB-derived MSCs the cells were seeded at the density of $3 \times 10^3/cm^2$ in 24-well plates (Nunc) in three replicate wells. UCB-derived MSCs were cultured for five weeks in adipogenic inducing medium which consisted of DMEM low glucose, 2% FCS (both from Gibco), 10 µg/ml insulin, 0.1 mM indomethacin, 0.1 µM dexamethasone (Sigma-Aldrich) and penicillin-streptomycin (Gibco) before samples were prepared for glycome analysis. The medium was changed twice a week during differentiation culture.

Osteogenic differentiation. To induce the osteogenic differentiation of the BM-derived MSCs the cells were seeded in their normal proliferation medium at a density of $3 \times 10^3/cm^2$ on 24-well plates (Nunc). The next day the medium was changed to osteogenic induction medium which consisted of α-MEM (Gibco) supplemented with 10% FBS (Gibco), 0.1 µM dexamethasone, 10 mM β-glycerophosphate, 0.05 mM L-ascorbic acid-2-phosphate (Sigma-Aldrich) and penicillin-streptomycin (Gibco). BM-derived MSCs were cultured for three weeks changing the medium twice a week before preparing samples for glycome analysis.

Cell harvesting for glycome analysis. 1 ml of cell culture medium was saved for glycome analysis and the rest of the medium removed by aspiration. Cell culture plates were washed with PBS buffer pH 7.2. PBS was aspirated and cells scraped and collected with 5 ml of PBS (repeated two times). At this point small cell fraction (10 µl) was taken for cell-counting and the rest of the sample centrifuged for 5 minutes at 400 g. The supernatant was aspirated and the pellet washed in PBS for an additional 2 times.

The cells were collected with 1.5 ml of PBS, transferred from 50 ml tube into 1.5 ml collection tube and centrifuged for 7 minutes at 5400 rpm. The supernatant was aspirated and washing repeated one more time. Cell pellet was stored at −70° C. and used for glycome analysis.

Human Embryonic Stem Cell Lines (hESC)

Undifferentiated hESC. Processes for generation of hESC lines from blastocyst stage in vitro fertilized excess human embryos have been described previously (e.g. Thomson et al., 1998). Two of the analysed cell lines in the present work were initially derived and cultured on mouse embryonic fibroblasts feeders (MEF; 12-13 pc fetuses of the ICR strain), and two on human foreskin fibroblast feeder cells (HFF; CRL-2429 ATCC, Mananas, USA). For the present studies all the lines were transferred on HFF feeder cells treated with mitomycin-C (1 µg/ml; Sigma-Aldrich) and cultured in serum-free medium (Knockout™ D-MEM; Gibco® Cell culture systems, Invitrogen, Paisley, UK) supplemented with 2 mM L-Glutamin/Penicillin streptomycin (Sigma-Aldrich), 20% Knockout Serum Replacement (Gibco), 1× non-essential amino acids (Gibco), 0.1 mM β-mercaptoethanol (Gibco), 1×ITSF (Sigma-Aldrich) and 4 ng/ml bFGF (Sigma/Invitrogen).

Stage 2 differentiated hESC (embryoid bodies). To induce the formation of embryoid bodies (EB) the hESC colonies were first allowed to grow for 10-14 days whereafter the colonies were cut in small pieces and transferred on non-adherent Petri dishes to form suspension cultures. The formed EBs were cultured in suspension for the next 10 days in standard culture medium (see above) without bFGF.

Stage 3 differentiated hESC. For further differentiation EBs were transferred onto gelatin-coated (Sigma-Aldrich) adherent culture dishes in media consisting of DMEM/F12 mixture (Gibco) supplemented with ITS, Fibronectin (Sigma), L-glutamine and antibiotics. The attached cells were cultured for 10 days whereafter they were harvested Sample preparation. The cells were collected mechanically, washed, and stored frozen prior to glycan analysis.

Experimental Procedures

Biological reagents. Bovine serum apotransferrin and fetuin were from Sigma (USA).

Glycan isolation. N-linked glycans were detached from cellular glycoproteins by *F. meningosepticum* N-glycosidase F digestion (Calbiochem, USA) essentially as described previously (Nyman et al., 1998), after which the released glycans were purified for analysis by solid-phase extraction methods, including ion exchange separation, and divided into sialylated and non-sialylated fractions.

MALDI-TOF mass spectrometry. MALDI-TOF mass spectrometry was performed with a Voyager-DE STR Bio-Spectrometry Workstation or a Bruker Ultraflex TOF/TOF instrument, essentially as described previously (Saarinen et al., 1999; Harvey et al., 1993). Relative molar abundancies of both neutral (Naven & Harvey, 1996) and sialylated (Papac et al., 1996) glycan components were assigned based on their relative signal intensities. The mass spectrometric fragmentation analysis was done with the Bruker Ultraflex TOF/TOF instrument according to manufacturer's instructions.

Sialic acid analysis. Sialic acids were released from sample glycoconjugates by mild propionic acid hydrolysis, reacted with 1,2-diamino-4,5-methylenedioxybenzene (DMB), and analyzed by reversed-phase high-performance liquid chromatography (HPLC) essentially as described previously (Ylönen et al., 2001).

Results

N-glycan analysis of stem cell samples. N-glycans from samples of various stem cell and differentiated cells, as well as from culture media and other biological reagents used in treatment of these samples, were isolated and fractionated into neutral and sialylated N-glycan fractions as described under Experimental procedures. In MALDI-TOF mass spectrometry of the sialylated N-glycan fractions, several glycan signals were detected in these samples that indicated the presence of N-glycolylneuraminic acid (Neu5Gc) in the N-glycans. As an example, FIG. 1 shows mass spectra of sialylated N-glycan fractions from stem cell samples (A. and B.), commercial cell culture media (C. and E.), and bovine serum glycoproteins (D. and F.). The glycan signals at m/z 1946 (upper panel), corresponding to the [M-H]$^-$ ion of NeuGc$_1$Hex$_5$HexNAc$_4$, as well as m/z 2237 and m/z 2253 (lower panel), corresponding to the [M-H]$^-$ ions of NeuGc$_1$NeuAc$_1$Hex$_5$HexNAc$_4$ and NeuGc$_2$Hex$_5$HexNAc$_4$, respectively, are indicative of the presence of N-glycolylneuraminic acid, i.e. a sialic acid residue with 16 Da larger mass than N-acetylneuraminic acid (Neu5Ac).

The indicative glycan signals and other signals proposed to correspond to Neu5Gc-containing glycan species are listed in Table 1, along with the mass spectrometric profiling results obtained from stem cell samples. CD133$^+$ cells from human cord blood are representative of cord blood cell populations in the present example and other cell populations detected to contain similar Neu5Gc glycoconjugates included CD34$^+$ and LIN$^-$ cells from cord blood. Mesenchymal stem cells from human bone marrow are representative of mesenchymal stem cell lines in the present example and other mesenchymal stem cell lines detected to contain similar Neu5Gc glycoconjugates included cell lines derived from cord blood.

Mass spectrometric profiling results obtained from cell culture media and biological reagents are listed below. The indicative glycan signals and other signals proposed to correspond to Neu5Gc-containing glycan species in the studied reagents are listed in Table 6. The results indicate for the presence of Neu5Gc in the listed reagents.

Glycan profiling of reagents. N-glycans were liberated from reagents enzymatically by N-glycosidase F, purified and analysed by mass spectrometry. The results are summarized below.

1. Following Reagents Contained Detectable Amounts of N-Glycans:

Commercial BSA (bovine serum albumin)
Fetal bovine serum (FBS)
Transferrin, bovine serum
Horse serum
Monoclonal antibodies, including murine antibodies
Cell culture media 2. Reagents Containing N-Glycolyl Neuraminic Acid (NeuGc) or Acetyl-Groups (Ac):

Following lists present masses detected from mass spectra and their corresponding proposed monosaccharide compositions (exact calculated mass values are presented in Table 6). General Mono Saccharide Compositions of Common Animal N-Glycan Structures Comprising N-Glycolyl Neuraminic Acid (NeuGc) or Acetyl-Groups (Ac):

It is realized that various animal species produced large number of different proteins. The following general composition describes some useful major signals and the present invention is directed to especially analysis of these, preferably in context of serum/blood derived samples from mammals, preferably from horse and/or bovine. The invention is directed to the analysis of individual isolated proteins such as serum transferrin or an antibody, and preferably analysis of variation among the individual protein (depending on animal individual, condition of the animal, animal strain or species, for example). The invention is further and preferably directed to analysis of complex protein mixture such as animal tissue fractions such as blood fractions, more preferably serum fractions. The signals are especially useful as these are not commonly observed from human tissue or cell materials with contamination of animal material. As the glycans posses known antigenicity and other risks it is useful to analyse presence of these for example from therapeutic products such as therapeutic cell products or reagents aimed for production of these.

The invention is further directed to methods, especially research and development methods, such as product development methods, according to the invention including step of producing a qualitative and/or quantitative glycome analysis from cell culture directed materials or for development of these or producing a qualitative and/or quantitative glycome analysis from cells for revealing potential presence of or contamination by non-human protein material such as animal protein, such as a mammalian sialylated protein. It is realized that cell culture reagents can be produced by various cell culture methods producing non-human N-glycosylation such as preferably by non-mammalian or non-vertebrate cell systems preferably by plant, fungal, yeast or insect cells or engineered versions of these producing human similar glycomes, which have different biological activities need to be analysed and are analysed preferably by the methods according to the invention.

The general monosaccharide composition for characteristic major glycan signals (structures) to be analyzed in context of animal protein N-glycans, preferably from serum, (comprising NeuGc-glycans and/or O-acetyl structures such as O-acetylated sialic acids such as NeuNAc-OAc-glycans) is according to formula:

$$NeuGc_{n1}NeuNAc_{n2}Hex_{n3}HexNAc_{n4}dHex_{n5}Ac_{n6},$$

wherein n1 is an integer with values 0-5, preferably 0-4, more preferably 0-3, most preferably 0, 1 or 2;
n2 is an integer with values 0-5, preferably 0-4, more preferably 0-3, most preferably is 0, 1 or 2;
n3 is an integer having values from 1 to 8, more preferably values 1 or from 3-8, even more preferably values 1 or from 3-6, preferably from 3 to 6, most preferably 3, 5 or 6;
n4 is an integer having values from 2-7, more preferably 2-6, even more preferably 2-5 or 3-6 and most commonly preferably 3-5
n5 is an integer having values 0-3, and
n6 is an integer with values 0-4, preferred ranges further includes 0, 1 or 2, and 0, 1, 2 or 4.

It is realized that the protein composition may comprise multiple branched N-glycan increasing the amount of sialic acids and n3 and n4 with increasing amount of terminal N-acetyllactosamines. It is further realized that when the N-glycan comprise poly-nacetyllactosamines the values of monosaccharide units in observable signals with n3 and n4 and optionally also number of sialic acid (n1 and n2 and possible acetylation there of n6), when branching is increased, and number of fucose (n5, increase in n5 is typically smaller than increase of N-acetyllactosamines), when fucosylation of N-acetyllactosamines is increased, can be and increased by numbers between about 1-10, more preferably the number of the monosaccharide units in compositions is increased with number between 1-5 or in case of common modest increase in N-acetyllactosamines the increase is 1-3.

The most preferred compositions were revealed to comprise monosaccharide compostions of common bianennary complex type N-glycans, and some unusual smaller variations thereof.

Commercial BSA

The monosaccharide composition for characteristic glycan signals (structures) to be analyzed in context of commercial bovine serum transferring (comprising NeuGc-glycans) includes signals according formula:

$$NeuGc_{n1}NeuNAc_{n2}Hex_{n3}HexNAc_{n4}dHex_{n5},$$

wherein n1 is 1 or 2;
n2 is 0, or 1;
n3 is an integer having values from 3-5;
n4 is an integer having values from 3-4 and
n5 is an integer having values 0 or 1, examples of preferred compositions are listed below.

The compositions are quite similar to bovine serum proteins but only part of glycans are included. Examples and most preferred signals to be analyzed from animal serum albumin, preferably bovine serum albumin, samples includes following mass signals and/or monosaccharide compositions:
1419 NeuGcHex3HexNAc3
1581 NeuGcHex4HexNAc3
1946 NeuGcHex5HexNAc3
2237 NeuGcNeuAcHex5HexNAc4
2253 NeuGc2Hex5HexNAc4
2383 NeuGcNeuAcHex5HexNAc4dHex
2399 NeuGc2Hex5HexNAc4dHex
2528 NeuGcNeuAc2Hex5HexNAc4
2544 NeuGc2NeuAcHex5HexNAc4

Commercial Antibody Preparations

O-acetylated NeuNAc residues were found. The present invention is in a preferred embodiment directed to analysis NeuAc-OAc comprising N-glycans from antibodies. The invention is especially directed to analysis of disialylated antibodies with following monosaccharide compositions. The compositions correspond to biantennary N-glycans comprising 1, 2, or 4 O-acetyl groups. It is realized that O-acetyl structures are likely antigenic and may affect also other biological activities of glycans such as interactions with sialic acid binding lectins, for example serum lectins in therapeutic or diagnostic applications. The invention is therefore directed to the analysis of Neu-OAc comprising glycans from commercial proteins such as antibodies.

The invention is especially directed to compositions:

$$NeuAc2Hex5HexNAc4Acn,$$

wherein n is an integer 1-4, preferably 1, 2, or 4, as shown below:
2263    NeuAc2Hex5HexNAc4Ac (NeuAcHex4HexNAc5dHex2)
2305 NeuAc2Hex5HexNAc4Ac2
2389 NeuAc2Hex5HexNAc4Ac4

Transferrin, Bovine Serum

The monosaccharide composition for characteristic glycan signals (structures) to be analyzed in context of commercial bovine serum transferring (comprising NeuGc-glycans) includes signals according to formula:

$$NeuGc_{n1}NeuNAc_{n2}Hex_{n3}HexNAc_{n4}dHex_{n5},$$

wherein n1 is 1 or 2;
n2 is 0, 1 or 2;
n3 is an integer having values from 3-6;
n4 is an integer having values from 3-4 and
n5 is an integer having values from 0-2, examples of preferred compositions are listed below.

The compositions are quite similar to commercial serum replacement shown below.

Examples and most preferred signals to be analyzed from animal serum transferrin, preferably bovine serum transferrin, samples includes following mass signals and/or monosaccharide compositions:
1419 NeuGcHex3HexNAc3
1581 NeuGcHex4HexNAc3
1784 NeuGcHex4HexNAc4
1946 NeuGcHex5HexNAc3
2092 NeuGcHex5HexNAc4dHex
2237 NeuGcNeuNAcHex5HexNAc4
2253 NeuGc2Hex5HexNAc4
2254 NeuGcHex6HexNAc4dHex
2383 NeuGcNeuAcHex5HexNAc4dHex
2399 NeuGc2Hex5HexNAc4dHex
2528 NeuGcNeuAc2Hex5HexNAc4
2539 NeuGcNeuAcHex5HexNAc4dHex2
2544 NeuGc2NeuAcHex5HexNAc4
2545 NeuGcNeuAcHex6HexNAc4dHex The invention further revealed that there is individual variation in the quantitative composition of individual animal glycoproteins, such as bovine serum proteins, preferably bovine serum transferrin. A preferred variable in to be determined is relative amount of sialylated and neutral glycans and/or relation of monosialylated and multiply sialylated glycans, preferably disialylated glycans; and/or the ratio of nonfucosylated glycans to mono- and or multiply fucosylated glycans; and or the ration of mono-fucosylated glycans to multiply fucosylated glycans. The quantitative composition means relative amounts of components of individual peaks, preferably measured as intensity of the peaks. The present invention is especially directed to determination of the quantitative composition of glycomes isolated from animal proteins and quantitative comparisons of the compositions.

Horse Serum

The monosaccharide composition for characteristic glycan signals (structures) to be analyzed in context of horse serum type materials (comprising NeuGc-glycans) is according to formula:

$$NeuGc_{n1}NeuNAc_{n2}Hex_{n3}HexNAc_{n4}dHex_{n5}Ac_{n6},$$

wherein n1 is 0, 1 or 2;
n2 is 0, 1 or 2;
n3 is an integer having values from 3-5, preferably 3, 5 or 6;
n4 is an integer having values from 3-5,
n5 is an integer having values 0 or 1, and
n6 is an integer 0, 1 or 2.
2092 NeuGcHex5HexNAc4dHex (NeuAcHex6HexNAc4)
2237 NeuGcNeuAcHex5HexNAc4
2238 NeuGcHex5HexNAc4dHex2 (NeuAcHex6HexNAc4dHex)
2254 NeuGcHex6HexNAc4dHex (NeuAcHex7HexNAc4)
2399 NeuGc2Hex5HexNAc4dHex $$NeuGc_{n1}NeuNAc_{n2}Hex_{n3}HexNAc_{n4}dHex_{n5}Ac_{n6},$$

wherein n1 is 1 or 2;
n2 is 0, or 1;
n3 is an integer having values from 3-5, preferably 3, 5 or 6;
n4 is an integer having values from 3-5,
n5 is an integer having values 0 or 1, and
n6 is an integer 0; examples of preferred compositions are included above
1445 NeuAcHex3HexNAc3Ac
1972 NeuAcHex5HexNAc4Ac
2263 NeuAc2Hex5HexNAc4Ac
2305 NeuAc2Hex5HexNAc4Ac2
2321 NeuAcHex5HexNAc5dHexAc
2409 NeuAc2Hex5HexNAc4dHexAc
2451 NeuAc2Hex5HexNAc4dHexAc2
2483 NeuAcHex6HexNAc5dHexAc
2467 NeuAcHex5HexNAc5dHex2Ac The preferred acetylated sequences analysed to correspond to O-acetylated sialic acids (NeuAc) are according to the formula:

$$(NeuGc_{n1})NeuNAc_{n2}Hex_{n3}HexNAc_{n4}dHex_{n5}Ac_{n6},$$

wherein n1 is 0, the sequences comprise practically all Neu-NAc;
n2 is 0, 1;
n3 is an integer having values from 3-6, preferably 3, 5 or 6;
n4 is an integer having values from 3-5,
n5 is an integer having values 0, 1 or 2, and
n6 is an integer 0, 1 or 2; examples of preferred compositions are included above.

3. Cell Culture Media Analysed:
Commercial Serum Replacement Cell Culture Media

The monosaccharide composition for characteristic glycan signals (structures) to be analyzed in context of commercial serum replacement cell culture media (comprising NeuGc-glycans) includes signals according to formula:

$$NeuGc_{n1}NeuNAc_{n2}Hex_{n3}HexNAc_{n4}dHex_{n5},$$

wherein n1 is 0, 1 or 2, preferably 1 or 2;
n2 is 0, or 1;
n3 is an integer having values from 3-7, preferably 3-6;
n4 is an integer having values from 3-5 and
n5 is an integer having values from 0-3.
1419 NeuGcHex3HexNAc3
1581 NeuGcHex4HexNAc3
1727 NeuGcHex4HexNAc3dHex
1743 NeuGcHex5HexNAc3
1784 NeuGcHex4HexNAc4
1946 NeuGcHex5HexNAc3
2092 NeuGcHex5HexNAc4dHex
2237 NeuGcNeuAcHex5HexNAc4
2238 NeuGcHex5HexNAc4dHex2
2253 NeuGc2Hex5HexNAc4
2254 NeuGcHex6HexNAc4dHex
2383 NeuGcNeuAcHex5HexNAc4dHex
2384 NeuGcHex5HexNAc4dHex3
2399 NeuGc2Hex5HexNAc4dHex
2528 NeuGcNeuAc2Hex5HexNAc4
2529 NeuGcNeuAcHex5HexNAc4dHex2
2544 NeuGc2NeuAcHex5HexNAc4
2545 NeuGcNeuAcHex6HexNAc4dHex
2560 NeuGc3Hex5HexNAc4
2602 NeuGcNeuAcHex6HexNAc5
2603 NeuGcHex6HexNAc5dHex2 (NeuAcHex7HexNAc5dHex)

FBS-Containing Cell Culture Media

The monosaccharide composition for characteristic glycan signals (structures) to be analyzed in context of fetal bovine serum is according to formula:

$$NeuGc_{n1}NeuNAc_{n2}Hex_{n3}HexNAc_{n4}dHex_{n5}Ac_{n6},$$

wherein n1 is 0, 1 or 2;
n2 is 0, 1 or 2;
n3 is an integer being 1, or 4-6;
n4 is an integer having values from 2-6 and
n5 is an integer having values 0, 1 or 2.
n6 is an integer 0, or 1; examples of preferred compositions are included above.

The invention is especially directed to analysis of presence of unusual signals at m/z 1038, NeuGcHexHexNAc2dHex, and 1329 NeuGcNeuAcHexHexNAc2dHex, the invention is further directed to the analysis of such structures from bovine serum, especially from FBS, preferably by specific glycosidase reagents, and/or fragmentation mass spectrometry and/or NMR-spectrometry.
1038 NeuGcHexHexNAc2dHex
1329 NeuGcNeuAcHexHexNAc2dHex
1727 NeuGcHex4HexNAc3dHex
1946 NeuGcHex5HexNAc3
2092 NeuGcHex5HexNAc4dHex
2237 NeuGcNeuAcHex5HexNAc4
2238 NeuGcHex5HexNAc4dHex2
2253 NeuGc2Hex5HexNAc4
2254 NeuGcHex6HexNAc4dHex
2366 NeuGcNeuAc2Hex4HexNAc4
2383 NeuGcNeuAcHex5HexNAc4dHex
2409 NeuAc2Hex5HexNAc4dHexAc
2528 NeuGcNeuAc2Hex5HexNAc4
2529 NeuGcNeuAcHex5HexNAc4dHex2
2544 NeuGc2NeuAcHex5HexNAc4
2602 NeuGcNeuAcHex6HexNAc5
2618 NeuGc2Hex6HexNAc5
2674 NeuGcNeuAc2Hex5HexNAc4dHex
2893 NeuGcNeuAc2Hex6HexNAc5

Horse Serum Containing Cell Culture Media

The monosaccharide composition for characteristic glycan signals (structures) to be analyzed in context of horse serum comprising celculturee media (comprising NeuGc-glycans and/or NeuNAc-OAc-glycans) is according to formula:

$$NeuGc_{n1}NeuNAc_{n2}Hex_{n3}HexNAc_{n4}dHex_{n5}Ac_{n6},$$

wherein n1 is 0, 1 or 2;
n2 is 0, 1 or 2;
n3 is an integer having values from 3-6, preferably 3, 5 or 6;
n4 is an integer having values from 3-5,
n5 is an integer having values 0 or 1, and
n6 is an integer 0, 1 or 2.
1581 NeuGcHex4HexNAc3
1711 NeuGcHex3HexNAc3dHex2
1727 NeuGcHex4HexNAc3
1873 NeuGcHex4HexNAc3dHex2
1946 NeuGcHex5HexNAc3
2092 NeuGcHex5HexNAc4dHex
2237 NeuGcNeuAcHex5HexNAc4
2238 NeuGcHex5HexNAc4dHex2
2310 NeuGcNeuAcHex4HexNAc3dHex3
2366 NeuGcNeuAc2Hex4HexNAc4
2383 NeuGcNeuAcHex5HexNAc4dHex
2384 NeuGcHex5HexNAc4dHex3
2399 NeuGc2Hex5HexNAc4dHex The preferred subgroup of NeuGc comprising glycans includes $$NeuGc_{n1}NeuNAc_{n2}Hex_{n3}HexNAc_{n4}dHex_{n5}Ac_{n6},$$

wherein n1 is 1 or 2;
n2 is 0, 1 or 2;
n3 is an integer having values from 3-5;
n4 is an integer having values 3 or 4,
n5 is an integer having values 0-4, and
n6 is an integer 0.

It is realized that the horse serum comprising medium contained signals 2310, 2366, 2383, and 2384 in addition to the horse serum signals listed above and lacked the signal at m/z 2254. These are considered as characteristic signals/components differentiating between animal protein materials, especially in comparison between horse derived materials.
1972 NeuAcHex5HexNAc4Ac
2263 NeuAc2Hex5HexNAc4Ac
2305 NeuAc2Hex5HexNAc4Ac2
2321 NeuAcHex5HexNAc5dHexAc
2409 NeuAc2Hex5HexNAc4dHexAc
2483 NeuAcHex6HexNAc5dHexAc It is notable that the horse serum derived cell culture media contained more NeuGc comprising glycan structures and less NeuNAc-OAc structures lacking peaks at m/z 1445 2451 and 2467 in comparison to the horse serum sample above. These are considered as characteristic signals/components differentiating between animal protein materials, especially in comparison between horse derived materials.

The invention is directed to analysis of variation of animal derived cell culture materials such as serum proteins used for cell culture and use of the monosaccharide compositions and/or the characteristics signals for analysis of differences between animal protein materials, especially animal derived cell culture materials or materials to best tested for suitability for such materials. The invention is directed to variation related to individual animals within the same species and being the source of, or producing, the sample materials and analysis of variations between animal species. In a preferred embodiment the invention is directed to recognition of the source (tissue type such as serum, individual animal, animal strain or animal species) of the protein by analysis of expressed glycans.

In a preferred embodiment the invention is directed to the analysis of, preferably analysis of presence or absence or level of, O-acetylated sialic acid in the sample material and/or the analysis of, preferably analysis of presence or absence or level of, NeuGc sialic acid and/or presence of various signals/monosaccharide compositions/structures differentiating animal protein samples. The invention is especially directed to simultaneous analysis of O-acetylated sialic acid and NeuGc, preferably by specific binding molecules such as specific binding proteins or more preferably by physical methods such as NMR and/or mass spectrometry, most preferably MALDI-TOF mass spectrometry.

Figure 2:
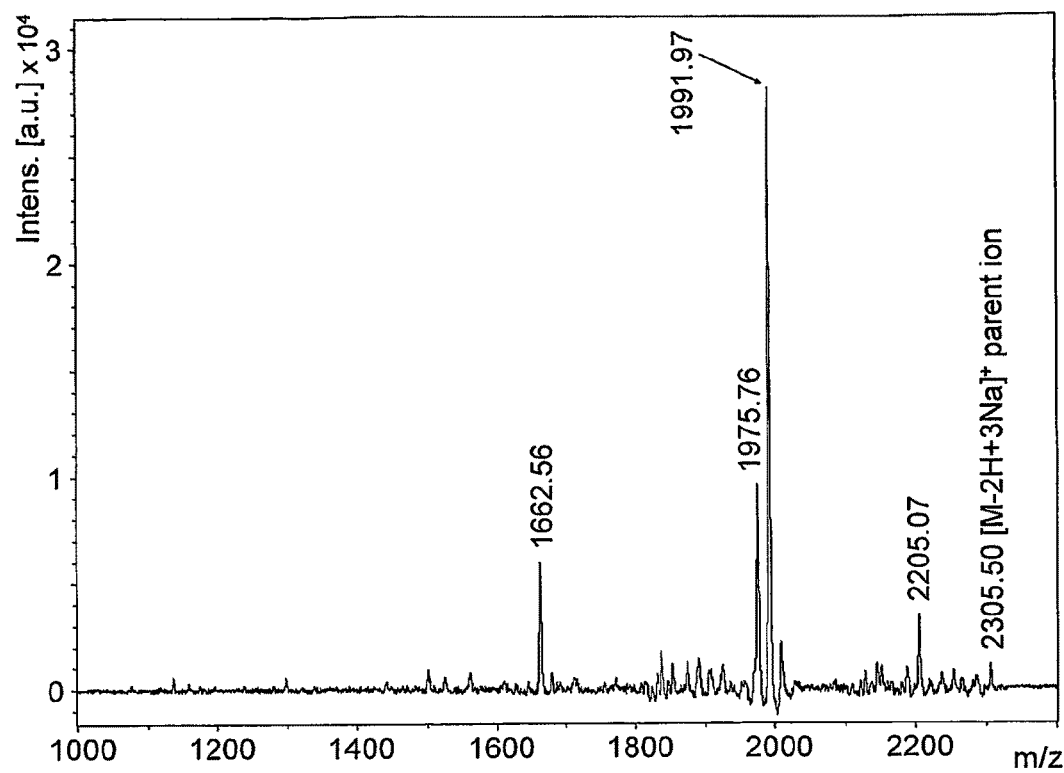
FIG. 2. Fragmentation mass spectrometry of parent ion at m/z 2305.50 corresponding to M-2H+3Na]$^+$ adduct ion of NeuAc$_1$NeuGc$_1$Hex$_5$HexNAc$_4$. Fragment ions corresponding to loss of NeuAcNa (m/z 1991.97), NeuGcNa (m/z 1975.76), or NeuAcNa+NeuGcNa (m/z 1662.56) are the major fragmentation products. x-axis: mass-to-charge ratio (m/z); y-axis: relative signal intensity in arbitrary units (a.u.); m/z 2205.07: unknown.

Fragmentation mass spectrometry. A sample of sialylated N-glycans isolated from cord blood CD133$^+$ cells was subjected to mass spectrometric fragmentation analysis. Two different sodium adduct signals at m/z 2261 [M+Na]$^+$ and 2305 [M-2H+3Na]$^+$ were selected for fragmentation. The fragmentation spectrum of the [M-2H+3Na]$^+$ ion at m/z 2305.50 (calc. m/z 2305.73) together with the proposed fragment ions is depicted in FIG. 2. The glycan signals at m/z 1975.76, corresponding to the ion [NeuAcHex$_5$HexNAc$_4$–H+2Na]$^+$ (calc. m/z 1976.66), at m/z 1991.97, corresponding to the ion [NeuGcHex$_5$HexNAc$_4$–H+2Na]$^+$ (calc. m/z 1992.65), and at m/z 1662.56, corresponding to the ion [Hex$_5$HexNAc$_4$+Na]$^+$ (calc. m/z 1663.58), indicate the presence of one N-glycolyl neuraminic acid sodium salt residue ($M_{NeuGc-H+Na}$=329) and one N-acetyl neuraminic acid sodium salt residue ($M_{NeuAc-H+Na}$=313) in the original N-glycan ion. The fragmentation spectrum of the [M+Na]$^+$ ion at m/z 2261.86 (calc. m/z 2261.77), yielded a similar result, and the resulting fragment signals at m/z 1954.45, corresponding to the ion [NeuAcHex$_5$HexNAc$_4$+Na]$^+$ (calc. m/z 1954.68), at m/z 1969.93, corresponding to the ion [NeuGcHex$_5$HexNAc$_4$+Na]$^+$ (calc. m/z 1970.67), and at m/z 1664.82, corresponding to the ion [Hex$_5$HexNAc$_4$+Na]$^+$ (calc. m/z 1663.58), similarly indicate the presence of one N-glycolyl neuraminic acid residue ($M_{NeuGc}$=307) and one N-acetyl neuraminic acid residue ($M_{NeuAc}$=291) in the original N-glycan ion. In conclusion, the fragmentation analysis indicates that in the positive ion mode spectrum the glycan signals at m/z 2261 and 2305 correspond to the [M+Na]$^+$ and [M-2H+3Na]$^+$ ions of NeuAcNeuGcHex$_5$HexNAc$_4$, respectively, and in the negative ion mode spectrum the glycan signal at m/z 2237 corresponds to the [M-H]$^-$ ion of NeuAcNeuGcHex$_5$HexNAc$_4$.

Sialic acid analysis. As described above, mass spectrometric profiling analyses indicated the presence of Neu5Gc in various cell samples and biological reagents. The sialic acid composition of commercial bovine serum transferrin was analyzed as described under Experimental procedures. The analysis indicated that the sample contained Neu5Gc and Neu5Ac in an approximate ratio of 50:50. The result was practically similar to mass spectrometric profiling that indicated that sialylated N-glycans isolated from the same sample contained Neu5Gc and Neu5Ac in a ratio of 53:47, as calculated from the proposed monosaccharide compositions of the detected glycan signals and their relative signal intensities. However, this Neu5Gc:Neu5Ac composition was significantly different from earlier reports of bovine serum transferrin sialic acid analysis results (e.g. 64:36, Rohrer et al., 1998), indicating that individual glycoprotein batches can differ from each other with regard to their sialic acid composition.

Example 2

Detection of N-Glycolylneuraminic Acid Containing Glycoconjugates in Stem Cell Samples by Specific Antibodies Experimental Procedures Cell samples. Mesenchymal stem cells from bone marrow were generated and cultured in proliferation medium as described above.

Antibodies. Murine monoclonal antibody against the glycolipid antigen GM2(Neu5Gc) was from Seikagaku (Japan). Monoclonal antibody against the glycolipid antigen GM3 (Neu5Gc) was characterized to have binding specificity against GM3(Neu5Gc) as well as the sialyl(Neu5Gc)lacto-N-neotetraosyl glycolipid epitope by binding to glycolipid standard molecules on thin-layer chromatography plates.

Immunostainings. Bone-marrow derived mesenchymal stem cells (MSCs) on passages 9-14 were grown on 0.01% poly-L-lysine (Sigma, USA) coated glass 8-chamber slides (Lab-TekII, Nalge Nunc, Denmark) at 37° C. with 5% $CO_2$ for 2-4 days. After culturing, cells were rinsed 5 times with PBS (10 mM sodium phosphate, pH 7.2, 140 mM NaCl) and fixed with 4% PBS-buffered paraformaldehyde pH 7.2 at room temperature (RT) for 10 minutes, followed by washings 3 times 5 minutes with PBS. Some MSC samples were extracted with 0.1% Triton X-100 (Sigma) in PBS for 5 minutes at RT before blocking. Additionally, specificity of the staining was confirmed by sialidase treatment after fixation. Briefly, fixed MSC samples were incubated with 10 mU of sialidase (*Arthrobacter ureafaciens*, Glyko, UK) in 50 mM sodium acetate buffer pH 5.5 over night at 37° C. After detergent extraction or sialidase treatment, cells were washed 3 times 5 minutes with PBS. After fixation and different treatments the non-specific binding sites were blocked with 3% HSA-PBS (FRC Blood Service, Finland) for 30 minutes at RT. Primary antibodies were diluted in 1% HSA-PBS and incubated for 60 minutes at RT, followed by washings 3 times for 10 minutes with PBS. Secondary antibody, FITC-labeled goat-anti-mouse (Sigma) was diluted 1:300 in 1% HSA-PBS and incubated for 60 minutes at RT in the dark. Furthermore, cells were washed 3 times 5-10 minutes with PBS and mounted in Vectashield mounting medium containing DAPI-stain (Vector Laboratories, UK). Immunostainings were observed with Zeiss Axioskop 2 plus-fluorescence microscope (Carl Zeiss Vision GmbH, Germany) with FITC and DAPI filters. Images were taken with Zeiss AxioCam MRc-camera and with AxioVision Software 3.1/4.0 (Carl Zeiss) with the 400× magnification. Human embryonal stem cells were grown as described above and stained with monoclonal antibodies.

Results

Figure 3:
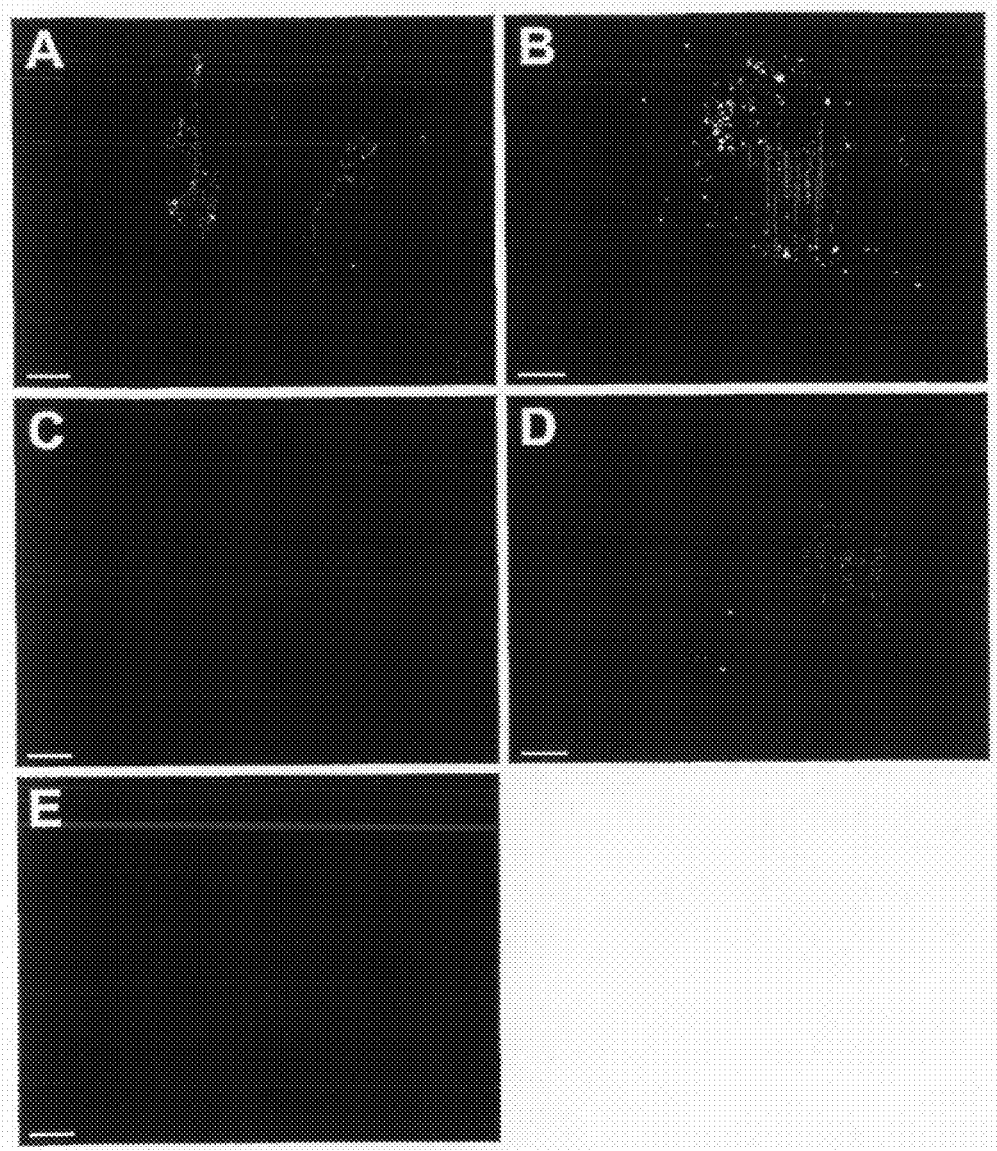
FIG. 3. Immunostainings of N-glycolylneuraminic acid in bone-marrow derived mesenchymal stem cells. A. Anti-GM2 (Neu5Gc) 20 μg/ml, B. Anti-GM3(Neu5Gc) 1:1000, C. Anti-GM3(Neu5Gc) 1:1000 after Triton extraction, D. Anti-GM3 (Neu5Gc) 1:1000 after sialidase treatment, and E. Negative control without primary antibody. See materials and methods for the staining procedure and imaging. Scale bar: 20 μm.

Mesenchymal stem cells. Both antibodies against N-glycolylneuraminic acid glycolipid antigens GM2/GM3 (Neu5Gc) showed clear staining at the cell surface in non-permeabilized MSCs (FIGS. 3A and 3B). Cell permeabilization and extraction with Triton X-100 at RT totally abolished GM3(Neu5Gc) staining (FIG. 3C), which suggests that antigen detected with this antibody is located in Triton-soluble lipid areas at the cell surface. After the extraction cytoplasmic GM3(Neu5Gc) staining was not observed (FIG. 3C). Sialidase treatment was used to control the specificity of the antibody. FIG. 3D clearly demonstrates that GM3 (Neu5Gc) staining is markedly decreased after sialidase treatment in MSCs. Background level of the stainings is showed in FIG. 3E.

Embryonal stem cells. The Neu5Gc antibodies against N-glycolylneuraminic acid glycolipid antigens showed staining at the cell surface in non-permeabilized human embryonal stem cells (hESCs; staining intensity with e.g. anti-GM2 (Neu5Gc) antibody classified as moderate). It was also demonstrated that staining was decreased after differentiation of hESCs into embryoid bodies (EB) and especially after further differentiation of hESCs (stage 3; staining intensity with e.g. anti-GM2(Neu5Gc) antibody classified as low).

Conclusions

It was demonstrated that Neu5Gc-specific monoclonal antibodies against glycolipid antigens stain both human bone marrow derived mesenchymal stem cells and human embryonal stem cells. The staining intensity was approximately correlated with Neu5Gc content of the culture medium, indicating that Neu5Gc in the culture medium is incorporated as glycoconjugates including glycolipid structures in stem cells. In addition, it was shown that sialidase treatment can remove Neu5Gc residues from stem cell surface antigens, including glycolipid structures.

Example 3

Effect of Culture Conditions on N-Glycolylneuraminic Acid Content of Cells

Results

Neu5Gc expression in embryonal stem cells under different culture conditions. Human embryonic stem cell, differentiated cell, and fibroblast feeder cell samples were produced, and their N-glycan compositions analyzed by mass spectrometry as described above. Proportions of N-glycolylneuraminic acid containing N-glycans of total sialylated N-glycans in different cell populations were as follows:

| Cell type: | Proportion of Neu5Gc-containing N-glycans: |
| --- | --- |
| 1. Undifferentiated stem cells | 41/1000 |
| 2. Embryoid bodies i.e. early differentiated cells | 3/200 |
| 3. Further differentiated cells | 0 |
| 4. Human fibroblast feeder cells | 0 |

The invention is especially directed to quantitative analysis of non-human sialic acids relative to total amount of sialic acids, analysis of proportion of NeuGc and/or O-acylated sialic acid from total sialic acids, more preferably portion of NeuGc and/or O-acylated sialic acid from total sialic acids in N-glycans in a sample according to the invention, sample being a purified or semipurified protein or more preferably a cell or tissue (such as serum or plasma) derived protein composition. In a preferred embodiment the quantitative amount of O-acetylated sialic acids is determined as proportion of total amount of sialic acid.

The quantitative determination of mass spectrometric signals is preferably based on the intensities of the signals, for quantitative determination of a proportional amount of a signals 1 to another type of signal(s) signal(s) 2, the intensities (as peak high or intensity, when determined to be produced quantitatively) of the signal(s) are calculated and relative amount is calculated by dividing: intensity of signal(s) 1/intensity of signal(s) 2. The proportion or quantitative relation can be expressed as percent value by multiplying with factor 100% (percent)

Conclusions

Of these cell types, 1. and 2. were cultured in commercial serum replacement medium and 3. and 4. were cultured in fetal calf serum containing cell culture medium. Sialic acid composition analysis of these cell culture media are described above in preceeding Examples. It is concluded that low Neu5Gc N-glycan content in cell culture medium leads to low Neu5Gc content of sialylated N-glycans in cell samples. The present results also suggest that in specific culture media Neu5Gc content of stem cell sialylated N-glycans can fall below apparent detection limit.

Example 4

Sialic Acid Linkage Analysis of Cord Blood Mononuclear Cell and Leukocyte Populations, and Bone Marrow Mesenchymal Stem Cells Experimental Procedures N-glycan isolation from cord blood cell populations. Human cord blood mononuclear cells were isolated and divided into CD133$^+$ and CD133$^-$ cell populations as described above. N-linked glycans were detached from cellular glycoproteins and analyzed by mass spectrometry as described above.

α2,3-sialidase digestion. Sialylated N-glycans were treated with *S. pneumoniae* α2,3-sialidase (Glyko, UK) essentially as described previously (Saarinen et al., 1999). The sialic acid linkage specificity was controlled with synthetic oligosaccharides in parallel control reactions, and it was confirmed that in the reaction conditions the enzyme hydrolyzed α2,3-linked but not α2,6-inked sialic acids. After the enzymatic reaction, the glycans were purified and divided into sialylated and non-sialylated fractions and analyzed by mass spectrometry as described above.

Lectin stainings. FITC-labeled *Maackia amurensis* agglutinin (MAA) was purchased from EY Laboratories (USA) and FITC-labeled *Sambucus nigra* agglutinin (SNA) was purchased from Vector Laboratories (UK). Bone marrow derived mesenchymal stem cell lines were cultured as described above. After culturing, cells were rinsed 5 times with PBS (10 mM sodium phosphate, pH 7.2, 140 mM NaCl) and fixed with 4% PBS-buffered paraformaldehyde pH 7.2 at room temperature (RT) for 10 minutes. After fixation, cells were washed 3 times with PBS and non-specific binding sites were blocked with 3% HSA-PBS (FRC Blood Service, Finland) or 3% BSA-PBS (>99% pure BSA, Sigma) for 30 minutes at RT. According to manufacturers' instructions cells were washed twice with PBS, TBS (20 mM Tris-HCl, pH 7.5, 150 mM NaCl, 10 mM CaCl$_2$) or HEPES-buffer (10 mM HEPES, pH 7.5, 150 mM NaCl) before lectin incubation. FITC-labeled lectins were diluted in 1% HSA or 1% BSA in buffer and incubated with the cells for 60 minutes at RT in the dark. Furthermore, cells were washed 3 times 10 minutes with PBS/TBS/HEPES and mounted in Vectashield mounting medium containing DAPI-stain (Vector Laboratories, UK). Lectin stainings were observed with Zeiss Axioskop 2 plus-fluorescence microscope (Carl Zeiss Vision GmbH, Germany) with FITC and DAPI filters. Images were taken with Zeiss AxioCam MRc-camera and with AxioVision Software 3.1/4.0 (Carl Zeiss) with the 400× magnification.

Results

Mass spectrometric analysis of cord blood CD133$^+$ and CD133$^-$ cell N-glycans. Sialylated N-glycans were isolated from cord blood CD133$^+$ and CD133$^-$ cell fractions and analyzed by MALDI-TOF mass spectrometry as described under Experimental procedures, allowing for relative quantitation of individual N-glycan signals.

Figure 4:
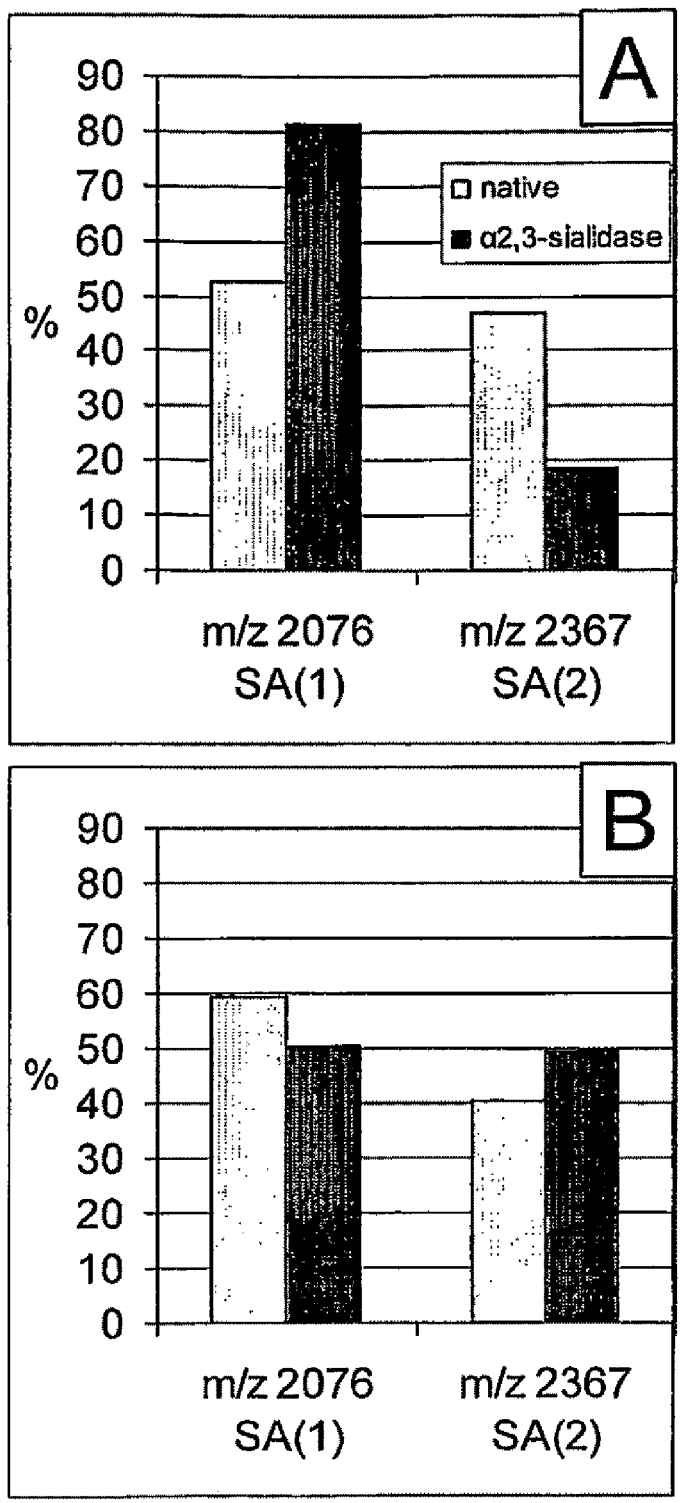
FIG. 4. α2,3-sialidase analysis of sialylated N-glycans isolated from A. cord blood CD133$^+$ cells and B. CD133$^-$ cells. The columns represent the relative proportions of a monosialylated glycan signal at m/z 2076 (SA$_1$) and the corresponding disialylated glycan signal at m/z 2367 (SA$_2$), as described in the text. In cord blood CD133$^-$ cells, the relative proportions of the SA$_1$ and SA$_2$ glycans do not change markedly upon α2,3-sialidase treatment (B), whereas in CD133$^+$ cells the proportion of α2,3-sialidase resistant SA$_2$ glycans is significantly smaller than α2,3-sialidase resistant SA$_1$ glycans (A).

Cord blood CD133$^+$ and CD133$^-$ cell N-glycans are differentially α2,3-sialylated. Sialylated N-glycans from cord blood CD133$^+$ and CD133$^-$ cells were treated with α2,3-sialidase, after which the resulting glycans were divided into sialylated and non-sialylated fractions, as described under Experimental procedures. Both α2,3-sialidase resistant and sensitive sialylated N-glycans were observed, i.e. after the sialidase treatment sialylated glycans were observed in the sialylated N-glycan fraction and desialylated glycans were observed in the neutral N-glycan fraction. The results indicate that cord blood CD133$^+$ and CD133$^-$ cells are differentially α2,3-sialylated. For example, after α2,3-sialidase treatment the relative proportions of monosialylated (SA$_1$) glycan signal at m/z 2076, corresponding to the [M-H]$^-$ ion of NeuAc$_1$Hex$_5$HexNAc$_4$dHex$_1$, and the disialylated (SA$_2$) glycan signal at m/z 2367, corresponding to the [M-H]$^-$ ion of NeuAc$_2$Hex$_5$HexNAc$_4$dHex$_1$, indicate that α2,3-sialidase resistant disialylated N-glycans are relatively more abundant in CD133$^-$ than in CD133$^+$ cells, when compared to α2,3-sialidase resistant monosialylated N-glycans (FIG. 4). It is concluded that N-glycan α2,3-sialylation in relation to other sialic acid linkages including especially α-2,6-sialylation, is more abundant in cord blood CD133$^+$ cells than in CD133$^-$ cells.

In cord blood CD133$^-$ cells, several sialylated N-glycans were observed that were resistant to α2,3-sialidase treatment, i.e. neutral glycans were not observed that would correspond to the desialylated forms of the original sialylated glycans. The results revealing differential α2,3-sialylation of individual N-glycan structures between cord blood CD133$^+$ and CD133$^-$ cells are presented in Table 2. The present results indicate that N-glycan α2,3-sialylation in relation to other sialic acid linkages is more abundant in cord blood CD133$^+$ cells than in CD133$^-$ cells.

Lectin binding analysis of mesenchymal stem cells. As described under Experimental procedures, bone marrow derived mesenchymal stem cells were analyzed for the presence of ligands of α2,3-linked sialic acid specific (MAA) and α2,6-linked sialic acid specific (SNA) lectins on their surface. It was revealed that MAA bound strongly to the cells whereas SNA bound weakly, indicating that in the cell culture conditions, the cells had significantly more α2,3-linked than α2,6-linked sialic acids on their surface glycoconjugates.

Example 5

Enzymatic Modification of Cell Surface Glycan Structures

Experimental Procedures

Enzymatic modifications. Sialyltransferase reaction: Human cord blood mononuclear cells (3×10$^6$ cells) were modified with 60 mU α2,3-(N)-sialyltransferase (rat, recombinant in *S. frugiperda*, Calbiochem), 1.6 μmol CMP-Neu5Ac in 50 mM sodium 3-morpholinopropanesulfonic acid (MOPS) buffer pH 7.4, 150 mM NaCl at total volume of 100 μl for up to 12 hours. Fucosyltransferase reaction: Human cord blood mononuclear cells (3×10$^6$ cells) were modified with 4 mU α1,3-fucosyltransferase VI (human, recombinant in *S. frugiperda*, Calbiochem), 1 μmol GDP-Fuc in 50 mM MOPS buffer pH 7.2, 150 mM NaCl at total volume of 100 μl for up to 3 hours. Broad-range sialidase reaction: Human cord blood mononuclear cells (3×10$^6$ cells) were modified with 5 mU sialidase (*A. ureafaciens*, Glyko, UK) in 50 mM sodium acetate buffer pH 5.5, 150 mM NaCl at total volume of 100 μl for up to 12 hours. α2,3-specific sialidase reaction: Cells were modified with α2,3-sialidase (*S. pneumoniae*, recombinant in *E. coli*) in 50 mM sodium acetate buffer pH 5.5, 150 mM NaCl at total volume of 100 μl. Sequential enzymatic modifications: Between sequential reactions cells were pelleted with centrifugation and supernatant was discarded, after which the next modification enzyme in appropriate buffer and substrate solution was applied to the cells as described above. Washing procedure: After modification, cells were washed with phosphate buffered saline.

Glycan analysis. After washing the cells, total cellular glycoproteins were subjected to N-glycosidase digestion, and sialylated and neutral N-glycans isolated and analyzed with mass spectrometry as described above. For O-glycan analysis, the glycoproteins were subjected to reducing alkaline β-elimination essentially as described previously (Nyman et al., 1998), after which sialylated and neutral glycan alditol fractions were isolated and analyzed with mass spectrometry as described above.

Results

Sialidase digestion. Upon broad-range sialidase catalyzed desialylation of living cord blood mononuclear cells, sialylated N-glycan structures as well as O-glycan structures (data not shown) were desialylated, as indicated by increase in relative amounts of corresponding neutral N-glycan structures, for example $Hex_6HexNAc_3$, $Hex_5HexNAc_4dHex_{0-2}$, and $Hex_6HexNAc_5dHex_{0-1}$ monosaccharide compositions (Table 5). In general, a shift in glycosylation profiles towards glycan structures with less sialic acid residues was observed in sialylated N-glycan analyses upon broad-range sialidase treatment. The shift in glycan profiles of the cells upon the reaction served as an effective means to characterize the reaction results. It is concluded that the resulting modified cells contained less sialic acid residues and more terminal galactose residues at their surface after the reaction.

α2,3-specific sialidase digestion. Similarly, upon α2,3-specific sialidase catalyzed desialylation of living mononuclear cells, sialylated N-glycan structures were desialylated, as indicated by increase in relative amounts of corresponding neutral N-glycan structures (data not shown). In general, a shift in glycosylation profiles towards glycan structures with less sialic acid residues was observed in sialylated N-glycan analyses upon α2,3-specific sialidase treatment. The shift in glycan profiles of the cells upon the reaction served as an effective means to characterize the reaction results. It is concluded that the resulting modified cells contained less α2,3-linked sialic acid residues and more terminal galactose residues at their surface after the reaction.

Sialyltransferase reaction. Upon α2,3-sialyltransferase catalyzed sialylation of living cord blood mononuclear cells, numerous neutral (Table 5) and sialylated N-glycan (Table 4) structures as well as O-glycan structures (data not shown) were sialylated, as indicated by decrease in relative amounts of neutral N-glycan structures ($Hex_5HexNAc_4dHex_{0-3}$ and $Hex_6HexNAc_5dHex_{0-2}$ monosaccharide compositions in Table 5) and increase in the corresponding sialylated structures (for example the $NeuAc_2Hex_5HexNAc_4dHex_1$ glycan in Table 4). In general, a shift in glycosylation profiles towards glycan structures with more sialic acid residues was observed both in N-glycan and O-glycan analyses. It is concluded that the resulting modified cells contained more α2,3-linked sialic acid residues and less terminal galactose residues at their surface after the reaction.

Fucosyltransferase reaction. Upon α1,3-fucosyltransferase catalyzed fucosylation of living cord blood mononuclear cells, numerous neutral (Table 5) and sialylated N-glycan structures as well as O-glycan structures (see below) were fucosylated, as indicated by decrease in relative amounts of nonfucosylated glycan structures (without dHex in the proposed monosaccharide compositions) and increase in the corresponding fucosylated structures (with $n_{dHex}>0$ in the proposed monosaccharide compositions). For example, before fucosylation O-glycan alditol signals at m/z 773, corresponding to the $[M+Na]^+$ ion of $Hex_2HexNAc_2$ alditol, and at m/z 919, corresponding to the $[M+Na]^+$ ion of $Hex_2HexNAc_2dHex$, alditol, were observed in approximate relative proportions 9:1, respectively (data not shown). After fucosylation, the approximate relative proportions of the signals were 3:1, indicating that significant fucosylation of neutral O-glycans had occurred. Some fucosylated N-glycan structures were even observed after the reaction that had not been observed in the original cells, for example neutral N-glycans with proposed structures $Hex_6HexNAc_5dHex_1$ and $Hex_6HexNAc_5dHex_2$ (Table 5), indicating that in α1,3-fucosyltransferase reaction the cell surface of living cells can be modified with increased amounts or extraordinary structure types of fucosylated glycans, especially terminal Lewis x epitopes in protein-linked N-glycans as well as in O-glycans.

Figure 5:
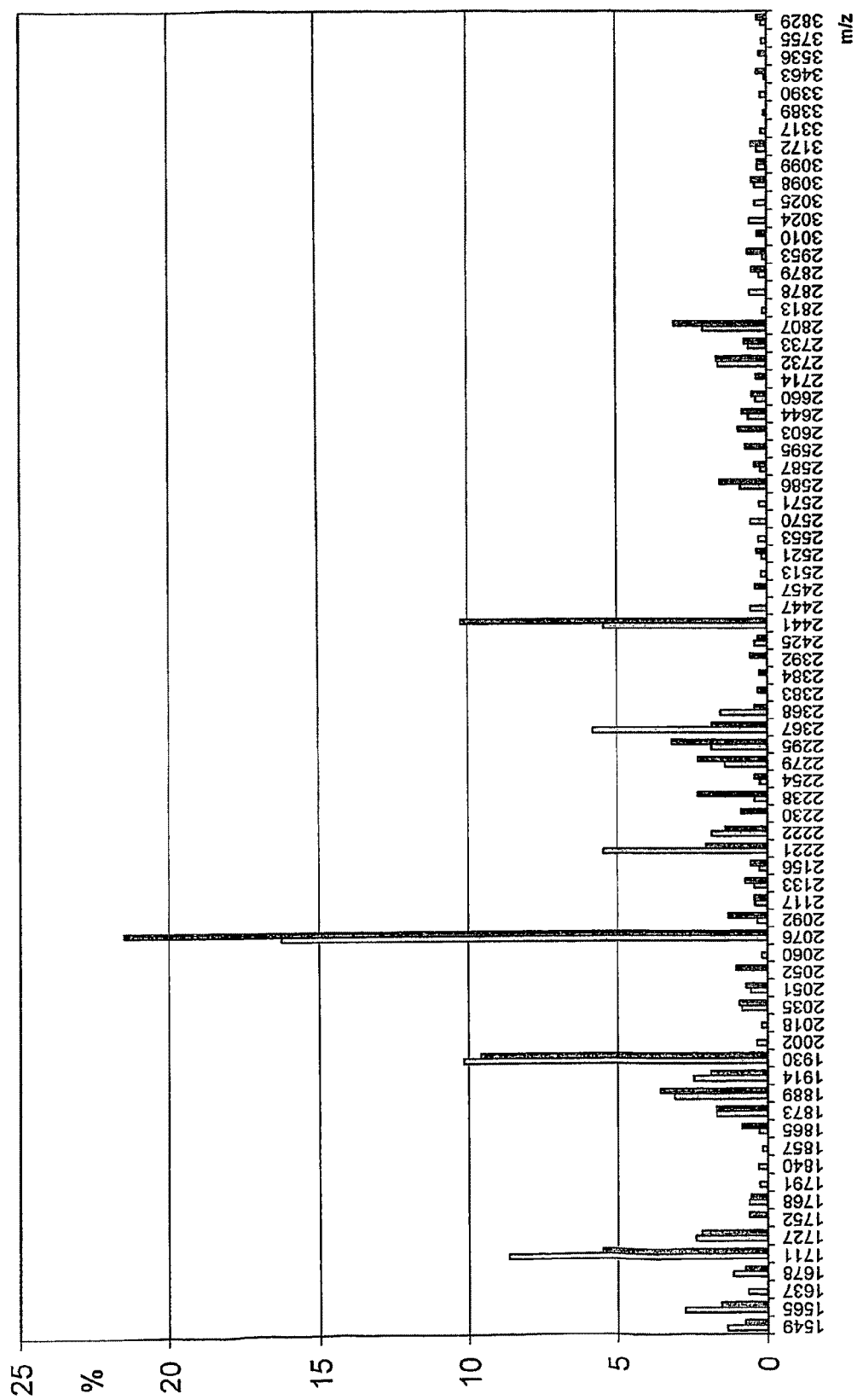
FIG. 5. Cord blood mononuclear cell sialylated N-glycan profiles before (light/blue columns) and after (dark/red columns) subsequent broad-range sialidase and α2,3-sialyltransferase reactions. The m/z values refer to Table 3.

Sialidase digestion followed by sialyltransferase reaction. Cord blood mononuclear cells were subjected to broad-range sialidase reaction, after which α2,3-sialyltransferase and CMP-Neu5Ac were added to the same reaction, as described under Experimental procedures. The effects of this reaction sequence on the N-glycan profiles of the cells are described in FIG. 5. The sialylated N-glycan profile was also analyzed between the reaction steps, and the result clearly indicated that sialic acids were first removed from the sialylated N-glycans (indicated for example by appearance of increased amounts of neutral N-glycans), and then replaced by α2,3-linked sialic acid residues (indicated for example by disappearance of the newly formed neutral N-glycans; data not shown). It is concluded that the resulting modified cells contained more α2,3-linked sialic acid residues after the reaction.

Figure 6:
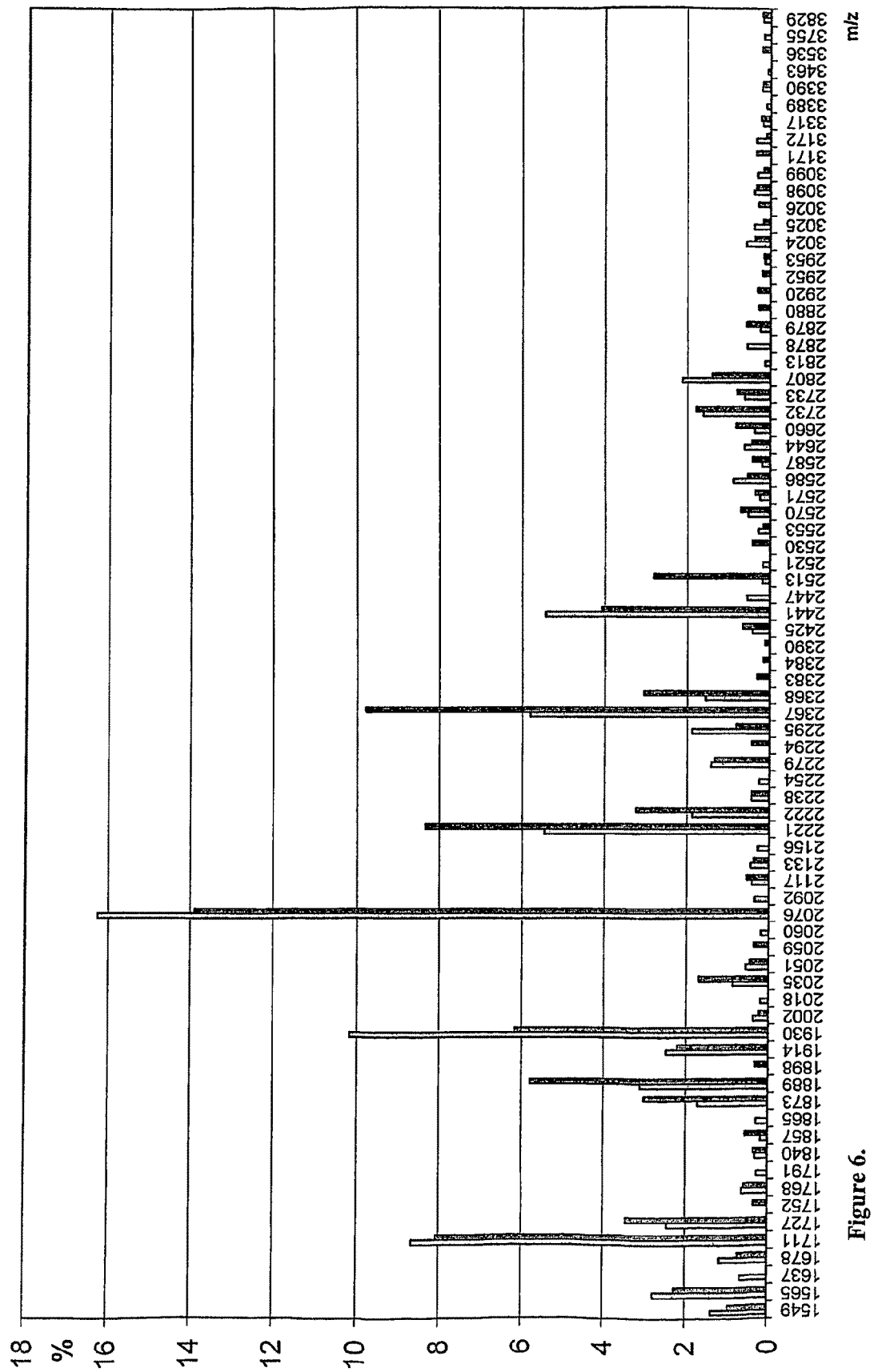
FIG. 6. Cord blood mononuclear cell sialylated N-glycan profiles before (light/blue columns) and after (dark/red columns) subsequent α2,3-sialyltransferase and α1,3-fucosyltransferase reactions. The m/z values refer to Table 3.

Sialyltransferase reaction followed by fucosyltransferase reaction. Cord blood mononuclear cells were subjected to α2,3-sialyltransferase reaction, after which α1,3-fucosyltransferase and GDP-fucose were added to the same reaction, as described under Experimental procedures. The effects of this reaction sequence on the sialylated N-glycan profiles of the cells are described in FIG. 6. The results show that a major part of the glycan signals (detailed in Table 3) have undergone changes in their relative intensities, indicating that a major part of the sialylated N-glycans present in the cells were substrates of the enzymes. It was also clear that the combination of the enzymatic reaction steps resulted in different result than either one of the reaction steps alone.

Different from the α1,3-fucosyltransferase reaction described above, sialylation before fucosylation apparently sialylated the neutral fucosyltransferase acceptor glycan structures present on cord blood mononuclear cell surfaces, resulting in no detectable formation of the neutral fucosylated N-glycan structures that had emerged after α1,3-fucosyltransferase reaction alone (discussed above; Table 5).

Glycosyltransferase-derived glycan structures. We detected that glycosylated glycosyltransferase enzymes can contaminate cells in modification reactions. For example, when cells were incubated with recombinant fucosyltransferase or sialyltransferase enzymes produced in *S. frugiperda* cells, N-glycosidase and mass spectrometric analysis of cellular and/or cell-associated glycoproteins resulted in detection of an abundant neutral N-glycan signal at m/z 1079, corresponding to $[M+Na]^+$ ion of $Hex_3HexNAc_2dHex_1$ glycan component (calc. m/z 1079.38). Typically, in recombinant glycosyltransferase treated cells, this glycan signal was more abundant than or at least comparable to the cells' own glycan signals, indicating that insect-derived glycoconjugates are a very potent contaminant associated with recombinant glycan-modified enzymes produced in insect cells. Moreover, this glycan contamination persisted even after washing of the cells, indicating that the insect-type glycoconjugate corresponding to or associated with the glycosyltransferase enzymes has affinity towards cells or has tendency to resist washing from cells. To confirm the origin of the glycan signal, we analyzed glycan contents of commercial recombinant fucosyltransferase and sialyltransferase enzyme preparations and found that the m/z 1079 glycan signal was a major N-glycan signal associated with these enzymes. Corresponding N-glycan structures, e.g. Manα3(Manα6)Manβ4GlcNAc (Fucα3/6)GlcNAc(β-N-Asn), have been described previously from glycoproteins produced in *S. frugiperda* cells (Staudacher et al., 1992; Kretzchmar et al., 1994; Kubelka et al., 1994; Altmann et al., 1999). As described in the literature, these glycan structures, as well as other glycan structures potentially contaminating cells treated with recombinant or purified enzymes, especially insect-derived products, are potentially immunogenic in humans and/or otherwise harmful to the use of the modified cells. It is concluded that glycan-modifying enzymes must be carefully selected for modification of human cells, especially for clinical use, not to contain immunogenic glycan epitopes, non-human glycan structures, and/or other glycan structures potentially having unwanted biological effects.

Example 6

Detection of O-Acetylated Sialic Acid Containing N-Glycan Structures in Stem Cell and Differentiated Cell Samples, Cell Culture Media, and Biological Reagents Experimental Procedures
Results O-acetylated sialic acids containing sialylated N-glycans in cultured cells. N-glycans were isolated, and sialylated and neutral glycans analyzed with mass spectrometry as described above. The presence of O-acetylated glycoconjugates, especially O-acetylated sialic acids containing N-glycans, were detected in cord blood mesenchymal stem cells grown in differentiating cell culture medium that contained horse serum. Primary diagnostic signals used for detection of O-acetylated sialic acid containing sialylated N-glycans were $[M-H]^-$ ions of $Ac_1NeuAc_1Hex_5HexNAc_4$, $Ac_1NeuAc_2Hex_5HexNAc_4$, and $Ac_2NeuAc_2Hex_5HexNAc_4$, at calculated m/z 1972.7, 2263.8, and 2305.8, respectively.

O-acetylated sialic acids containing sialylated N-glycans in biological reagents. As presented in detail in Example 2, among the studied reagents especially horse serum for cell culture, horse serum containing cell culture media, and murine monoclonal antibody preparations were indicated to contain N-glycans with O-acetylated sialic acid residues.
Conclusions The present mass spectrometric method proved efficient in detecting potentially O-acetylated sialic acids containing glycoconjugates in biological materials, especially biological reagents used in cell culture. The present results indicate that cells grown in O-acetylated sialic acid containing cell culture media can be contaminated with O-acetylated sialic acids or glycoconjugates. It is suggested that the present method can be used to detect O-acetylated glycoconjugate levels in biological samples, especially cultured cells.

Example 7

Cytidine Monophospho-N-Acetylneuraminic Acid (CMP-Neu5Ac) Hydroxylase (CMAH) Gene Expression in CD34+/CD133+ Cells Experimental Procedures Cells. Mononuclear cells (MNC) were isolated form cord blood (CB) by Ficoll-Hypaque density gradient (Amersham Biosciences, Piscataway, USA). CD34+/CD133+ cells were enriched through positive immunomagnetic selection using Direct CD34 Progenitor Cell Isolation Kit or CD133 Cell Isolation Kit and MACS affinity columns (Miltenyi Biotec, Bergisch Gladbach, Germany). CD34+/CD133+ cells were subjected to 2 rounds of separation. The negative cells from the same CB unit were collected for control purposes.

RNA isolation. Total RNA from up to $2 \times 10^7$ cells was purified with RNeasy Mini Kit (Qiagen GmbH, Hilden, Germany) according to the manufacturer's instructions. Yield and quality of the RNA was measured by spectrophotometric analysis. Each sample was assessed for the integrity of RNA by discrimination of 18S and 28S ribosomal RNA on 1% agarose using ethidium bromide for visualization.

Microarray analysis. Total RNA from each sample was used to prepare biotinylated target RNA, with minor modifications from the manufacturer's recommendations (http://www.affymetrix.com/support/technical/manual/expression_manual.affx). In brief, first-strand cDNA was generated from 100 ng of total RNA using a T7-linked oligo(dT) primer. After the first cDNA synthesis cycle, in vitro transcription was performed with unlabeled ribonucleotides. A second round of cDNA synthesis was then performed followed by in vitro transcription with biotinylated UTP and CTP (Enzo Diagnostics, Farmingdale, USA). Cleanup of double-stranded cDNA was performed using Pellet Paint® Co-Precipitant (Novagen, Madison, USA) instead of glycogen. Standard Affymetrix hybridization cocktail was added to 15 µg fragmented cRNA. After overnight hybridization using Affymetrix GeneChip Instrument System (Affymetrix, Santa Clara, USA), arrays were washed, stained with streptavidin-phycoerythrin and scanned on Affymetrix GeneChip Scanner 3000. Experiments were performed using Affymetrix Human Genome U133 Plus 2.0 oligonucleotide arrays (http://www.affymetrix.com/products/arrays/specific/hgu133plus.affx).

Quantitative qRT-PCR analysis. To confirm the information obtained from the microarray data, the CMAH gene was subjected to qRT-PCR analysis using pools with 3 samples in each. Analysis was performed on 2 biological replicates. Total RNA was DNase-treated with DNA-free™ Kit (Ambion Inc., Austin, USA), and reverse transcription was performed using High-Capacity cDNA Archive Kit with RNase Inhibitor Mix (Applied Biosystems, Foster City, USA) in a final volume of 100 µl. Thermal cycling conditions for reverse transcription were 25° C. for 10 minutes and 37° C. for 120 minutes on GeneAmp® PCR System 9700 (Applied Biosystems).

For the polymerase chain reaction (PCR), the template was added to PCR mix consisting of 12.5 µl TaqMan Universal PCR Master Mix containing Uracil N-glycosylase for PCR carry-over prevention, 1.25 µl of TaqMan Assays-On-Demand Gene expression probe (Hs00186003_ml) and diethyl pyrocarbonate-treated water (Ambion, Inc.). Samples were assayed in triplicate in a total volume of 25 µl. The qRT-PCR thermal cycling conditions were as follows: an initial step at 50° C. for 2 min for Uracil N-glycosylase activation; 95° C. for 10 min; and 40 cycles of 15 s at 95° C. and 1 min at 60° C.

A standard curve for serial dilutions of GAPDH rRNA was similarly constructed. GAPDH was chosen to internal control because its expression levels had no variance between the samples in the microarray analysis. Changes in fluorescence were monitored using the ABI PRISM 7000 Sequence Detection System, and raw data were analyzed by Sequence Detection System 1.1 Software (Applied Biosystems). The relative standard curve method was used to balance the variation in the amount of cDNA and to compensate for different levels of inhibition during reverse transcription and PCR.

Results

Microarray results. Altogether four probe sets were used in the expression analysis of the CMAH gene. In cord blood CD34+ cells, only one transcript (205518_s_at) was expressed by 3.0-fold overexpression. In cord blood CD133+ cells, three transcripts were expressed. Two of these (210571_s_at and 229604_at) were expressed in CD133+ cells but were completely absent in CD133− cells. Transcript 210571_s_at was overexpressed by 9.2-fold, and transcript 229604_at by 4.9-fold. The transcript 205518_s_at, overexpressed in CD34+ cells, was also highly overexpressed in CD133+ cells (7.0-fold).

qRT-PCR results. The microarray results were confirmed by quantitative RT-PCR analysis. CMAH gene was overexpressed in CD34+ cells by 5.9-fold and in CD133+ cells by 4.4-fold. The microarray and qRT-PCR results are compared in Table 7.

Example 8

Cloning and Sequence Analysis of Human CMP-N-Acetylneuraminic Acid Hydroxylase (CMAH) cDNA Experimental Procedures To clone human CMAH cDNA, total RNA from human cord blood mononuclear and Lin− cells was isolated using the RNeasy mini kit (Qiagen, Hilden, Germany). 5 µg of total RNA was reverse transcribed with the SuperScript III First-Strand Synthesis System for RT-PCR (Invitrogen, Carlsbad, Calif.). A −RT control sample omitting the reverse transcriptase was also prepared for each sample to control genomic DNA contamination. Conventional reverse transcription (RT)-PCR was conducted using five pairs of CMAH specific sense and antisense primers designed from the sequence information in GenBank accession number D86324. The sequence of the primer pairs are presented in Table 8. One primer pair was designed to amplify the complete cDNA sequence (CMAH_UP1, CMAH_DO1, see Table 8) and the other four were designed for amplification of shorter, overlapping fragments of the full-length cDNA sequence. To control the integrity of the cDNA, RT-PCR with human β-2-microglobulin specific primers was performed (sequence in Table 8). All oligonucleotides were synthesized by Sigma Genosys (Haverhill, Suffolk, UK). The RT-PCR was performed in a 25 µl final volume composing of 0.5-1 units of DyNAzyme EXT DNA polymerase (Finnzymes, Espoo, Finland), 1× DyNAzyme EXT Buffer (with 15 mM $MgCl_2$), 0.2 mM dNTPs, 0.2 µM primers, 2% DMSO, and 1.0-2.01 template. Annealing was performed through a temperature gradient for the CMAH specific primers (55-68° C.) and at 58° C. for β-2-microglobulin. Amplification was performed for 40-45 cycles. A negative control was included for each primer pair, in which template cDNA was omitted and replaced with water. The PCR products were analyzed by agarose gel electrophoresis and visible bands were excised from the gel and purified (Minelute gel extraction kit; Qiagen, Hilden, Germany). The purified PCR products were ligated into pGEM-T easy vector (Promega, Madison, Wis.), and recombinant clones (plasmids prepared with the GenElute plasmid miniprep kit, Sigma-Aldrich, St. Louis, Mo.) were isolated for subsequent sequencing analysis. Several clones from each ligation were sequenced and sequencing was accomplished using automated sequencing (ABI Prism Automated Fluorescence Sequencer) with the universal sequencing primers M13 forward and M13 reverse and additionally gene-specific primers for long inserts. Sequence assembly of the complete inserts was accomplished using programs available at the Finnish Center for Scientific Calculation (CSC) web page (www.csc.fi). Sequence alignment and homology comparison was done with Clustal W and BLAST programs.

Results

Sequence analysis of human CMP-N-acetylneuraminic acid hydroxylase (CMAH) gene cloned from umbilical cord blood cells. RT-PCR with a primer pair designed to amplify full-length CMAH cDNA revealed one major PCR product and some weaker products from human cord blood mononuclear and Lin− cell cDNA. Sequencing of the major PCR product produced one full-length cDNA sequence of 1972 bp. The nucleotide sequence and derived amino acid sequence of 501 amino acid residues in the open-reading frame (frame 2) is presented in FIG. 7A. Sequencing revealed the other weaker PCR products to be immature cDNA variants with multiple introns still incorporated in the reverse transcribed cDNA molecule (data not shown). Sequencing of the RT-PCR products with the other four primer pairs, designed for amplification of shorter, overlapping fragments of the full-length cDNA sequence, verified the full-length sequence.

Figure 8:
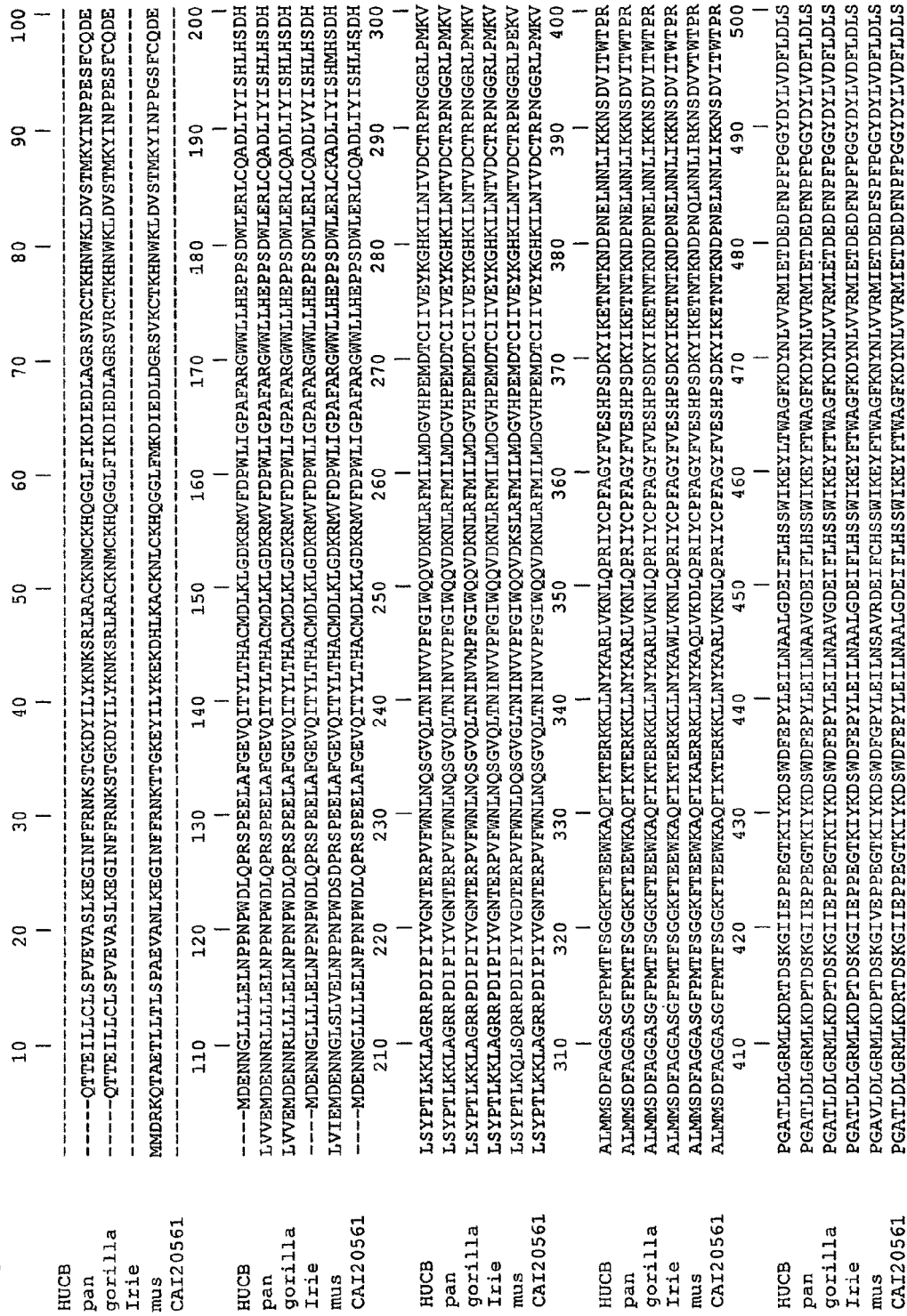
FIG. 8. ClustalW alignment of CMAH proteins. HUCB=human umbilical cord blood, pan=*pan paniscus* (pygmy chimpanzee), gorilla=*gorilla gorilla* (western gorilla), Irie=GenBank accession number D86324 (human HeLa cell CMAH), mus=*mus musculus* (mouse), GenBank accession number CAI20561 is a predicted splice variant of human CMAH.

The 5'-end of the CMAH cDNA nucleotide sequence was analyzed carefully for the presence of a 92 bp sequence corresponding to exon 6 of the mouse and monkey CMAH genes (Chou et al. 1998; Irie et al. 1998). Consistent with previous observations concerning human CMAH cDNA, the human umbilical cord blood CMAH cDNA was also missing this fragment and thus a truncated N-terminus of the protein is produced as compared to mouse and monkey (FIG. 8). The 5'-end sequence and translation in all three frames is presented in FIG. 7B.

The cloned CMAH cDNA from human umbilical cord blood cells was analyzed for sequence homology to CMAH genes available in the GenBank. Surprisingly, the cord blood CMAH cDNA is different from the previously published human CMAH cDNA. A 200 bp deletion in the region encoding the C-terminus of the protein produces a frame-shift yielding a 20 aa longer peptide sequence as compared to e.g. the predicted protein from human HeLa cell CMAH cDNA (Irie et al. 1998). ClustalW alignment with CMAH proteins revealed the derived cord blood CMAH protein to have a homologous C-terminus with monkey CMAH proteins (FIG. 8). On amino acid level, human umbilical cord blood CMAH is 98% homologous to monkey CMAH, 97% homologous to human HeLa cell CMAH (Irie et al. 1998) and 86% homologous to the mouse CMAH ortholog (FIG. 8). Surprisingly, an in silico predicted possible human splice variant of the CMAH protein (accession number CA120561) was found in the GenBank with 99% sequence homology to human umbilical cord blood CMAH (FIG. 8).

Figure 9:
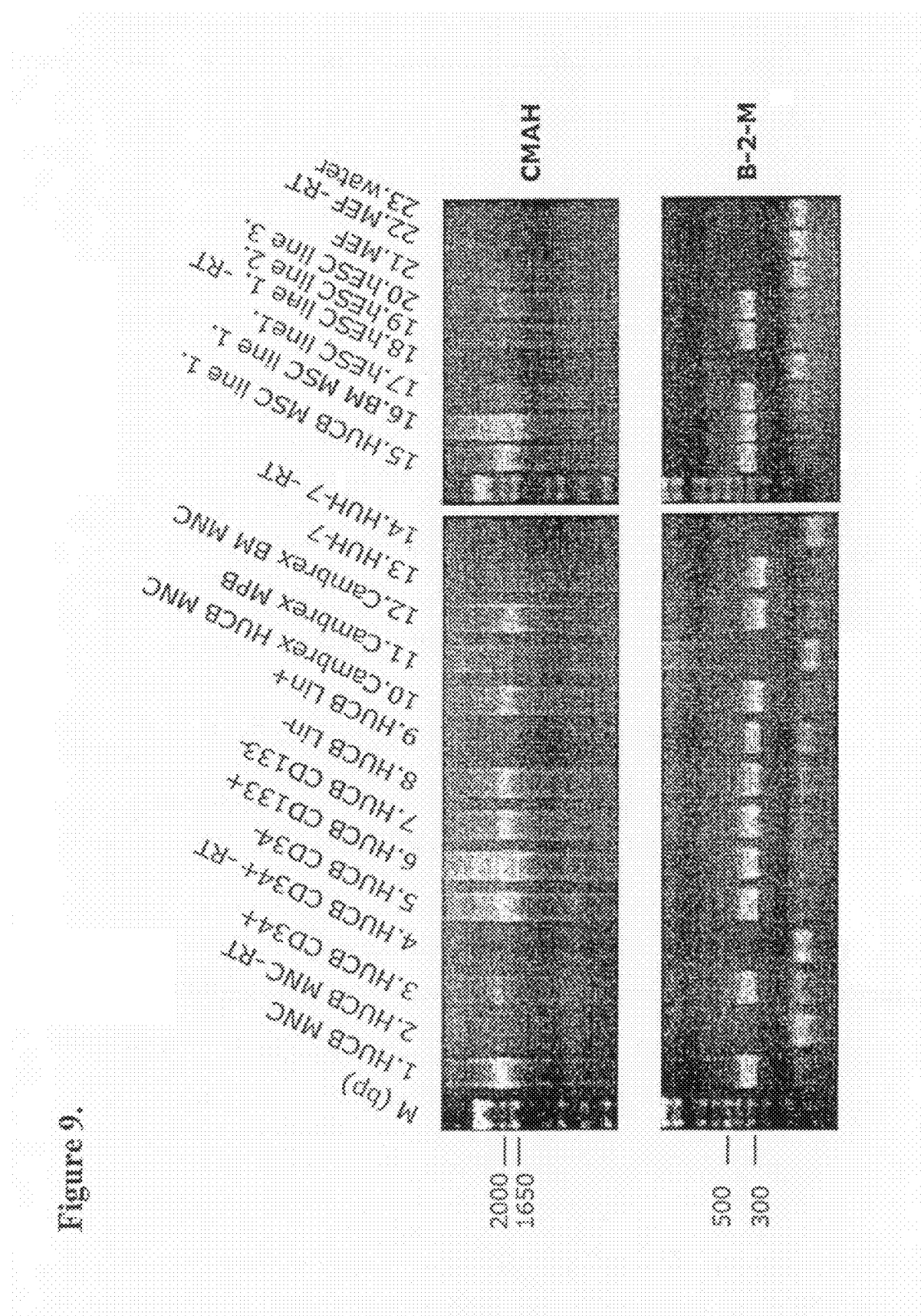
FIG. 9. RT-PCR analysis of CMP-N-acetylneuraminic acid hydroxylase (CMAH) and β-2-microglobulin (B2M) mRNA expression in different human stem cell sources. M=molecular marker. HUCB=human umbilical cord blood, MNC=mononuclear cells, MPB=progenitor cells mobilized from the bone marrow, MSC=mesenchymal cells, hESC=human embryonic stem cells, MEF=mouse feeder cells.

Expression of CMAH mRNA in different stem cell sources. A cDNA panel was prepared containing different cDNA templates from a variety of human adult and embryonal stem cell sources. RT-PCR with primers for the full-length CMAH cDNA was performed and the integrity of the cDNA was subsequently controlled with RT-PCR with human β-2-microglobulin specific primers. The results are presented in FIG. 9 and Table 9. Full-length CMAH cDNA could successfully be amplified from human umbilical cord blood stem cell sources (CD34+, CD133+ and Lin− cells) and from mesenchymal stem cells of both human bone marrow and umbilical cord blood origin. Human embryonic stem cells (three different lines) expressed detectable amounts of CMAH mRNA (FIG. 9 and Table 9). Strikingly, a dramatic difference in CMAH mRNA expression was detected between human umbilical cord blood Lin− and Lin+ cells (FIG. 9).

Example 9

Literature references are numbered in parenthesis and listed at the end of the Example.
Methods
Human embryonic stem cell lines (hESC). The generation of the four human hESC lines FES 21, FES 22, FES 29, and FES 30 has been described (9). Two of the analysed cell lines in the present work were initially derived and cultured on mouse embryonic fibroblasts feeders (MEF; 12-13 pc fetuses of the ICR strain), and two on human foreskin fibroblast feeder cells (HFF; CRL-2429 ATCC, Mananas, USA). For the present studies all the lines (FES 21, FES 22, FES 29, and FES 30) were transferred on HFF feeder cells treated with mitomycin-C (1 µg/ml; Sigma-Aldrich) and cultured in serum-free medium (Knockout™ D-MEM; Gibco® Cell culture systems, Invitrogen, Paisley, UK) supplemented with 2 mM L-glutamin/penicillin/streptomycin (Sigma-Aldrich), 20% Knockout serum replacement (Gibco), non-essential amino acids (Gibco), 0.1 mM β-mercaptoethanol (Gibco), insulin-transferrin selenium supplement (ITS; Sigma-Aldrich) and 4 ng/ml basic FGF (bFGF; Sigma/Invitrogen). To induce the formation of embryoid bodies (EB) the hESC colonies were first allowed to grow for 10-14 days whereafter the colonies were cut in small pieces and transferred on non-adherent Petri dishes to form suspension cultures. The formed EB were cultured in suspension for the next 10 days in standard culture medium (see above) without bFGF. For further differentiation into stage 3 differentiated cells, EB were transferred onto gelatin-coated (Sigma-Aldrich) adherent culture dishes in media consisting of DMEM/F12 mixture (Gibco) supplemented with ITS, fibronectin (Sigma), L-glutamine and antibiotics. The attached cells were cultured for 10 days whereafter they were harvested. The cells were collected mechanically, washed, and stored frozen prior to glycan analysis.

Bone marrow derived mesenchymal stem cell lines. Bone marrow derived MSC were obtained as described (10). Briefly, bone marrow obtained during orthopedic surgery was cultured in minimum essential alpha-medium (α-MEM), supplemented with 20 mM HEPES, 10% FBS, penicillin-streptomycin and 2 mM L-glutamine (all from Gibco). After a cell attachment period of 2 days the cells were washed with $Ca^{2+}$ and $Mg^{2+}$ free PBS (Gibco), subcultured further by plating the cells at a density of 2000-3000 $cells/cm^2$ in the same media and removing half of the media and replacing it with fresh media twice a week until near confluence. For analysis of the effects of human serum on Neu5Gc decontamination, the cells were cultured for 3 weeks in the media where FBS was replaced by 10% human serum.

Flow cytometric analysis of mesenchymal stem cell phenotype. Bone marrow MSC were phenotyped by flow cytometry (FACSCalibur, Becton Dickinson). Fluorescein isothicyanate (FITC) or phycoerythrin (PE) conjugated antibodies against CD13, CD14, CD29, CD34, CD44, CD45, CD49e, CD73 and HLA-ABC (all from BD Biosciences, San Jose, Calif.), CD105 (Abcam Ltd., Cambridge, UK) and CD133 (Miltenyi Biotec) were used for direct labeling. Appropriate FITC- and PE-conjugated isotypic controls (BD Biosciences) were used. Unconjugated antibodies against CD90 and HLA-DR (both from BD Biosciences) were used for indirect labeling. For indirect labeling FITC-conjugated goat anti-mouse IgG antibody (Sigma-aldrich) was used as a secondary antibody. The cells were negative for CD14, CD34, CD45 and HLA-DR and positive for CD13, CD29, CD44, CD90, CD105 and HLA-ABC.

Osteogenic differentiation of mesenchymal stem cells. To induce the osteogenic differentiation of the bone marrow derived MSC the cells were seeded in their normal proliferation medium at a density of $3\times10^3/cm^2$ on 24-well plates (Nunc). The next day the medium was changed to osteogenic induction medium which consisted of α-MEM (Gibco) supplemented with 10% FBS (Gibco), 0.1 µM dexamethasone, 10 mM β-glycerophosphate, 0.05 mM L-ascorbic acid-2-phosphate (Sigma-Aldrich) and penicillin-streptomycin (Gibco). The cells were cultured for three weeks changing the medium twice a week before preparing samples for glycome analysis.

Cell harvesting for glycome analysis. 1 ml of cell culture medium was saved for glycome analysis and the rest of the medium removed by aspiration. Cell culture plates were washed with PBS buffer pH 7.2. PBS was aspirated and cells scraped and collected with 5 ml of PBS (repeated two times). At this point small cell fraction (10 µl) was taken for cell-counting and the rest of the sample centrifuged for 5 minutes at 400 g. The supernatant was aspirated and the pellet washed in PBS for an additional 2 times. The cells were collected with 1.5 ml of PBS, transferred from 50 ml tube into 1.5 ml collection tube and centrifuged for 7 minutes at 5400 rpm. The supernatant was aspirated and washing repeated one more time. Cell pellet was stored at −70° C. until analysis.

Glycan isolation. Asparagine-linked glycans were detached from cellular glycoproteins by *F. meningosepticum* N-glycosidase F digestion (Calbiochem, USA) essentially as described (21). The released glycans were purified for analysis mainly by miniaturized solid-phase extraction steps as described (T.S., A.H., M.B., C.O., M.M., J.N., T.O., T.T., J.S., J.L. et al., manuscript submitted).

Mass spectrometry. MALDI-TOF mass spectrometry was performed with a Bruker Ultraflex TOF/TOF instrument (Bruker, Germany) essentially as described (22). Relative molar abundancies of neutral and sialylated glycan components can be assigned based on their relative signal intensities in the mass spectra (23). The mass spectrometric fragmentation analysis was done according to manufacturer's instructions.

Neu5Gc-specific antibody procedures. The Neu5Gc-specific monoclonal antibody P3Q against the glycolipid antigen Neu5Gcα3LacCer (GM3Gc) was a kind gift from Dr. Ana Maria Vázquez and Ernesto Moreno from the Center of Molecular Immunology, Havana, Cuba. It is essentially similar in binding specificity as described (7,8) and was characterized to have binding specificity also against the Neu5Gcα3nLc₄Cer glycolipid structure by binding to glycolipid standard molecules on thin-layer chromatography plates, suggesting that it may also bind to similar epitopes on glycoproteins. The P3Q antibody was used for detection of N-glycolylneuraminic acid-containing fractions according to the following procedure. Mixtures of glycolipids were separated on TLC plates after which the plates were covered with a plastic layer as described (24). The plates were then incubated in 2% BSA in PBS for 1 h and overlaid with the anti-N-glycolyl antibody diluted with 2% BSA in PBS. After 2 h the plates were washed with PBS and overlaid with a second antibody, HRP-labeled (horseradish peroxidase) antibody (rabbit antihuman IgG γ chains, P.0214, DAKO, Denmark) diluted with 2% BSA in PBS. After additional 2 h the plates were washed with PBS and the binding fractions were visualized using 0.02% 3,3'-diaminobenzidine tetrahydrochloride (DAB) in PBS containing 0.03% $H_2O_2$. All steps were performed at room temperature. The P3 antibody was confirmed to bind strongly to N-glycolyl containing glycolipids and in higher concentrations also to sulfated glycolipids.

Immunohistochemistry. Bone marrow MSC on passages 9-14 were grown on 0.01% poly-L-lysine (Sigma, USA) coated glass 8-chamber slides (Lab-TekII, Nalge Nunc, Denmark) at 37° C. with 5% $CO_2$ for 2-4 days. After culturing, cells were rinsed 5 times with PBS (10 mM sodium phosphate, pH 7.2, 140 mM NaCl) and fixed with 4% PBS-buffered paraformaldehyde pH 7.2 at room temperature (RT) for 10 minutes, followed by washings 3 times 5 minutes with PBS. Some MSC samples were extracted with 0.1% Triton X-100 (Sigma) in PBS for 5 minutes at RT before blocking. Additionally, specificity of the staining was confirmed by sialidase treatment after fixation. Briefly, fixed MSC samples were incubated with 10 mU of sialidase (*Arthrobacter ureafaciens*, Glyko, UK) in 50 mM sodium acetate buffer pH 5.5 over night at 37° C. After detergent extraction or sialidase treatment, cells were washed 3 times with PBS. After fixation and different treatments the non-specific binding sites were blocked with 3% HSA-PBS (FRC Blood Service, Finland) for 30 minutes at RT. Primary antibodies were diluted in 1% HSA-PBS and incubated for 60 minutes at RT, followed by washings 3 times for 10 minutes with PBS. Secondary antibody, FITC-labeled goat-anti-mouse (Sigma) was diluted 1:300 in 1% HSA-PBS and incubated for 60 minutes at RT in the dark. Furthermore, cells were washed 3 times 5-10 minutes with PBS and mounted in Vectashield mounting medium containing DAPI-stain (Vector Laboratories, UK). Immunostainings were analyzed with Zeiss Axioskop 2 plus-fluorescence microscope (Carl Zeiss Vision GmbH, Germany) with FITC and DAPI filters. Images were taken with Zeiss AxioCam MRc-camera and with AxioVision Software 3.1/4.0 (Carl Zeiss) with 400× magnification.

Biological reagents. Bovine serum apotransferrin and fetuin were from Sigma-Aldrich.

Results

Figure 10:
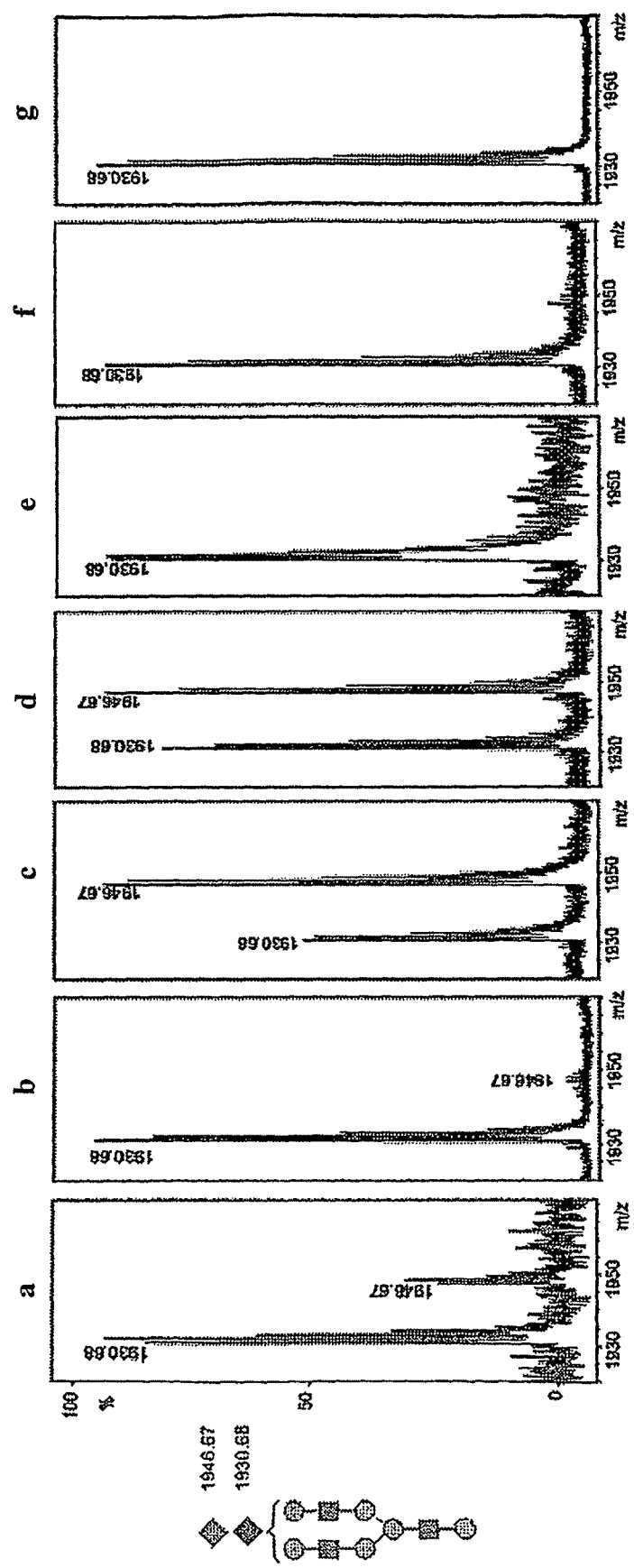
FIG. 10. MALDI-TOF mass spectrometric detection of representative sialylated N-glycans containing Neu5Gc. a hESC grown on human feeder cells in serum replacement medium, b MSC grown in FBS containing medium, c serum replacement cell culture medium, d bovine serum transferrin, e MSC culture medium with FBS, and f fetuin isolated from FBS. The mass-to-charge ratio (m/z) and relative molar abundancy (%) of the observed glycans is indicated on the x- and y-axes of the panels, respectively. The glycan signals at m/z 1946.67 (upper panel), corresponding to the [M-H]$^-$ ion of Neu5Gc$_1$Hex$_5$HexNAc$_4$, as well as m/z 2237.77 and m/z 2253.76 (lower panel), corresponding to the [M-H]$^-$ ions of Neu5Gc$_1$Neu5Ac$_1$Hex$_5$HexNAc$_4$ and Neu5Gc$_2$Hex$_5$HexNAc$_4$, respectively, are typical Neu5Gc-containing N-glycan signals. In contrast, glycan signals at m/z 1930.88 (upper panel), corresponding to the [M-H]$^-$ ion of Neu5Ac$_1$Hex$_5$HexNAc$_4$, as well as m/z 2221.78 (lower panel), corresponding to the [M-H]$^-$ ion of Neu5Ac$_2$Hex$_5$HexNAc$_4$, do not contain Neu5Gc. Schematic N-glycan structures corresponding to these signals are depicted on the left: light yellow circles, hexose (Hex); dark grey squares, N-acetylhexosamine (HexNAc); dark red diamonds, Neu5Ac; light blue diamonds, Neu5Gc.
Figure 10:
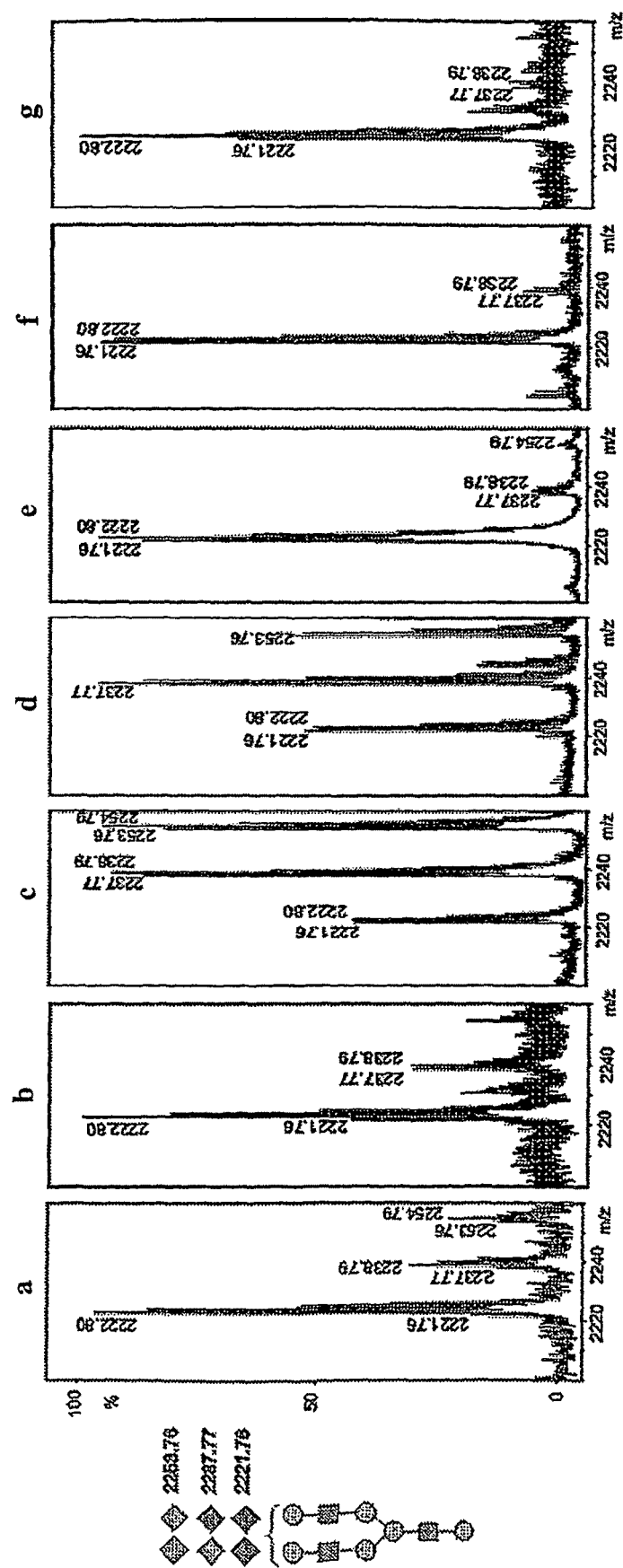

Mass spectrometric analysis of stem cell glycan structures. Four hESC lines, four bone marrow derived MSC lines, cells differentiated from these stem cells, as well as the culture media and supplements used were analyzed. Protein-incorporated Neu5Gc was analyzed by enzymatically detaching asparagine-linked glycans (N-glycans) from total cellular or media proteins, fractionating the released glycans into neutral and acidic N-glycan fractions, and analyzing them by matrix-assisted laser desorption-ionization (MALDI-TOF) mass spectrometry as described in FIG. 10. The identification of Neu5Gc was based on detection of sialic acid residues with 16 Da larger mass than the human-type sialic acid, N-acetylneuraminic acid (Neu5Ac).

Glycan signals indicating the presence of Neu5Gc were detected in all the four different hESC lines cultured in commonly used hESC serum replacement medium on human feeder cell layers (FIG. 10A). When these glycans were subjected to mass spectrometric fragmentation analysis, they produced fragment ions corresponding to Neu5Gc (data not shown). Similar Neu5Gc structures as in hESC were observed in all the MSC lines cultured in FBS containing culture medium (FIG. 10B), indicating that in addition to hESC, also bone marrow derived MSC are susceptible to Neu5Gc contamination.

Figure 11:
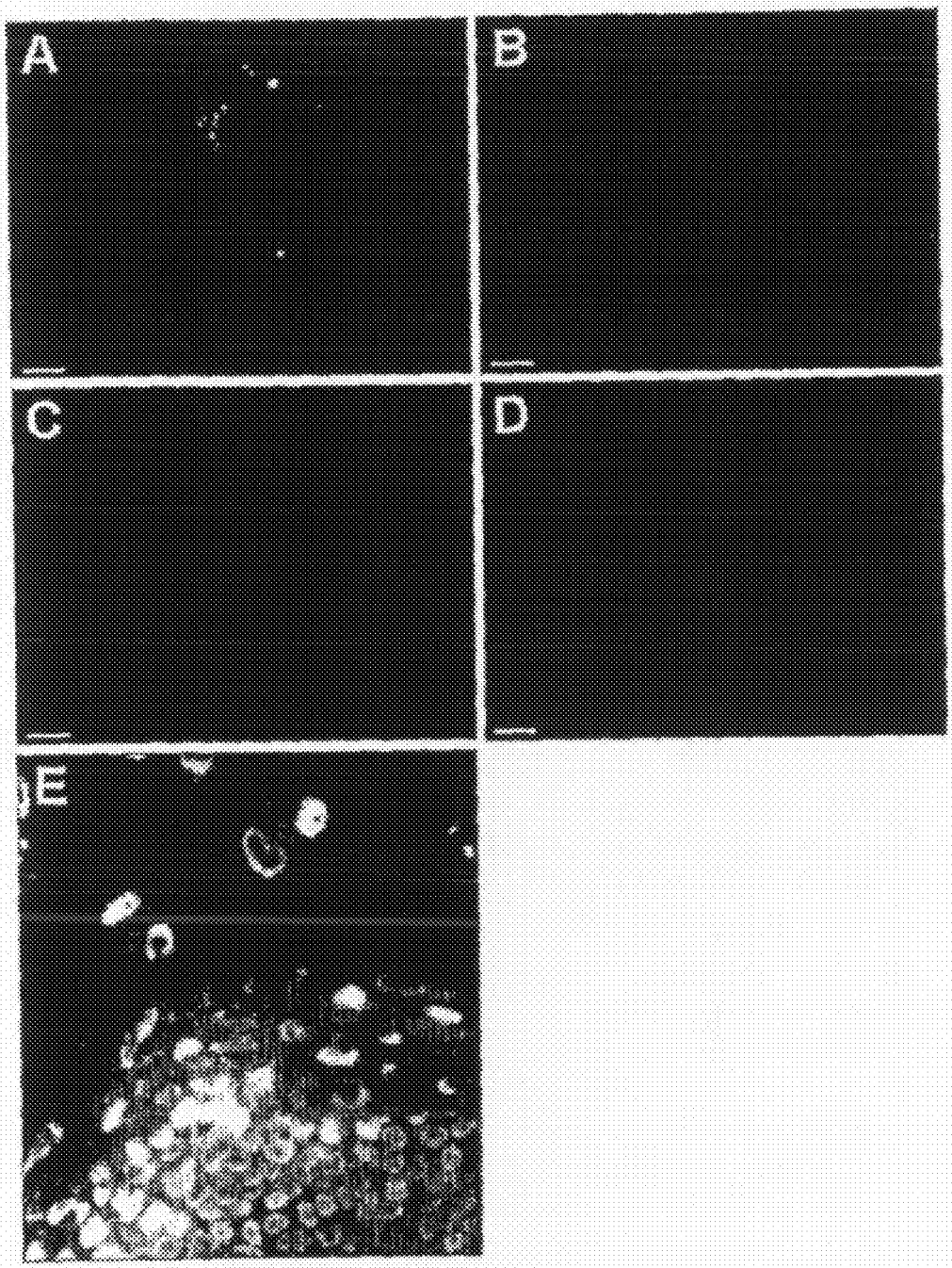
FIG. 11. Immunochemical detection of Neu5Gc in bone-marrow derived MSC line: A. cultured in the presence of FBS by Neu5Gc-specific antibody, B. after detergent extraction, C. after sialidase treatment, decreased staining indicates that antibody binding was dependent on sialic acids such as Neu5Gc, and D. negative control without primary antibody. Scale bar in A-D: 20 μm. E. hESC line FES 30 grown on mouse feeder cells and in the presence of serum replacement cell culture supplement stained by the Neu5Gc-specific antibody. Neu5Gc epitopes were detected in both hESC (densely growing cells in the lower part of the picture) and feeder cells.

Immunohistochemical detection of Neu5Gc in stem cells. To verify the results obtained by mass spectrometry immunohistochemical analyses using a Neu5Gc-specific monoclonal antibody (7, 8) against the glycolipid antigens Neu5Gcα3LacCer and Neu5Gcα3nLc$_4$Cer were performed (FIG. 11). Glycans containing Neu5Gc were detected on both bone marrow derived MSC (FIGS. 11A-D) and hESC (FIG. 11E). Cell permeabilization and extraction with detergent at room temperature abolished the staining suggesting antigen localization in detergent-soluble areas on the cell surface (FIG. 11B).

Analysis of cell culture media for sources of Neu5Gc. To identify the cell culture media components contributing to Neu5Gc contamination, the culture media and their main protein components were analyzed. The hESC samples were cultured on human fibroblast feeder cells in commercial serum-free medium (9). The analysis showed that the medium contained significant amounts of Neu5Gc (FIG. 10C) that seems to be derived from bovine serum transferrin (FIG. 10D), a major component of the commercial serum replacement medium supplement (6). MSC were cultured in standard cell culture medium (α-MEM) supplemented with FBS (10). Also the MSC medium contained Neu5Gc structures (FIG. 10E). However, the relative Neu5Gc levels of N-glycans in FBS were lower than in serum replacement medium or in bovine transferrin. Further, a glycoprotein component of FBS, fetuin (FIG. 10F) contained considerably less Neu5Gc than transferrin suggesting that Neu5Gc contents of animal-derived proteins vary even within an animal species. Taken together, all the media used in stem cell culture contained Neu5Gc, but there were significant differences in the relative concentrations. Surprisingly, the commercial serum replacement medium proved to be a more potent source of Neu5Gc than FBS. The relative Neu5Gc contents in the culture media correlated with the observed high Neu5Gc levels in hESC (FIG. 10A) and significantly lower Neu5Gc levels in MSC (FIG. 10B).

Neu5Gc in stem cell progeny. To determine whether the progeny of Neu5Gc-containing hESC would be permanently contaminated by Neu5Gc, hESC were differentiated into embryoid bodies (EB) and further into stage 3 spontaneously differentiated cells. Embryoid bodies (EB) were cultured in the same medium as hESC (without bFGF) in the absence of feeder cells, and further differentiated cells on gelatin-coated dishes in media supplemented with insulin-transferrin-selenium supplement (ITS) and fibronectin (for details see Methods). The Neu5Gc content was found to decrease during differentiation into EB, and no Neu5Gc was detected in stage 3 differentiated cells. The findings suggested that Neu5Gc contamination in hESC was reversible and that Neu5Gc could be gradually removed from hESC progeny in cell culture. Furthermore, the results suggested that hESC differentiation diminished the susceptibility of the cells to Neu5Gc contamination from the culture medium.

Figure 12:
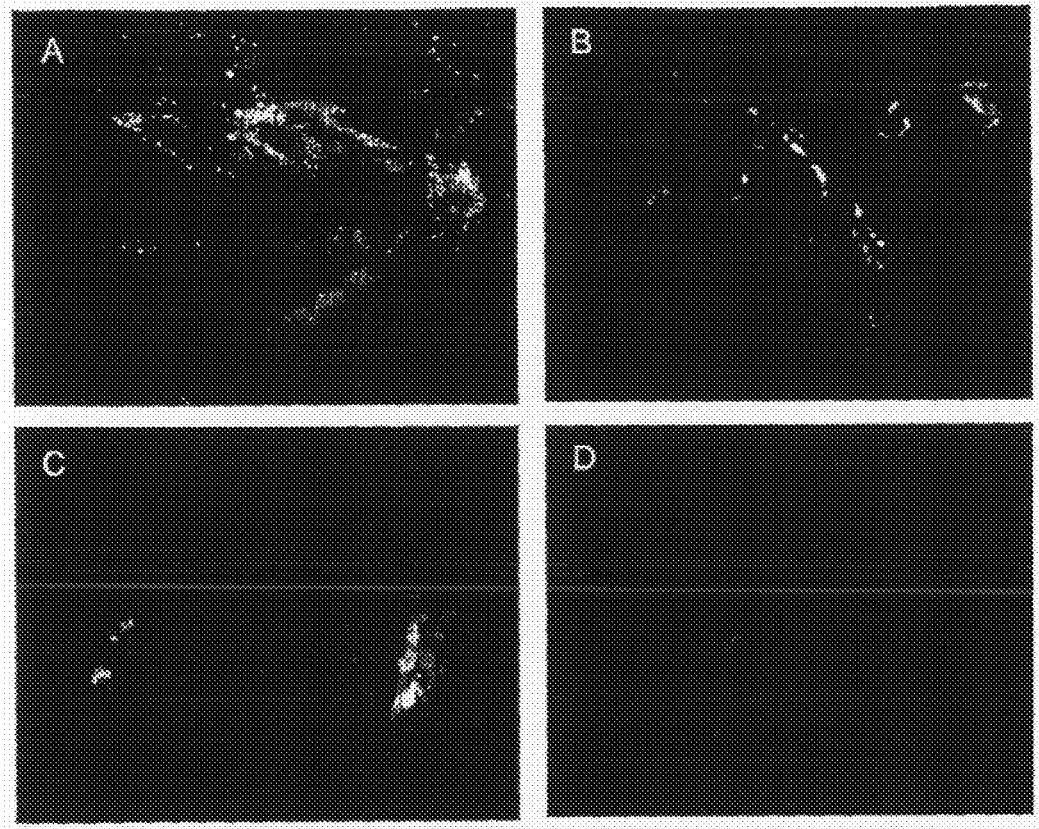
FIG. 12. Effect of culture with human serum on Neu5Gc expression in mesenchymal stem cells. A. Cells cultured in the presence of FBS. B. Number of Neu5Gc positive cells decreased when cells were cultured for one week in human serum. C. Individual Neu5Gc positive cells were still occasionally detected after two week cultivation in human serum. D. Negative control without the primary Neu5Gc specific antibody used to detect Neu5Gc expression. Magnification ×200.

In order to determine whether similar decontamination as observed in hESC also occurs in MSC, bone marrow derived MSC were induced to undergo osteogenic differentiation in the presence of FBS. It was found that the differentiated cells had on average approximately 50% lower Neu5Gc contents than the original MSC and in one out of four cell lines N-glycan structures containing Neu5Gc could not be detected after cell culture in differentiation medium (FIG. 12). The results suggested that also MSC progeny could be at least partially decontaminated with respect to Neu5Gc.

Disappearance of Neu5Gc from mesenchymal stem cells cultured in human serum. In order to investigate whether MSC lines contaminated with Neu5Gc can be decontaminated by culturing them without contact to animal materials, MSC previously cultured with FBS were moved to the same media supplemented with human serum instead of FBS. In immunohistochemistry the number of Neu5Gc positive cells significantly decreased but after two weeks of culture individual Neu5Gc positive cells were still occasionally detected (FIG. 12). This suggested that although most cells could be easily decontaminated with regard to Neu5Gc, absolute decontamination may be difficult to reach. Mass spectrometric analysis of the Neu5Gc content in MSC transferred from FBS to human serum containing cell culture medium indicated that Neu5Gc contamination was significantly decreased in MSC grown in human serum (FIG. 10G).

Discussion

It has previously been reported that hESC are capable of efficient Neu5Gc uptake from culture media components (6, 11). Significantly, the present data extended the concern of Neu5Gc contamination to human MSC. It seems likely that any human MSC line cultured in contact with animal-derived material will incorporate some immunogenic Neu5Gc on their surface. Since human serum contains high titers of antibodies against the Neu5Gc xenoantigen (6, 12), viability and therefore therapeutic efficacy of cellular products expressing Neu5Gc may be compromised. Importantly, this may be reflected in the published results of human clinical trials utilizing MSC exposed to FBS (1-5). Rat MSC grown with rat serum have yielded better engraftment results than those grown with FBS (13). Furthermore, in clinical trials with FBS-grown MSC, antibodies against FBS have been detected (5). The potential adverse effects should be taken into account when designing new preclinical and clinical trials (14-17).

In general, based on the current data it is clear that all stem cell culture conditions should be controlled with respect to Neu5Gc contamination. There are reliable biochemical and immunochemical methods for analyzing Neu5Gc content in biological materials (6, 11), and in the present study we further demonstrated novel mass spectrometric and monoclonal antibody-based methods for controlling Neu5Gc contamination in stem cells. Given that Neu5Gc content varies between different animal proteins, it seems theoretically possible to rationally design serum replacement supplements with low and controlled Neu5Gc content even using animal materials. Ideally, however, serum replacement protein supplements would be purified or recombinant human proteins produced in Neu5Gc-controlled conditions. Attempts to define such media have recently been published (11).

Importantly, the present data suggest that culturing both hESC and MSC in appropriate conditions results in removal of Neu5Gc from stem cells or the stem cell progeny. Accordingly, recent studies have demonstrated by direct chemical analyses that hESC lose the Neu5Gc contamination (11) and the susceptibility to Neu5Gc-specific immune response (18) during cell culture with human-derived supplements. This is in accordance of our finding that most MSC became decontaminated after prolonged culture in media in which FBS was replaced by human serum. However, our results suggested that complete decontamination may be difficult to achieve by changing culture conditions as individual cells may express Neu5Gc even after long periods. For the generation of pure Neu5Gc negative cell populations a negative selection, e.g. fluorescence assisted cell sorting (FACS), might prove feasible.

The molecular mechanism of Neu5Gc loss from stem cells remains to be clarified (19). It is known that cells are able to secrete sialic acid-containing glycoprotein materials into culture medium, suggesting that Neu5Gc-containing material can also be secreted. Another direct mechanism of Neu5Gc loss is dilution of the molecule in stem cell progeny during normal cell growth and division. Intriguingly, the present analyses showed significant reduction in Neu5Gc levels in both hESC and MSC during cell culture especially after stem cell differentiation in differentiation-inducing culture conditions.

Finally, with respect to the existing stem cells potentially contaminated with Neu5Gc, it should be noted that even normal human tissues may acquire minor amounts of Neu5Gc from dietary and other sources without being rejected by the immune system (19, 20). It is therefore unlikely that the vast majority of currently existing hESC and MSC lines that have been inadvertently exposed to Neu5Gc will be permanently contaminated and unfit for future applications if they are cultured in conditions avoiding renewed exposure to animal materials.

References for Example 9

1. Sotiropoulou, P. A., Perez, S. A., Salagianni, M., Baxevanis, C. N., and Papamichail, M. 2006. Characterization of the optimal culture conditions for clinical scale production of human mesenchymal stem cells. *Stem Cells.* 24:462-471.
2. Mazzini, L., Fagioli, F., Boccaletti, R., Mareschi, K., Oliveri, G., Olivieri, C., Pastore, I., Marasso, R., and Madon, E. 2003. Stem cell therapy in amyotrophic lateral sclerosis: a methodological approach in humans. *Amyotroph. Lateral Scler. Other Motor Neuron Disord.* 4:158-161.
3. Bang, O. Y., Lee, J. S., Lee, P. H., and Lee, G. 2005. Autologous mesenchymal stem cell transplantation in stroke patients. *Ann. Neurol.* 57:874-882.
4. Chen, S. L., Fang, W. W., Ye, F., Liu, Y. H., Qian, J., Shan, S. J., Zhang, J. J., Chunhua, R. Z., Liao, L. M., Lin, S., and Sun, J. P. 2004. Effect on left ventricular function of intracoronary transplantation of autologous bone marrow mesenchymal stem cell in patients with acute myocardial infarction. *Am. J. Cardiol.* 94:92-95.
5. Horwitz, E. M., Gordon, P. L., Koo, W. K., Marx, J. C., Neel, M. D., McNall, R. Y., Muul, L., and Hofmann, T. 2002. Isolated allogeneic bone marrow-derived mesenchymal cells engraft and stimulate growth in children with osteogenesis imperfecta: Implications for cell therapy of bone. *Proc. Natl. Acad. Sci.* 99:8932-8937.
6. Martin, M. J., Muotri, A., Gage, F., and Varki, A. 2005. Human embryonic stem cells express an immunogenic nonhuman sialic acid. *Nat. Med.* 11:228-232.
7. Moreno, E., Lanne, B., Vázquez, A. M., Kawashima, I., Tai, T., Fernandez, L. E., Karlsson, K. A., Ångström, J., and Perez, R. 1998. Delineation of the epitope recognized by an antibody specific for N-glycolylneuraminic acid-containing gangliosides. *Glycobiology.* 8:695-705.
8. Vázquez, A. M., Alfonso, M., Lanne, B., Karlsson, K. A., Carr, A., Barroso, O., Fernandez, L. E., Rengifo, E., Lanio, M. E., Alvarez, C. et al. 1995. Generation of a murine monoclonal antibody specific for N-glycolylneuraminic acid-containing gangliosides that also recognizes sulfated glycolipids. *Hybridoma.* 14:551-556.
9. Skottman, H., Mikkola, M., Lundin, K., Olsson, C., Strömberg, A. M., Tuuri, T., Otonkoski, T., Hovatta, O., and Lahesmaa, R. 2005. Gene expression signatures of seven individual human embryonic stem cell lines. *Stem cells.* 23:1343-1356.

10. Leskelä, H. V., Risteli, J., Niskanen, S., Koivunen, J., Ivaska, K. K., and Lehenkari, P. 2003. Osteoblast recruitment from stem cells does not decrease by age at late adulthood. *Biochem. Biophys. Res. Commun.* 311:1008-1013.
11. Ludwig, T. E., Levenstein, M. E., Jones, J. M., Berggren, W. T., Mitchen, E. R., Frane, J. L., Crandall, L. J., Daigh, C. A., Conard, K. R., Piekarczyk, M. S., Llanas, R. A., and Thomson, J. A. 2006. Derivation of human embryonic stem cells in defined conditions. *Nat. Biotechnol.* 24:185-187.
12. Nguyen, D. H., Tangvoranuntakul, P., and Varki, A. 2005. Effects of natural human antibodies against a nonhuman sialic acid that metabolically incorporates into activated and malignant immune cells. *J. Immunol.* 175:228-236.
13. Gregory, C. A., Reyes, E., Whitney, M. J., and Spees, J. L. 2006. Enhanced engraftment of mesenchymal stem cells in a cutaneous wound model by culture in allogenic species-specific serum and administration in fibrin constructs. *Stem cells.* In press.
14. Mackensen, A., Dräger, Schlesier, M., Mertelsmann, R., and Lindemann, A. 2000. Presence of IgE antibodies to bovine serum albumin in a patient developing anaphylaxis after vaccination with human peptide pulsed dendritic cells. *Cancer Immunol. Immunother.* 49:152-156.
15. Selvaggi, T. A., Walker, R. E. and Fleisher, T. A. 1997. Development of antibodies to fetal calf serum with arthus-like reactions in human immunodeficiency virus-infected patients given syngeneic lymphocyte infusions. *Blood.* 89:776-779.
16. Tuschong, L., Soenen, S. L., Blaese, R. M., Candotti, F., and Muul, L. M. 2002. Immune response to fetal calf serum by two adenosine deaminase-deficient patients after T cell gene therapy. *Hum. Gene Ther.* 13:1605-1610.
17. Merrick, J. M., Zadarlik, K., and Milgrom, F. 1978. Characterization of the Hanganutziu-Deicher (serum-sickness) antigen as gangliosides containing N-glycolylneuraminic acid. *Int. Arch. Allergy Appl. Immunol.* 57:477-480.
18. Martin, M. J., Muotri, A., Gage, F., and Varki, A. 2004. *Blood* (ASH Annual Meeting Abstracts). 104: Abstract 4182.
19. Bardor, M., Nguyen, D. H., Diaz, S., and Varki, A. 2005. Mechanism of uptake and incorporation of the non-human sialic acid N-glycolylneuraminic acid into human cells. *J. Biol. Chem.* 280:4228-4237.
20. Tangvoranuntakul, P., Gagneux, P., Diaz, S., Bardor, M., Varki, N., Varki, A., and Muchmore, E. 2003. Human uptake and incorporation of an immunogenic nonhuman dietary sialic acid. *Proc. Natl. Acad. Sci. U.S.A.* 100: 12045-12050.
21. Nyman, T. A., Kalkkinen, N., T616, H., and Helin, J. 1998. Structural characterisation of N-linked and O-linked oligosaccharides derived from interferon-α2b and interferon-α14c produced by Sendai-virus-induced human peripheral blood leukocytes. *Eur. J. Biochem.* 253:485-493.
22. Saarinen, J., Welgus, H. G., Flizar, C. A., Kalkkinen, N., and Helin, J. 1999. N-glycan structures of matrix metalloproteinase-1 derived from human fibroblasts and from HT-1080 fibrosarcoma cells. *Eur. J. Biochem.* 259:829-840.
23. Papac, D. I., Wong, A., and Jones, A. J. 1996. Analysis of acidic oligosaccharides and glycopeptides by matrix-assisted laser desorption/ionization time-of-flight mass spectrometry. *Anal. Chem.* 68:3215-3223.
24. Miller-Podraza, H., Johansson, L., Johansson, P., Larsson, T., Matrosovich, M., and Karlsson, K.-A. 2000. A strain of human influenza A virus binds to extended but not short gangliosides as assayed by thin-layer chromatography overlay. *Glycobiology.* 10:975-982.

Example 10

Removal of NeuGc from Bovine Serum Proteins

Acid Hydrolysis for Desialylation of Glycoprotein

Example 10a

Preparation of Desialylated Bovine Serum Protein(s)

Experimental Procedures

To desialylate glycoprotein such as bovine serum protein efficiently without severe protein degradation, it is dissolved in aqueous acid and incubated for an optimal time as described below. The optimal incubation temperature is under +80° C. as described below.

To determine sialylation level of N-glycans, they are enzymatically released from glycoprotein, purified, and analyzed by MALDI-TOF mass spectrometry as described in the preceding Examples.

Results

Bovine serum protein was determined to contain 18% monosialylated and 82% disialylated N-glycan chains by MALDI-TOF mass spectrometry.

In order to specifically desialylate serum protein without affecting its functional properties by degradation of its protein or carbohydrate parts, several aqueous acid hydrolysis procedures were tested (Table 10) and desialylation levels determinated by analysing isolated As indicated in Table 10, >90% desialylation by the method of Spiro (1960) leads to heavy degradation of the serum protein backbone. This was exemplified also in gel filtration chromatography of the products by the method of Spiro (1960) and by the HCl acid hydrolysis method (Table 10), showing that the milder HCl method in lower than +80° C. temperatures (FIG. 13a) results in significantly less protein degradation than the method of Spiro (1960; FIG. 13b).

When commercial desialylated fetuin (asialofetuin, Sigma) prepared by a modification of the procedure of Spiro (1960) was analyzed by gel electrophoresis (SDS-PAGE), its protein part was shown to be heavily degraded into over 15 molecular fragments of different sizes. The manufacturer's specifications for the commercial asialofetuin indicate sialic acid concentration below 5 mg/g, which is equivalent to loss of approximately over 94% of sialic acid residues (sialic acid content of the original fetuin glycoprotein is 8.7%; Spiro, 1960).

When HCl acid hydrolyzed samples were neutralized by sodium carbonate or sodium hydroxide, the resulting salt in the neutral end product was sodium chloride.

When serum protein N-glycans were enzymatically desialylated with sialidase enzymes including *A. ureafaciens* sialidase (recombinant in *E. coli*; Calbiochem), no protein degradation was observed, and the desialylation level was nearly 100% leading to no detectable traces of sialylated serum protein N-glycans.

Figure 14:
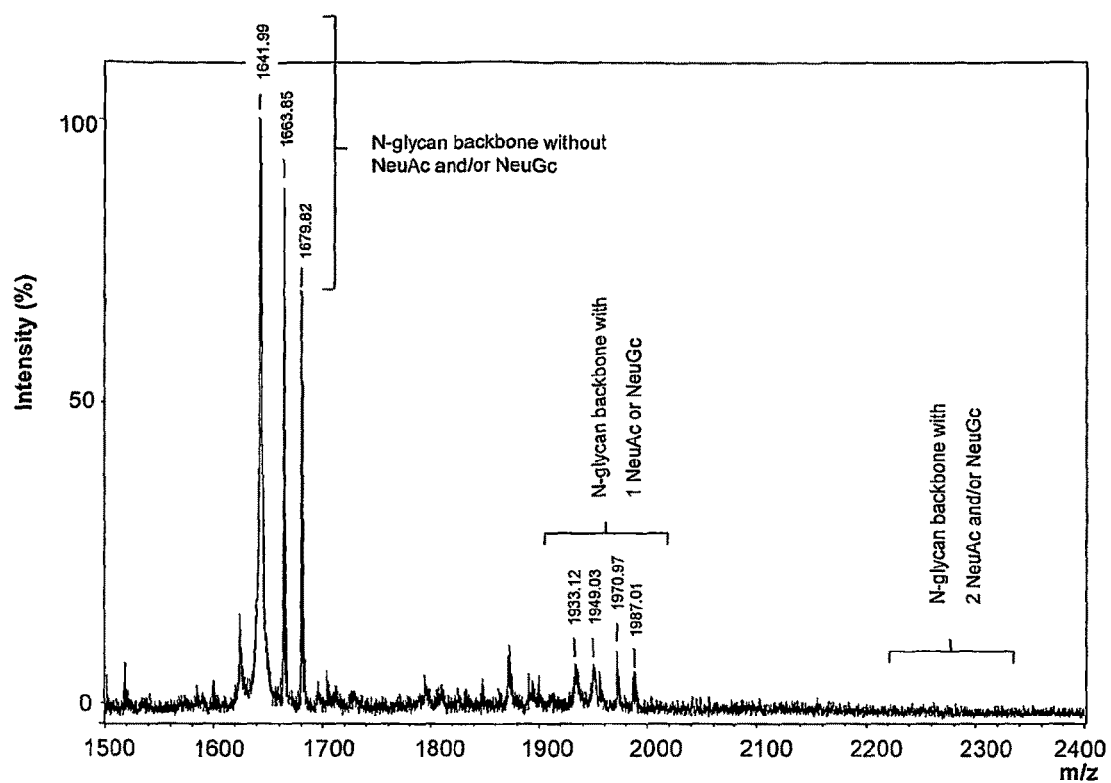
FIG. 14. The disialylated N-glycan form could not be observed after successful desialylation by HCl acid hydrolysis, but some monosialylated N-glycan chains persisted.

In all HCl acid hydrolysis methods (Table 10) no evidence of degradation of the neutral N-glycan backbone ($Hex_5HexNAc_4$) was observed. The disialylated N-glycan form could not be observed after successful desialylation by HCl acid hydrolysis, but some monosialylated N-glycan chains persisted (FIG. 14). However, acid hydrolysis at +80°

C. resulted in degradation of the neutral N-glycan backbone as well, as indicated by MALDI-TOF mass spectrometric analysis.

Example 10b

Preparation of Serum Proteins with Defined Sialic Acid Composition

Experimental Procedures

500 µg of desialylated (by HCl acid hydrolysis, see above) bovine serum protein was incubated with 1 µmol of CMP-NeuAc and 20 mU of α2,3-sialyltransferase (Calbiochem, 566218) for 67 hours at +37° C. Another set (500 µg) of acid hydrolyzed bovine serum protein was incubated with 1.0 µmol of CMP-NeuGc as described above. The reaction mixtures were run in Superdex 200 10/300 GL column (Amersham Biosciences) in 200 mM $(NH_4)HCO_3$. The elution peaks emerging at 13.81 ml were collected (the elution time for intact bovine serum protein is 13.8 ml). About 200 pmol of re-sialylated serum protein (either with NeuAc or NeuGc) was treated with N-glycosidase F (NGF) as described in the preceding Examples to release the N-glycans for mass spectrometric characterization.

Results

The MALDI-TOF MS spectra of both resialylation reactions showed the following product distribution: unsialylated ~30%, monosialylated ~60% and disialylated ~10%.

After the desialylation and resialylation procedure, the N-glycan structure was homogeneous with respect to the N-glycan backbone integrity, as indicated by the MALDI-TOF mass spectrometric analyses. N-glycan backbone cleavages in e.g. the α2,3-Neu5Ac sialylated serum protein were not observed in the obtained mass spectrum of the isolated N-glycans.

The N-glycan oligosaccharide chains thereafter included the structures indicated below (1-2):

(1)
(Neu5Acα2-3)$_{0-1}$Galβ1-4GlcNAcβ1-2Manα1-6
    Manβ1-4GlcNAcβ1-4GlcNAcβ-N-transferrin
(Neu5Acα2-3)$_{0-1}$Galβ1-4GlcNAcβ1-2Manα1-3

(2)
(Neu5Gcα2-3)$_{0-1}$Galβ1-4GlcNAcβ1-2Manα1-6
    Manβ1-4GlcNAcβ1-4GlcNAcβ-N-transferrin
(Neu5Gcα2-3)$_{0-1}$Galβ1-4GlcNAcβ1-2Manα1-3

Example 10c

Spectrophotometric Analysis of Serum Protein with Defined Sialic Acid Composition The serum protein (Sigma) and acid hydrolyzed (either with HCl or $H_2SO_4$) protein were run in Superdex 200 column in 10 mM Tris-HCl-1 mM $NaHCO_3$, pH 7.4. Elution peaks were collected and concentrated into the final volume (⅕ of the elution volume). Protein concentration in the concentrated samples was about 50 µM in 50 mM Tris-HCl-5 mM $NaHCO_3$, pH 7.4. Visible absorption spectra (280 nm-600 nm) were measured in the absence and in the presence of a ligand reagent for the serum protein. The HCl-hydrolyzed and $H_2SO_4$-hydrolyzed proteins gave their absorption maximum near the specific absorption wavelength of protein-ligand complex, indicating that they both bound the ligand. However, the results indicated that the $H_2SO_4$ acid hydrolysis procedure yielded a protein product with an absorption maximum farther away from the maximum of the native protein in comparison to the HCl acid hydrolysis protein product. This indicated that HCl procedure yielded a product more like the native protein.

Example 10d

Recognition of Neu5Gc Expressing Human Cells by Monoclonal Antibodies

Experimental Procedures

Human bone marrow derived mesenchymal stem cells (BM MSC) were generated as described (Leskelä et al., 2003). Briefly, bone marrow obtained during orthopedic surgery was cultured in Minimum Essential Alpha-Medium (α-MEM), supplemented with 20 mM HEPES, 10% FBS, 1× penicillin-streptomycin and 2 mM L-glutamine (all from Gibco). After a cell attachment period of 2 days the cells were washed with $Ca^{2+}$ and $Mg^{2+}$ free PBS (Gibco), and subcultured at a density of 2000-3000 cells/cm$^2$ in the same media. MSC layers on passages 9-14 were used to the experiments.

Cells were metabolically labelled with either Neu5Gc or Neu5Ac by adding 3 mM monosaccharide to the cell culture medium and incubating under standard culture conditions as described above.

A Neu5Gc-specific P3 monoclonal antibody against the glycolipid antigen GM3(Gc) was used to detect Neu5Gc glycoconjugates on cell surface as described in the preceding Examples.

Results

BM MSC metabolically labelled with Neu5Gc showed increased binding of the Neu5Gc-specific monoclonal antibody compared with either nonlabelled or Neu5Gc-labelled cells. This indicated that the cells metabolically labelled with Neu5Gc incorporated Neu5Gc-containing glycoconjugates on their surface and that the antibody staining intensity was a good measure of the incorporated Neu5Gc content of the cells.

Example 11

Materials and Methods

Human bone marrow-derived mesenchymal stem cells (MSC) were generated as described by Leskelä et al. (2003). Briefly, bone marrow obtained during orthopedic surgery was cultured in Minimum Essential Alpha-Medium (α-MEM), supplemented with 20 mM HEPES, 10% FCS, 1× penicillin-streptomycin and 2 mM L-glutamine (Gibco). After a cell attachment period of 2 days, the cells were washed with Ca2+ and Mg2+ free PBS, and subcultured at a density of 2000-3000 cells/cm2 in the proliferating media. Cells were grown at 37° C. with 5% $CO_2$. MSC layers on passages 9-14 were used to the experiments.

Monoclonal antibody against Neu5Gc. The antibody (Moreno et al., 1998; Vázquez et al., 1995) was characterized to have binding specificity against glycolipid antigens GM3 (Neu5Gc) as well as Neu5Gcα2,3-lacto-N-neotetraosyl ceramide by binding to previously characterized glycolipid standard molecules on thin-layer chromatography plates. Secondary detection of the mAb was performed with FITC labeled goat-anti-mouse antibody in dilution of 1:300 (Sigma).

Immunostaining. MSCs were grown on coated glass 8-chamber slides (Lab-TekII, Nalge Nunc) at 37° C. with 5% $CO_2$ for 2-4 days. After culture, cells were rinsed 5 times with PBS (10 mM sodium phosphate, pH 7.2, 140 mM NaCl) and fixed with 4% PBS-buffered paraformaldehyde pH 7.2 at RT for 15 minutes, followed by 3 rounds of washing with PBS.

Specificity of the Neu5Gc-specific staining was confirmed by sialidase treatment using 10 mU of sialidase (*Arthrobacter ureafaciens*, Glyko) in 50 mM sodium acetate buffer pH 5.5 over night at 37° C. After the sialidase treatment, cells were washed 3 times with PBS. Desialylation diminished the mAb binding to the cells.

After fixation and different treatments, non-specific binding was blocked with 3% HSA-PBS for 30 minutes at RT. Primary antibodies were diluted in 1% HSA-PBS and incubated for 60 minutes at RT, followed by 3 rounds of washing with PBS. Secondary antibodies were incubated for 60 minutes at RT, washed 3 times with PBS and mounted in Vectashield mounting medium containing DAPI-stain (Vector Laboratories).

Immunostaining was observed with Zeiss Axioskop 2 plus fluorescence microscope (Carl Zeiss Vision GmbH) with FITC and DAPI filters. Images were taken with Zeiss Axio-Cam MRc camera and with AxioVision Software 3.1/4.0 (Carl Zeiss) with 400× magnification.

Incubation of MSC with polyvalent Neu5Gc conjugate. Polyvalent α-Neu5Gc (α-Neu5Gc-PAA-biotin), conjugated via O-glycosidically linked spacer to polyacrylamide (20 mol-%) modified with biotin (5 mol-%) was from Lectinity, Inc. (Moscow, Russia). It was added to the cell culture medium.

Results

Human bone marrow derived mesenchymal stem cells (MSC) were first cultured in fetal bovine serum (FBS) containing grown cell culture medium. When they were transferred into human serum, their Neu5Gc content detected by anti-Neu5Gc monoclonal antibody (Neu5Gc mAb) was significantly decreased. This result further indicated that Neu5Gc mAb specifically recognized Neu5Gc epitopes in the cells.

When polyvalent Neu5Gc conjugate was added to the culture medium, human bone marrow derived MSC took it inside the cells, specifically increasing the staining of the cells by Neu5Gc mAb (FIG. 15A). The staining pattern with Neu5Gc mAb was particulate in appearance, as shown in FIG. 15B, indicating that the Neu5Gc conjugate was localized in specific compartments of the cells.

REFERENCES

Altmann, F., et al. (1999) *Glycoconj. J.* 16:109-23
Chou, H.-H., et al. (1998) *Proc. Natl. Acad. Sci. USA* 95:11751-6
Harvey, D. J., et al. (1993) *Rapid Commun. Mass Spectrom.* 7(7):614-9
Irie, A., et al. (1998) *J. Biol. Chem.* 273(25):15866-71
Kretzchmar, E., et al. (1994) *Biol. Chem. Hoppe Seyler* 375 (5):23-7
Kubelka, V., et al. (1994) *Arch. Biochem. Biophys.* 308(1):148-57
Moreno, E. et al. (1998). *Glycobiology.* 8:695-705.
Leskelä, H., et al. (2003) *Biochem. Biophys. Res. Commun.* 311:1008-13
Naven, T. J. & Harvey, D. J. (1996) *Rapid Commun. Mass Spectrom.* 10(11):1361-6
Nyman, T. A., et al. (1998) *Eur. J. Biochem.* 253(2):485-93
Papac, D., et al. (1996) *Anal. Chem.* 68(18):3215-23
Rohrer, J. S., et al. (1998) *Glycobiology* 8(1):35-43
Saarinen, J., et al. (1999) *Eur. J. Biochem.* 259(3):829-40
Spiro, R. G. *J. Biol. Chem.* 235, 2860-2869 (1960).
Staudacher, E., et al. (1992) *Eur. J. Biochem.* 207(3):987-93
Thomson, J. A., et al. (1998) *Science* 282:1145-7
Vázquez, A. M. et al. (1995). *Hybridoma.* 14:551-556.
Ylönen, A., et al. (2001) *Glycobiology* 11(7):523-31

TABLE 1

Detection of N-glycolylneuraminic acid (Neu5Gc) containing sialylated N-glycans in stem cells and cells differentiated therefrom.

| Proposed monosaccharide composition | m/z (calculated) | m/z (experimental) |
|---|---|---|
| Human embryonal stem cell line: | | |
| NeuGcHex3HexNAc3dHex2/NeuAcHex4HexNAc3dHex | 1711.61 | 1711.74 |
| NeuGcHex4HexNAc3dHex/NeuAcHex5HexNAc3 | 1727.60 | 1727.68 |
| NeuGcHex5HexNAc4 | 1946.67 | 1946.7 |
| NeuGcHex5HexNAc4dHex/NeuAcHex6HexNAc4 | 2092.73 | 2092.73 |
| NeuGcNeuAcHex5HexNAc4 | 2237.77 | 2237.7 |
| NeuGc2Hex5HexNAc4 | 2253.76 | 2253.73 |
| NeuGcHex6HexNAc4dHex/NeuAcHex7HexNAc4 | 2254.79 | 2254.73 |
| NeuAc2Hex6HexNAc4/NeuGcNeuAcHex5HexNAc4dHex | 2383.83 | 2383.72 |
| NeuGc5HexNAc4dHex3/NeuAcHex6HexNAc4dHex2 | 2384.85 | 2384.72 |
| NeuGcNeuAc2Hex5HexNAc4 | 2528.87 | 2528.77 |
| NeuGc2NeuAcHex5HexNAc4 | 2544.86 | 2544.89 |
| NeuGc2Hex5HexNAc4dHex2/NeuGcNeuAcHex6HexNAc4dHex | 2545.88 | 2545.97 |
| Human bone marrow mesenchymal stem cell line: | | |
| NeuGcHex3HexNAc3dHex2/NeuAcHex4HexNAc3dHex | 1711.61 | 1711.87 |
| NeuGcHex4HexNAc3dHex/NeuAcHex5HexNAc3 | 1727.60 | 1727.87 |
| NeuGcHex5HexNAc3 | 1743.60 | 1743.7 |
| NeuGcHex3HexNAc5 | 1825.65 | 1825.91 |
| NeuGcHex5HexNAc4 | 1946.67 | 1946.92 |
| NeuGcNeuAcHex4HexNAc3dHex/NeuAc2Hex5HexNAc3 | 2018.70 | 2018.88 |
| NeuGcHex5HexNAc4dHex/NeuAcHex6HexNAc4 | 2092.73 | 2093 |
| NeuAcHex7HexNAc4/NeuGcHex6HexNAc4dHex | 2254.79 | 2255.03 |
| NeuAcHex7HexNAc5dHex/NeuGcHex6HexNAc5dHex2 | 2603.92 | 2604.13 |
| Cord blood CD 133+ cells, sialylated N-glycans: | | |
| NeuGcHex3HexNAc3 | 1419.49 | 1419.68 |
| NeuGcHex4HexNAc3 | 1581.54 | 1581.74 |
| NeuGcHex3HexNAc3dHex2/NeuAcHex4HexNAc3dHex | 1711.61 | 1711.82 |
| NeuGcHex4HexNAc3dHex/NeuAcHex5HexNAc3 | 1727.60 | 1727.83 |
| NeuGcHex4HexNAc4 | 1784.62 | 1784.85 |

TABLE 1-continued

Detection of N-glycolylneuraminic acid (Neu5Gc) containing sialylated N-glycans in stem cells and cells differentiated therefrom.

| Proposed monosaccharide composition | m/z (calculated) | m/z (experimental) |
|---|---|---|
| NeuGcHex4HexNAc3dHex2/NeuAcHex5HexNAc3dHex | 1873.66 | 1873.89 |
| NeuGcHex5HexNAc4 | 1946.67 | 1946.9 |
| NeuGcNeuAcHex4HexNAc3dHex/NeuAc2Hex5HexNAc3 | 2018.70 | 2018.91 |
| NeuGcHex5HexNAc4SO3 | 2026.63 | 2026.82 |
| NeuGcHex5HexNAc4dHex/NeuAcHex6HexNAc4 | 2092.73 | 2092.95 |
| NeuGcNeuAcHex5HexNAc4 | 2237.77 | 2237.97 |
| NeuGcHex5HexNAc4dHex2/NeuAcHex6HexNAc4dHex | 2238.79 | 2238.97 |
| NeuGc2Hex5HexNAc4 | 2253.76 | 2253.97 |
| NeuGcHex6HexNAc4dHex/NeuAcHex7HexNAc4 | 2254.79 | 2254.97 |
| NeuAc2Hex6HexNAc4/NeuGcNeuAcHex5HexNAc4dHex | 2383.83 | 2384.03 |
| NeuGcHex5HexNAc4dHex3/NeuAcHex6HexNAc4dHex2 | 2384.85 | 2385.04 |
| NeuGc2Hex5HexNAc4dHex/NeuGcNeuAcHex6HexNAc4 | 2399.82 | 2400.02 |
| NeuGcNeuAc2Hex5HexNAc4 | 2528.87 | 2529.05 |
| NeuGc2NeuAcHex5HexNAc4 | 2544.86 | 2545.06 |
| NeuGc2Hex5HexNAc4dHex2/NeuGcNeuAcHex6HexNAc4dHex | 2545.88 | 2546.06 |
| NeuGcNeuAcHex6HexNAc5 | 2602.90 | 2603.08 |
| NeuGcHex6HexNAc5dHex2/NeuAcHex7HexNAc5dHex | 2603.92 | 2604.09 |
| NeuGcHex8HexNAc5dHex/NeuAcHex9HexNAc5 | 2781.97 | 2782.18 |
| NeugcNeuAc2Hex6HexNAc5 | 2894.00 | 2894.2 |
| NeuGcNeuAcHex6HexNAc5dHex2/NeuAc2Hex7HexNAc5dHex | 2895.00 | 2895.15 |

TABLE 2

Differential effect of α2,3-sialidase treatment on isolated sialylated N-glycans from cord blood CD133+ and CD133− cells.

| m/z | Proposed monosaccharide composition | Sialylated N-glycan CD133+ | Sialylated N-glycan CD133− | Neutral N-glycan CD133+ | Neutral N-glycan CD133− |
|---|---|---|---|---|---|
| 1768 | (NeuAc$_1$)Hex$_4$HexNAc$_4$ | + | + | + | − |
| 2156 | (NeuAc$_1$)Hex$_8$HexNAc$_2$dHex$_1$/ (NeuAc$_1$Hex$_5$HexNAc$_4$dHex$_1$SO$_3$) | + | + | + | − |
| 2222 | (NeuAc$_1$)Hex$_5$HexNAc$_4$dHex$_2$ | + | + | + | − |
| 2238 | (NeuAc$_1$)Hex$_6$HexNAc$_4$dHex$_1$/ (NeuGc$_1$)Hex$_5$HexNAc$_4$dHex$_2$ | + | + | + | − |
| 2254 | (NeuAc$_1$)Hex$_7$HexNAc$_4$/ (NeuGc$_1$)Hex$_6$HexNAc$_4$dHex$_1$ | + | + | + | − |
| 2368 | (NeuAc$_1$)Hex$_5$HexNAc$_4$dHex$_3$ | + | + | + | − |
| 2447 | (NeuAc$_2$)Hex$_8$HexNAc$_2$dHex$_1$/ (NeuAc$_2$Hex$_5$HexNAc$_4$dHex$_1$SO$_3$) | + | + | + | − |
| 2448 | (NeuAc$_1$)Hex$_8$HexNAc$_2$dHex$_3$/ (NeuAc$_1$Hex$_5$HexNAc$_4$dHex$_3$SO$_3$) | + | + | + | − |
| 2513 | (NeuAc$_2$)Hex$_5$HexNAc$_4$dHex$_2$ | + | + | + | − |
| 2733 | (NeuAc$_1$)Hex$_6$HexNAc$_5$dHex$_3$ | + | + | + | − |
| 2953 | (NeuAc$_1$)Hex$_7$HexNAc$_6$dHex$_2$ | + | + | + | − |

The neutral N-glycan columns show that neutral N-glycans corresponding to the listed sialylated N-glycans appear in analysis of CD133+ cell N-glycans but not CD133− cell N-glycans.
Proposed glycan compositions outside parenthesis are visible in the neutral N-glycan fraction after α2,3-sialidase digestion of CD133+ cell sialylated N-glycans.

TABLE 3

Cord blood mononuclear cell sialylated N-glycan signals. The m/z values refer to monoisotopic masses of [M − H]− ions.

| Proposed monosaccharide composition | m/z (calculated) | |
|---|---|---|
| NeuAcHex3HexNAc3dHex | 1549.55 | 1549 |
| NeuAcHex4HexNAc3 | 1565.55 | 1565 |
| NeuAc2Hex3HexNAc2dHex | 1637.57 | 1637 |
| NeuAc2Hex2HexNAc3dHex | 1678.60 | 1678 |
| NeuAcHex4HexNAc3dHex | 1711.61 | 1711 |
| NeuAcHex5HexNAc3 | 1727.60 | 1727 |
| NeuAcHex3HexNAc4dHex | 1752.63 | 1752 |
| NeuAcHex4HexNAc4 | 1768.57 | 1768 |
| NeuAcHex4HexNAc3dHexSO3 | 1791.56 | 1791 |
| NeuAc2Hex3HexNAc3dHex | 1840.65 | 1840 |
| NeuAcHex4HexNAc3dHex2 | 1857.66 | 1857 |
| Hex5HexNAc4dHexSO3 | 1865.60 | 1865 |
| NeuAcHex5HexNAc3dHex | 1873.66 | 1873 |
| NeuAcHex6HexNAc3 | 1889.65 | 1889 |
| NeuAcHex3HexNAc4dHex2 | 1898.69 | 1898 |
| NeuAcHex4HexNAc4dHex | 1914.68 | 1914 |
| NeuAcHex5HexNAc4 | 1930.68 | 1930 |
| NeuAc2Hex4HexNAc3dHex/ | 2002.70 | 2002 |

TABLE 3-continued

Cord blood mononuclear cell sialylated N-glycan signals. The m/z values refer to monoisotopic masses of [M − H]⁻ ions.

| Proposed monosaccharide composition | m/z (calculated) | |
|---|---|---|
| Hex8HexNAc3SO3 | | |
| NeuAc2Hex5HexNAc3 | 2018.70 | 2018 |
| NeuAcHex6HexNAc3dHex | 2035.71 | 2035 |
| NeuAcHex7HexNAc3 | 2051.71 | 2051 |
| Hex4HexNAc5dHex2SO3 | 2052.68 | 2052 |
| NeuAc2Hex4HexNAc4 | 2059.72 | 2059 |
| NeuAcHex4HexNAc4dHex2 | 2060.74 | 2060 |
| NeuAcHex5HexNAc4dHex | 2076.74 | 2076 |
| NeuAcHex6HexNAc4 | 2092.73 | 2092 |
| NeuAcHex4HexNAc5dHex | 2117.76 | 2117 |
| NeuAcHex5HexNAc5 | 2133.76 | 2133 |
| NeuAcHex8HexNAc2dHex/ NeuAcHex5HexNAc4dHexSO3 | 2156.74/2156.69 | 2156 |
| NeuAc2Hex5HexNAc4 | 2221.78 | 2221 |
| NeuAcHex5HexNAc4dHex2 | 2222.80 | 2222 |
| Hex6HexNAc5dHexSO3 | 2230.73 | 2230 |
| NeuAcHex6HexNAc4dHex/ NeuGcHex5HexNAc4dHex2 | 2238.79 | 2238 |
| NeuAcHex7HexNAc4/ NeuGcHex6HexNAc4dHex | 2254.79 | 2254 |
| NeuAcHex5HexNAc5dHex | 2279.82 | 2279 |
| NeuAc2Hex4HexNAc3dHex3 | 2294.82 | 2294 |
| NeuAcHex6HexNAc5 | 2295.81 | 2295 |
| NeuAc2Hex5HexNAc4dHex | 2367.83 | 2367 |
| NeuAcHex5HexNAc4dHex3 | 2368.85 | 2368 |
| NeuAc2Hex6HexNAc4 | 2383.83 | 2383 |
| NeuAcHex6HexNAc4dHex2 | 2384.85 | 2384 |
| NeuAc2Hex5HexNAc3dHexSO3 | 2390.77 | 2390 |
| NeuAc2Hex3HexNAc5dHex2 | 2392.86 | 2392 |
| NeuAcHex5HexNAc5dHex2 | 2425.87 | 2425 |
| NeuAcHex6HexNAc5dHex | 2441.87 | 2441 |
| NeuAc2Hex8HexNAc2dHex/ NeuAc2Hex5HexNAc4dHexSO3 | 2447.83/2447.79 | 2447 |
| NeuAcHex7HexNAc5 | 2457.86 | 2457 |
| NeuAc2Hex5HexNAc4dHex2 | 2513.89 | 2513 |
| NeuAcHex6HexNAc5dHexSO3 | 2521.83 | 2521 |
| NeuAcHex6HexNAc4dHex3 | 2530.91 | 2530 |
| NeuAc3Hex4HexNAc5 | 2553.90 | 2553 |
| NeuAc2Hex5HexNAc5dHex | 2570.91 | 2570 |
| NeuAcHex5HexNAc5dHex3 | 2571.93 | 2571 |
| NeuAc2Hex6HexNAc5 | 2586.91 | 2586 |
| NeuAcHex6HexNAc5dHex2 | 2587.93 | 2587 |
| Hex7HexNAc6dHexSO3 | 2595.86 | 2595 |
| NeuAcHex7HexNAc5dHex | 2603.92 | 2603 |
| NeuAcHex6HexNAc6dHex | 2644.95 | 2644 |
| NeuAcHex7HexNAc6 | 2660.94 | 2660 |
| NeuAc2Hex4HexNAc5dHex2(SO3)2 | 2714.83 | 2714 |
| NeuAc2Hex6HexNAc5dHex | 2732.97 | 2732 |
| NeuAcHex6HexNAc5dHex3 | 2733.99 | 2733 |
| NeuAcHex7HexNAc6dHex | 2807.00 | 2807 |
| NeuAcHex6HexNAc5dHex3SO3 | 2813.94 | 2813 |
| NeuAc3Hex6HexNAc5 | 2878.00 | 2878 |
| NeuAc2Hex6HexNAc5dHex2 | 2879.02 | 2879 |
| NeuAcHex6HexNAc5dHex4 | 2880.04 | 2880 |
| NeuAc2Hex5HexNAc6dHex2 | 2920.05 | 2920 |
| NeuAc2Hex7HexNAc6 | 2952.04 | 2952 |
| NeuAcHex7HexNAc6dHex2 | 2953.06 | 2953 |
| NeuAcHex7HexNac7dHex | 3010.08 | 3010 |
| NeuAc3Hex6HexNAc5dHex | 3024.06 | 3024 |
| NeuAc2Hex6HexNAc5dHex3 | 3025.09 | 3025 |
| NeuAcHex8HexNAc7 | 3026.08 | 3026 |
| NeuAc2Hex7HexNAc6dHex | 3098.10 | 3098 |
| NeuAcHex7HexNAc6dHex3 | 3099.12 | 3099 |
| NeuAc2Hex6HexNAc5dHex4 | 3171.14 | 3171 |
| NeuAcHex8HexNAc7dHex | 3172.13 | 3172 |

TABLE 4

Mass spectrometric analysis results of sialylated N-glycans with monosaccharide compositions NeuAc$_{1-2}$Hex$_5$HexNAc$_4$dHex$_{0-3}$ in sequential enzymatic modification steps of human cord blood mononuclear cells.

| Proposed monosaccharide composition | calc m/z [M − H]⁻ | MNC | α2,3SAT | α2,3SAT + α1,3FucT |
|---|---|---|---|---|
| NeuAcHex5HexNAc4 | 1930.68 | 24.64 | 12.80 | 13.04 |
| NeuAcHex5HexNAc4dHex | 2076.74 | 39.37 | 30.11 | 29.40 |
| NeuAcHex5HexNAc4dHex2 | 2222.8 | 4.51 | 8.60 | 6.83 |
| NeuAcHex5HexNAc4dHex3 | 2368.85 | 3.77 | 6.34 | 6.45 |
| NeuAc2Hex5HexNAc4 | 2221.78 | 13.20 | 12.86 | 17.63 |
| NeuAc2Hex5HexNAc4dHex | 2367.83 | 14.04 | 29.28 | 20.71 |
| NeuAc2Hex5HexNAc4dHex2 | 2513.89 | 0.47 | n.d. | 5.94 |

The columns show relative glycan signal intensities (% of the tabled signals) before the modification reactions (MNC), after α2,3-sialyltransferase reaction (α2,3SAT), and after sequential α2,3-sialyltransferase and α1,3-fucosyltransferase reactions (α2,3SAT + α1,3FucT).
The sum of the glycan signal intensities in each column has been normalized to 100% for clarity.

TABLE 5

Mass spectrometric analysis results of selected neutral N-glycans in enzymatic modification steps of human cord blood mononuclear cells.

| Proposed monosaccharide composition | calc m/z [M + H]⁺ | MNC | SA'ase | α2,3SAT | α1,3FucT | α2,3SAT + α1,3FucT |
|---|---|---|---|---|---|---|
| Hex5HexNAc2 | 1257.42 | 11.94 | 14.11 | 14.16 | 13.54 | 9.75 |
| Hex3HexNAc4dHex | 1485.53 | 0.76 | 0.63 | 0.78 | 0.90 | 0.78 |
| Hex6HexNAc3 | 1622.56 | 0.61 | 1.99 | 0.62 | 0.51 | 0.40 |
| Hex5HexNAc4 | 1663.58 | 0.44 | 4.81 | 0.00 | 0.06 | 0.03 |
| Hex5HexNac4dHex | 1809.64 | 0.19 | 1.43 | 0.00 | 0.25 | 0.00 |
| Hex5HexNac4dHex2 | 1955.7 | 0.13 | 0.22 | 0.00 | 0.22 | 0.00 |
| Hex6HexNAc5 | 2028.71 | 0.07 | 1.14 | 0.00 | 0.00 | 0.00 |

TABLE 5-continued

Mass spectrometric analysis results of selected neutral N-glycans in enzymatic modification steps of human cord blood mononuclear cells.

| Proposed monosaccharide composition | calc m/z [M + H]+ | MNC | SA'ase | α2,3SAT | α1,3FucT | α2,3SAT + α1,3FucT |
|---|---|---|---|---|---|---|
| Hex5HexNAc4dHex3 | 2101.76 | 0.12 | 0.09 | 0.00 | 0.22 | 0.00 |
| Hex6HexNAc5dHex | 2174.77 | 0.00 | 0.51 | 0.00 | 0.14 | 0.00 |
| Hex6HexNAc5dHex2 | 2320.83 | 0.00 | 0.00 | 0.00 | 0.08 | 0.00 |

The columns show relative glycan signal intensities (% of the total glycan signals) before the modification reactions (MNC), after broad-range sialidase reaction (SA'se), after α2,3-sialyltransferase reaction (α2,3SAT), after α1,3-fucosyltransferase reaction (α1,3FucT), and after sequential α2,3-sialyltransferase and α1,3-fucosyl-transferase reactions (α2,3SAT + α1,3FucT).

TABLE 6

Proposed monosaccharide compositions for NeuGc-containing or O-acetylated sialic acid containing glycans and their calculated isotopic masses

| Proposed structures | m/z isotopic |
|---|---|
| NeuGcHex3HexNAc3 | 1419.48964 |
| NeuAcHex3HexNAc3Ac | 1445.50529 |
| NeuGcHex4HexNAc3 | 1581.54246 |
| NeuAcHex4HexNAc3dHex/NeuGcHex3HexNAc3dHex2 | 1711.60545 |
| NeuGc2Hex3HexNAc3 | 1726.57996 |
| NeuAcHex5HexNAc3/NeuGcHex4HexNAc3dHex | 1727.60036 |
| NeuGcHex5HexNAc3 | 1743.59528 |
| NeuGcHex4HexNac4 | 1784.62183 |
| NeuAcHex5HexNAc3dHex/NeuGcHex4HexNAc3dHex2 | 1873.65827 |
| NeuGcHex5HexNAc4 | 1946.67465 |
| NeuAcHex5HexNAc4Ac | 1972.6903 |
| NeuAc2Hex5HexNAc3/NeuGcNeuAcHex4HexNAx3dHex | 2018.69578 |
| NeuGcHex5HexNAc4SP | 2026.63146 |
| NeuGc2Hex4HexNAc4 | 2091.71215 |
| NeuAcHex6HexNAc4/NeuGcHex5HexNAc4dHex | 2092.73255 |
| NeuAcHex9HexNAc2/NeuAcHex6HexNAc4SP/NeuGcHex5HexNAc4dHexSP | 2172.732/2172.689 |
| NeuAc2Hex6HexNAc3/NeuGcHex4HexNac3dHex2 | 2180.7486 |
| NeuGcNeuAc2Hex2HexNAc4dHex | 2188.76491 |
| NeuGcNeuAcHex6HexNAc3 | 2196.74351 |
| NeuGcNeuAcHex5Hexnac4 | 2237.77006 |
| NeuAcHex6HexNAc4dHex/NeuGcHex5HexNAc4dHex2 | 2238.79046 |
| NeuGc2Hex5Hexnac4 | 2253.76497 |
| NeuAcHex7HexNAc4/NeuGcHex6HexNAc4dHex | 2254.78537 |
| NeuAc2Hex5HexNAc4Ac | 2263.78571 |
| NeuAc2Hex5HexNAc4Ac2 | 2305.79627 |
| NeuAc2Hex5HexNAc3dHex2/NeuGcNeuAcHex4HexNAc3dHex3 | 2310.81159 |
| NeuAcHex5HexNAc3dHex4NeuGcHex6HexNAc5 | 2311.83199 |
| Hex6HexNAc4dHex3SP/NeuGcNeuAcHex3HexNAc6 | 2319.76768 |
| NeuGcHex3HexNAc6dHex2 | 2320.84355 |
| NeuAcHex5HexNAc5dHexAc | 2321.82757 |
| NeuGcHex6HexNAc4dHexSP | 2334.74219 |
| NeuGcNeuAc2Hex4HexNAc4 | 2366.81265 |
| NeuAc2Hex6HexNAc4/NeuGcNeuAcHex5HexNAc4dHex | 2383.82797 |
| NeuAcHex6HexNAc4dHex2/NeuGcHex5HexNAc4dHex3 | 2384.84837 |
| NeuAc2Hex5HexNAc4Ac4 | 2389.8174 |
| NeuGc2Hex5HexNAc4dHex | 2399.82288 |
| NeuAc2Hex5HexNAc4dHexAc | 2409.84361 |
| NeuAc2Hex5HexNAc4dHexAc2 | 2451.85418 |
| NeuAcHex5HexNAc5dHex2Ac | 2467.88548 |
| NeuAcHex6HexNAc5Ac | 2483.88039 |
| NeuGcNeuAc2Hex5HexNAc4 | 2528.86547 |
| NeuAc2Hex6HexNAc4dHex/NeuGcNeuAcHex5HexNAc4dHex2 | 2529.88587 |
| NeuGc2NeuAcHex5HexNAc4 | 2544.86039 |
| NeuGc2Hex5Hexnac4dHex2/NeuGcNeuAcHex6HexNAc4dHex | 2545.88079 |
| NeuGc3Hex5HexNAc4 | 2560.8553 |
| NeuGcNeuAcHex6HexNAc5 | 2602.90225 |
| NeuAcHex7HexNAc5dHex/NeuGcHex6HexNAc5dHex2 | 2603.92265 |
| NeuGc2Hex6HexNac5 | 2618.89716 |
| NeuGcHex7HexNAc5dHex | 2619.91756 |
| NeuGcHex8HexNAc5 | 2635.91248 |
| NeuGcNeuAc2Hex5HexNAc4dHex | 2674.92338 |
| NeuGcHex6HexNAc5dHex2SP | 2683.87947 |
| NeuAc2Hex6HexNAc3dHex4/NeuGc2Hex6HexNAc5dHex | 2764.980/764.955 |
| NeuAcHex9HexNAc5/NeuGcHex8HexNAc5dHex | 2781.97038 |
| NeuGcNeuAc2Hex6HexNAc5 | 2893.99766 |
| NeuAc2Hex7HexNAc5dHex/NeuGcNeuAcHex6HexNAc5dHex2 | 2895.01806 |

TABLE 6-continued

Proposed monosaccharide compositions for NeuGc-containing or O-acetylated sialic acid containing glycans and their calculated isotopic masses

| Proposed structures | m/z isotopic |
|---|---|
| NeuGc2Hex6HexNAc5dHex2 | 2911.01298 |
| NeuGc3Hex6HexNAc5 | 2925.98749 |
| NeuGcNeuAc2Hex5HexNAc6 | 2935.02421 |
| NeuGcNeuAcHex7HexNAc6dHex2 | 3260.15025 |
| NeuGcHex7HexNAc6dHex4 | 3261.17065 |

TABLE 7

Fold change of CMAH gene expression in CD34+ and CD133+ cells assessed by microarray and qRT-PCR analysis.

| | Microarray | Mean Fold Change | qRT-PCR | Mean Fold Change |
|---|---|---|---|---|
| CMAH/ CD34+ | 205518_s_at | 3.0 | Hs00186003_m1 | 5.9 |
| | 210571_s_at | No Change | | |
| | 1554862_at | No Change | | |
| | 229604_at | No Change | | |
| CMAH/ CD133+ | 205518_s_at | 7.0 | Hs00186003_m1 | 4.4 |
| | 210571_s_at | 9.2 | | |
| | 1554862_at | No Change | | |
| | 229604_at | 4.9 | | |

TABLE 8

DNA sequence of oligonucleotides used. CMP-N-acetylneuraminic acid hydroxylase (CMAH) primers 1-5 designed from the sequence information in GenBank accession number D86324, β-2-microglobulin (B2M) primers designed from GenBank accession number NM_004048. UTR = untranslated region

| Primer | Direction | Sequence (5' to 3') | Product size (location) |
|---|---|---|---|
| CMAH_UP1 | sense | CCTGTTGTGCCTATCACCTGTTG | 2194 bp (full-length) |
| CMAH_DO1 | antisense | CAGGAGACAAATTCCACCATTGA | |
| CMAH_UP2 | sense | same as CMAH_UP1 | 524 bp (5'-UTR + 5'-end) |
| CMAH_DO2 | antisense | ATCTGGTCTTCTCCCAGCAAGC | |
| CMAH_UP3 | sense | CCTGAGTTACCCCACACTGAAA | 508 bp (5'-end) |
| CMAH_DO3 | antisense | GTCTGATGGGTGAGATTCCACA | |
| CMAH_UP4 | sense | ACTACAAGGCTTGGCTGGTGAAG | 692 bp (middle) |
| CMAH_DO4 | antisense | TGACTTCCAGTTGGGTGGTGTG | |
| CMAH_UP5 | sense | GGAAGTCATTCCTGATGTGCTGT | 610 bp (3'-end + 3'-UTR) |
| CMAH_DO5 | antisense | same as CMAH_DO1 | |
| B2M_UP | sense | CTCGCGCTACTCTCTCTTTCTGG | 335 bp |
| B2M_DO | antisense | GCTTACATGTCTCGATCCCACTTAA | |

TABLE 9

RT-PCR analysis of CMP-N-acetylneuraminic acid hydroxylase (CMAH) and β-2-microglobulin (B2M) mRNA expression in different human stem cell sources.

| Lane | Sample | CMAH | B2M |
|---|---|---|---|
| 1 | HUCB MNC | +++ | + |
| 2 | HUCB MNC -RT ctrl | − | − |
| 3 | HUCB CD34+ | + | + |
| 4 | HUCB CD34+ -RT ctrl | − | − |
| 5 | HUCB CD34− | +++ | + |
| 6 | HUCB CD133+ | ++++ | + |
| 7 | HUCB CD133− | ++ | + |
| 8 | HUCB Lin− | ++ | + |
| 9 | HUCB Lin+ | − | + |
| 10 | Cambrex HUCB MNC | ++ | + |
| 11 | Cambrex MPB | − | − |
| 12 | Cambrex BM MNC | ++ | + |
| 13 | HUH-7 cell line | +/− | + |
| 14 | HUH-7 cell line -RT ctrl | − | − |
| 15 | HUCB MSC line 1. | ++ | + |
| 16 | BM MSC line 1. | +++ | + |
| 17 | hESC cell line 1. | + | + |
| 18 | hESC cell line 1. -RT ctrl | − | − |
| 19 | hESC cell line 2. | + | + |
| 20 | hESC cell line 3. | + | + |
| 21 | MEF | − | − |

TABLE 9-continued

RT-PCR analysis of CMP-N-acetylneuraminic acid hydroxylase (CMAH) and β-2-microglobulin (B2M) mRNA expression in different human stem cell sources.

| Lane | Sample | CMAH | B2M |
|---|---|---|---|
| 22 | MEF -RT ctrl | – | – |
| 23 | water | – | – |

Lane numbering corresponds to gel electrophoresis picture in FIG. 9.
CMAH expression levels: ++++ (very high), +++ (high), ++ (medium), + (low), +/– (trace), – (none detected).
B2M expression only indicated as detected (+) or absent (–).
HUCB = human umbilical cord blood,
MNC = mononuclear cells,
MPB = progenitor cells mobilized from the bone marrow,
HUH-7 = human cell line,
MSC = mesenchymal cells,
hESC = human embryonic stem cells,
MEF = mouse feeder cells.

TABLE 10

| Acid | Time | Protein | N-glycan sialylation level (%) | | |
|---|---|---|---|---|---|
| | | | SA(0) | SA(1) | SA(2) |
| Propionic acid 2 M | 1 h | +++ | — | 100 | — |
| (Serum protein 3 +80° C. mg/ml) | 2 h | ++ | — | 100 | — |
| | 3 h | ++ | n.d. | n.d. | n.d. |
| | 4 h | + | n.d. | n.d. | n.d. |
| Sulfuric acid 12.5 mM | 0.5 h | ++++ | 73.4 | 24.2 | 2.4 |
| (Serum protein 2.5 +80° C. mg/ml) | 1 h | ++ | 90.3 | 7.3 | 2.4 |
| Hydrochloride acid 50 mM | 8 h | ++++ | 75.9 | 24.1 | — |
| (Serum protein 2.5 +50° C. mg/ml) | 16 h | ++ | 93.9 | 6.1 | — |
| Hydrochloride acid 100 mM | 4 h | +++++ | | | |
| (Serum protein 2.5 +37° C. mg/ml) | 16 h | +++++ | | | |
| | 16 h | +++++ | 47.7 | 42.1 | 10.2 |
| | 24 h | ++++ | 43.2 | 45.5 | 11.3 |
| | 40 h | +++ | 83.3 | 16.7 | — |
| | 48 h | +++ | 89.5 | 10.5 | — |

+++++ Protein has survived completely
++++ Protein has survived almost entirely
+++ Protein is slightly degraded
++ Protein is heavily degraded
+ Protein is totally destroyed
>98% of the biantennary N-glycan backbone survived intact the acid hydrolysis

The invention claimed is:

1. A method for evaluating the status of an isolated early human cell population comprising a step of detecting the presence or absence in said population of at least one monosaccharide sialic acid structure NeuGc or Neu-O-Ac with the provision that when the early human cell is embryonal type stem cell the monosaccharide sialic acid structure is not NeuGc; or at least one specific glycan with structure SAα3/6Galβ(3/4GlcNAcβ)$_n$, wherein SA is sialic acid or a derivative thereof and n is 0 or 1, with the provision that when the early human cell population is a CD34+ cell population, the glycan structure is not single epitope SAα3Galβ4GlcNAc.

2. The method according to claim 1 comprising a step of detecting the presence or absence in said population of at least one of the following saccharide structures:
i) monosaccharide sialic acid Neu-O-Ac,
ii) monosaccharide sialic acid NeuGc, wherein the early human cell is a human early blood cell or a mesenchymal stem cell;
iii) specific sialyllactosamine glycan with structure SAα3/6Galβ3/4GlcNAcβ, wherein SA is sialic acid or a derivative thereof and n is 0 or 1, and wherein the early human cell population is mesenchymal stem cell or embryonal type stem cell; and
iv) specific sialyllactosamine glycan structure SAα6Galβ3/4GlcNAcβ or SAα3Galβ3GlcNAc, wherein SA is sialic acid or a derivative thereof and n is 0 or 1.

3. A method for evaluating the status of an isolated early human cell population comprising a step of detecting the presence or absence in said population of at least one specific N-glycan with structure SAα3/6Galβ3/4GlcNAcβ, wherein SA is an unusual sialic acid (NeuGc or Neu-O-Ac) or a derivative thereof, optionally with the provision that when the early human cell population is a CD34+ cell population, the glycan structure is not single epitope SAα3Galβ4GlcNAc.

4. The method according to claim 1, wherein the structure is linked to an N-glycan core structure Mα3{Mα6}Mβ4GNβ4{Fucα6}$_{r3}$GN, wherein r3 is 0 or 1 { } indicates branching which may also be present or absent.

5. The method according to claim 1, wherein the structure is according to Formula III {SAα3/6}$_{s1}$LNβ2Mα3{{SAα3/6}$_{s2}$LNβ2Mα6}$_{r8}$MβGNβ4{Fucα6}$_{r3}$GN  (III)

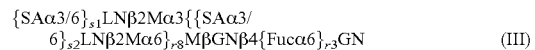

wherein s1, and s2 and r3 are independently 0 or 1,
with the provision that at least r1 is 1 or r2 is 1, and at least s1, or s2 is 1;
LN is N-acetyllactosaminyl also marked as GalβGN, GN is GlcNAc, M is mannosyl-.

6. The method according to claim 1 comprising a step of detecting the presence or absence in said population of at least one of the following saccharide structures:
iv) monosaccharide sialic acid Neu-O-Ac,
v) monosaccharide sialic acid NeuGc, wherein the early human cell is a human early blood cell or a mesenchymal stem cell.

7. The method according to claim 6, wherein the monosaccharide sialic acid residue is a part of sialyllactosamine glycan structure according to formula SAα3/6Galβ3/4GlcNAcβ, wherein SA is Neu-O-Ac or NeuGc or a derivative thereof.

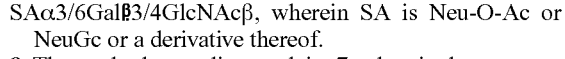

8. The method according to claim 7, wherein the presence of the sialic acid is associated with cell culture medium or wherein the presence of NeuGc is associated with the presence of animal serum or proteins or Neu-O-Ac is associated with cell culture medium comprising horse serum.

9. The method according to claim 1, wherein the evaluation is performed by specific binder reagent or by mass spectrometry.

10. The method according to claim 9, wherein the structure is defined by mass spectrometry and
   wherein the presence or absence of Neu-O-Ac is analysed by indicative glycan signals, differentiated from unmodified sialic acids by mass of $C_2H_2O$ functional group residue or corresponding signal(s) assigned to Neu-O-Ac-structures listed in Table 6 or
   wherein NeuGc is analysed by indicative glycan signals, using rounded exact mass numbers as glycan names, at m/z 1946, m/z 2237, and m/z 2253 or corresponding and additional signal assigned to NeuGc-structures listed in Table 1 and/or Table 6, with optional provision that when the mass number corresponds also to alternative structures the presence of NeuGc is further verified by other data, and/or
   wherein mass spectrometric analysis comprises releasing of glycans, purification of the glycan fraction, measuring molecular masses; optionally modifying part of glycans by specific sialidase enzymes and analysing the modified glycans; and assigning/fitting the molecular masses of glycans to said specific structures.

11. The method according to claim 9, wherein the binding reagents include specific binding protein; or binding protein selected from the group consisting of: an enzyme, a lectin and a glycan binding antibody, or by P3 antibody specific for NeuGc structures.

12. The method according to claim 1, wherein specific sialyllactosamine glycan with structure SAα3/6Galβ(3/4GlcNAcβ)$_n$, wherein SA is sialic acid or a derivative thereof and n is 0 or 1, is detected from the early human cell population comprising embryonal type stem cell.

13. The method according to claim 12, wherein the sialic acid is NeuGc and the early human cell population is embryonal type stem cell.

14. The method according to claim 12, wherein the evaluation is performed by specific binder reagent or by mass spectrometry.

15. The method according to claim 14, wherein the detection is performed by P3 antibody specific for NeuGc structures or Neu-O-Ac is detected by lectin.

16. The method according to claim 14, wherein NeuGc is analyzed by indicative glycan signals, using rounded exact mass numbers as glycan names, at m/z 1946, m/z 2237, and m/z 2253 or corresponding and additional signal assigned to NeuGc-structures listed in Table 1 and/or Table 6, with an optional provision that when the mass number corresponds also to alternative structures the presence of NeuGc is further verified by other data, and an N-glycan is detected, wherein NeuGc is analysed by indicative glycan signals, at m/z 1946, m/z 2237, and m/z 2253 are detected in negative ion mode as [M-H]$^-$ adducts or signals with corresponding monosaccharide composition are detected.

17. The method according to claim 1, wherein specific sialyllactosamine glycan structure SAα6Galβ3/4GlcNAcβ or SAα3Galβ3GlcNAcβ, or SAα3/6Galβ3/4GlcNAcβ, wherein SA is sialic acid or a derivative thereof and n is 0 or 1, is detected from mesenchymal stem cell or embryonal type stem cell population.

18. The method according to claim 17, wherein the sialic acid is Neu5Ac and wherein specific sialyllactosamine glycan structure SAα6Galβ3/4GlcNAcβ or SAα3Galβ3GlcNAcβ, and the cell population is selected from the group consisting of: early human blood cell, cord blood cells, and cord blood CD133+ cells.

19. The method according to claim 18, wherein the sialic acid is Neu5Ac and the glycan is SAα3/6Galβ3/4GlcNAcβ.

20. The method according to claim 19, wherein the Neu5Ac structure is linked to an N-glycan core structure.

21. The method according to claim 18, wherein the evaluation is performed by specific binder reagent or by mass spectrometry.

22. The method according to claim 21, wherein the detection is performed by a sialidase enzyme specifically cleaving α3-linked sialic acids.

23. The method according to claim 22, where in the detection is performed by detecting any of the mass spectrometric signals listed in Table 1.

24. The method according to claim 1 involving the detection of N-glycan comprising Neu-OAc or NeuGc and counting proportion of NeuGc and/or O-acetylated sialic acid from total sialic acids in N-glycans.

25. The method according to claim 1, wherein the glycan structure is quantitatively determined.

26. The method according to claim 1, wherein the detection step comprises recognizing the structure directly or indirectly by a) contacting a sample of human early cell population with a reagent specifically recognizing said structure; or b) analyzing the presence of the structure by physical and/or chemical characteristics of the structure; or c) analyzing the presence of a mRNA corresponding to a glycosylation enzyme correlated with the expression of the structure.

27. The method according to claim 1, wherein structures SAα3Gal and SAα6Gal are detected.

28. The method according to claim 1, wherein the cell population is a limited solid tissue progenitor cell population or homogenous early human cell population.

29. The method according to claim 1, wherein the cell population is evaluated with regard to a contaminating structure in the cell population or a change in the status of the cell population.

30. The method according to claim 1 for the control of cell status and/or potential contaminations by physical and/or chemical means, the method comprising glycosylation analysis using mass spectrometric analysis of glycans in a cell sample or detection of the structure by an antibody.

31. The method according to claim 1 for control of a variation in raw material cell population or which comprises detecting an individual specific variation.

32. The method according to claim 1, wherein the cell status is controlled under a condition selected from the group consisting of: during cell culture or during cell purification, in context with cell storage or handling at lower temperatures, or in context with cryopreservation of cells; time dependent changes of cell status are detected, or time dependent changes of cell status depend on the nutritional status of the cells, confluency of the cell culture, density of the cells, changes in genetic stability of the cells, integrity of the cell structures or cell age, or chemical, physical, or biochemical factors affecting the cells; and the cell status is controlled for a differentiating cell population.

33. The method according to claim 1, wherein glycan structures are analyzed from a reagent, wherein the reagent is selected from the group consisting of: a reagent to be used in handling of isolated early human cell population, a reagent to be used in handling of isolated early human cell population, wherein the handling of cell population involves at least one process selected from the group consisting of: cell preservation, cell preparation, and cell culture; and a reagent to be used in handling of isolated early human cell population wherein the reagent is of animal origin, or a reagent to be used in handling of isolated early human cell population and comprising contaminating structure NeuGc-structure or Neu-OAc and the early cell population is controlled with regard to reagents used in cell purification.

34. The method according to claim 33, wherein the cells are prepared by a method using magnetic beads, and the cells are early human cells.

35. The method according to claim 34, wherein the cells are prepared by a method using magnetic beads and magnetic bead blocking reagent, Fc-blocking reagent and albumin used for washing the cells.

36. The method according to claim 1 further comprising cultivating said cell population with controlled glycoprotein reagents wherein the reagent derived from material comprising NeuGc or Neu-OAc, is selected from the group consisting of: a cell culture material derived from animal material comprising NeuGc or Neu-OAc, wherein sialic acid residues are removed by enzymatic or acid treatment; or a glycoprotein reagent selected from the group consisting of: albumins, gelatins, antibodies, FcR-blocking reagents, serum proteins, serums and cell modification enzyme reagents; glycoprotein reagent selected from the group consisting of: cell culture media, cell culture reagent, and serum replacement reagent for cell culture, or glycoprotein containing NeuAcαGal-structures, but is free of NeuGcαGal-structures and/or Neu-O-AcαGal-structures or glycoprotein is a glycan depleted glycoprotein, a glycan depleted glycoprotein, wherein the glycoprotein is a non-animal glycoprotein or a prokaryotic glycoprotein.

37. The method according to claim 1, comprising altering terminal sialic acid glycosylation and/or fucosylation of a trisaccharide epitope for an isolated early human cell population, wherein the altering comprises a reaction step of contacting the cells with at least one glycosidase and/or glycosyltransferase enzyme capable of altering said glycan structure on an intact cell.

38. The method according to claim 37, wherein the cell population is desialylated and optionally resialylated or sialylated by CMP-sialic acid and a specific sialyltransferase enzyme or fucosylated with an α3- and/or α4-linked fucose by incubating cells with GDP-Fuc acid and a fucosyltransferase enzyme.

39. The method according to claim 1 comprising the step(s) of optionally removing sialic acids including two or more linkage types or specifically α3- and/or α6-linked sialic acids from the surface of the cells and/or b) sialylating the cells by the use of CMP-sialic acid and a specific sialyltransferase enzyme.

40. The method according to claim 37, comprising removing sialic acid structures SAα3 and/or SAα6 from early human cells.

41. The method according to claim 37, wherein the method comprises sialylation with specific α3- and/or α6-linked sialic acids by incubating cells with CMP-sialic acid and sialyltransferase enzyme and optionally further fucosylation with specific α3- and/or α4-linked fucose by incubating cells with GDP-Fuc acid and fucosyltransferase enzyme.

42. The method according to claim 41, wherein the method comprises characteristics selected from the group consisting of:
the cells are desialylated or sialyl-Lewis x is synthesised by the steps of i) optionally desialylating cells, ii) sialylating by α3-sialyltransferase and iii) fucosylating by α3-fucosyltransferase or the method involves synthesis of linkage specific α3-sialylation, specific α6-sialylation, or specific mixture α3- and α6-sialylated structures on N-glycan core structures on the specific cell types or either NeuAc or NeuGc are quantitatively synthesized to the cell surface or NeuGc is removed from said cell populations, and then said cells are resialylated with NeuAc or the cell population is desialylated and optionally resialylated linkage specifically or the sialidase and/or sialyltransferase reagent(s) are/is a controlled reagent with regard to carbohydrate material present.

43. The method according to claim 39, wherein NeuGc or Neu-OAc is quantitatively removed from the cells.

44. The method according to claim 39, wherein the altered cell line produced is analyzed for the quantitative verification of the alteration in glycan structures.

45. The method according to claim 41, further comprising modification of human neonatal blood cells and subpopulations thereof and multipotent cell lines or
sialylation and/or desialylation to produce sialylated structures on the specific cell types according to claim 1 to the surfaces of cells in intact form, optionally for studies of biological activities of the cells.

46. A controlled reagent for cell modification of cells according to claim 37 being recombinant human sialyltransferase or fucosyltransferase comprising biantennary N-glycan with terminal structures NeuAcα3/α6Gal, wherein said reagent is optionally selected from the group consisting of: a modification enzyme, which is purified from the modified cells, or modification enzyme, which is affinity purified to remove the enzyme, or modification enzyme, which is tagged and removed by binding of the tag to matrix, or modification enzyme, which is immobilized to a matrix and removed by separating the matrix from the cells, or modification enzyme, which is a human acceptable enzyme, or modification enzyme, which is a human acceptable enzyme being a recombinant enzyme i) corresponding to secreted form the human enzyme ii) comprising controlled and iii) optionally modified glycan structures.

47. The method according to claim 1, comprising binding the glycan structures of specific cell types with a binder, wherein the specific cell type is isolated early human cell populations.

48. The method according to claim 47, wherein the binder is an enzyme, a lectin, an antibody, a monoclonal antibody, a human antibody or a humanized antibody.

49. The method according to claim 48, wherein said enzyme recognizes specifically terminal sialic acid, or said antibody recognizes terminal sialic acid structure, or said lectin specifically recognizing structure.

50. The method according to claim 49, wherein the antibody recognizes a structure NeuGcα3Galβ4Glc(NAc)$_{0\ or\ 1}$ or GalNAcβ4[NeuGcα3]Galβ4Glc(NAc)$_{0\ or\ 1}$, wherein [] indicates branch in the structure and ( )$_{0\ or\ 1}$ a structure being either present or absent.

51. The method according to claim 48, with reagent selected from the group consisting of
the lectin is specific for SAα3Gal-structures or the lectin is specific for SAα6Gal-structures;
or the binder is conjugated to a label structure,
or the binder is conjugated to a label structure being a fluorescent molecule, a radioactive molecule, a detectable enzyme or biotin/streptavidin/avidin,
or the binder is conjugated to a label structure being a fluorescent molecule, a radioactive molecule, a detectable enzyme or biotin/streptavidin/avidin and the label structure is immobilized on solid surface.

52. The method according to claim 47, comprising analysis of the presence or content of the structure on the surface of the cells.

53. The method according to claim 47, wherein cells bound by the binder are separated by binding to solid phase or by cell sorting means.

54. A method according to claim 1, further including analysis of CMAH or fragment thereof or using reagent selected from the group consisting of: a peptide for production of antibodies for studies of protein level expression of the novel mRNA or a novel human mRNA corresponding to human CMAH-gene or C-terminal peptide thereof, and a corresponding mRNA probe for analysis of human stem cells.

55. The method according to claim 1 comprising a step of detecting the presence or absence of at least one sialic acid monosaccharide selected being either NeuGc or Neu-O-Ac, with the provision that when the monosaccharide is NeuGc, the early human cell population is not a human embryonal stem cell population.

56. A method for recognizing a non-human sialic acid (SA) selected from the group consisting of Neu5Gc and o-acetylated sialic acids, in human stem cells, comprising contacting a monoclonal antibody and/or other binder with a terminal structure on a specific cell type according to claim 1.

57. A method according to claim 1, further comprising a controlled reagent, wherein the controlled reagent is selected from the group consisting of: reagents with no observable levels of harmful glycan structure.

58. The method according to claim 57, wherein the controlled reagent is desialylated protein.

59. The method according to claim 10, wherein the presence of NeuGc is verified by mass spectrometric or labelling data.

60. The method according to claim 16, wherein the presence of NeuGc is verified by mass spectrometric or labelling data.

61. The method according to claim 26, wherein the presence of the structure is analysed by mass spectrometry.

62. The method according to claim 36, wherein the protein is a prokaryotic glycoprotein and the cell population is an early human blood cell population.

63. The method according to claim 49, wherein said enzyme recognizes terminal SA$\alpha$3.

64. The method according to claim 49, wherein said antibody recognizes a NeuGc-structure, a Neu-O-Ac structure, a SA$\alpha$3-structure or a SA$\alpha$6-structure.

65. The method according to claim 51, wherein the lectin is Maackia amuriensis lectin.

66. The method according to claim 51, wherein the lectin is Sambucus nigra agglutinin.

* * * * *